(12) United States Patent
Morrow et al.

(10) Patent No.: US 7,438,909 B2
(45) Date of Patent: *Oct. 21, 2008

(54) IMMUNIZATION AND TREATMENT METHODS FOR ANTHRAX

(75) Inventors: Phillip R. Morrow, deceased, late of San Diego CA (US); by Jeanne Morrow, legal representative, San Diego, CA (US); Angray S. Kang, Encinitas, CA (US); Fei Wang, San Diego, CA (US); Ivy Jiang, San Diego, CA (US); Ritsuko Sawada, San Diego, CA (US); Wolfgang Scholz, San Diego, CA (US)

(73) Assignee: Emergent Product Development Gaithersburg Inc., Gaithersburg, MD (US)

( * ) Notice: Subject to any disclaimer, the term of this patent is extended or adjusted under 35 U.S.C. 154(b) by 48 days.

This patent is subject to a terminal disclaimer.

(21) Appl. No.: 11/041,763

(22) Filed: Jan. 24, 2005

(65) Prior Publication Data

US 2008/0081042 A1    Apr. 3, 2008

Related U.S. Application Data

(63) Continuation of application No. 11/040,580, filed on Jan. 21, 2005, and a continuation-in-part of application No. PCT/US03/36555, filed on Nov. 14, 2003.

(60) Provisional application No. 60/562,421, filed on Apr. 15, 2004, provisional application No. 60/538,721, filed on Jan. 23, 2004.

(51) Int. Cl.
*A61K 39/395* (2006.01)
*A61K 39/40* (2006.01)

(52) U.S. Cl. .................................. 424/142.1; 424/150.1
(58) Field of Classification Search .............. 424/142.1, 424/150.1, 164.1; 530/388.1, 388.2, 388.4
See application file for complete search history.

(56) References Cited

U.S. PATENT DOCUMENTS

| | | | |
|---|---|---|---|
| 5,677,274 A | 10/1997 | Leppla et al. | |
| 5,811,524 A | 9/1998 | Brams et al. | |
| 5,958,765 A | 9/1999 | Brams et al. | |
| 6,329,156 B1 | 12/2001 | Cirino et al. | |
| 6,387,665 B1 | 5/2002 | Ivins et al. | |
| 6,413,771 B1 | 7/2002 | Brams et al. | |
| 6,537,809 B2 | 3/2003 | Brams et al. | |
| 6,770,479 B1 | 8/2004 | Lee et al. | |
| 6,828,110 B2 | 12/2004 | Lee et al. | |
| 6,916,474 B2 | 7/2005 | Harvey et al. | |
| 7,261,900 B2 | 8/2007 | Leppla et al. | |
| 2003/0108556 A1 | 6/2003 | Mekalanos et al. | |
| 2003/0118591 A1 | 6/2003 | Levy | |
| 2003/0143636 A1 | 7/2003 | Simonson et al. | |
| 2003/0202989 A1 | 10/2003 | Collier et al. | |
| 2004/0009178 A1* | 1/2004 | Bowdish et al. | ......... 424/164.1 |
| 2004/0009945 A1 | 1/2004 | Lee et al. | |
| 2004/0014707 A1 | 1/2004 | Cirino et al. | |
| 2004/0076631 A1 | 4/2004 | Brams et al. | |
| 2004/0076638 A1 | 4/2004 | Shiloach et al. | |
| 2004/0166120 A1 | 8/2004 | Thomas et al. | |
| 2004/0171121 A1 | 9/2004 | Leppla et al. | |
| 2004/0235075 A1 | 11/2004 | Collum et al. | |
| 2005/0054038 A1 | 3/2005 | Bhatnagar et al. | |
| 2005/0063986 A1 | 3/2005 | Bhatnagar et al. | |
| 2005/0287149 A1 | 12/2005 | Keler et al. | |
| 2006/0258842 A1 | 11/2006 | Groen et al. | |

FOREIGN PATENT DOCUMENTS

WO   WO 03/076568 A2   9/2003
WO   WO 2005/120567    12/2005

OTHER PUBLICATIONS

Abbas et al Cellular and Molecular Immunology, W.B. Saunders Co., 1991, p. 50-57, 75-89.*
Bendig (Methods: A Companion to Methods in Enzymology 1995; 8:83-93).*
Sawada-Hirai et al (Journal of Immune Based Therapies and Vaccines 2:5, May 12, 2004).*
Cirino et al (Infection and Immunity, 67(6):2957-2963, Jun. 1999).*
Choi et al (Abstracts of the Intersceince Conference on Antimicrobial Agents and Chemotherapy; 43:277, Sep. 14-17, 2003).*
Karginov et al (FEMS Immunology and Medical Microbiology; 40:71-74, 2004—first published on line Nov. 7, 2003).*
Casadevall (Emerging Infectious Diseases, 8(8):833-841, Aug. 2002).*

(Continued)

*Primary Examiner*—Patricia A. Duffy
(74) *Attorney, Agent, or Firm*—Sterne, Kessler, Goldstein & Fox P.L.L.C.

(57) ABSTRACT

A highly efficient method for generating human antibodies using recall technology is provided. In one aspect, human antibodies which are specific to the anthrax toxin are provided. In one aspect, human peripheral blood cells that have been pre-exposed to anthrax toxin are used in the SCID mouse model. This method results in high human antibody titers which are primarily of the IgG isotype and which contain antibodies of high specificity and affinity to desired antigens. The antibodies generated by this method can be used therapeutically and prophylactically for preventing or treating mammals exposed to anthrax. Thus, in one embodiment, a prophylactic or therapeutic agent used to counter the effects of anthrax toxin, released as a mechanism of bioterrorism, is provided. In one embodiment, a formulation and method for preventing and/or treating anthrax infection comprising a binding agent that prevents the assembly of the PA63 heptamer is also provided. Methods for diagnosis and methods to determine anthrax contamination are also described.

14 Claims, 23 Drawing Sheets

OTHER PUBLICATIONS

Bull et al (Science 297:201-202, Jul. 12, 2002).*
Binder et al (Comp. Immun. Microbiol. Infect. Dis. 26:401-421, 2003).*
Bohannon (Science 300:414-415, Apr. 18, 2003).*
Stiehm et al, Passive Immunization, Textbook of Pediatric Infectious Diseases 4th Ed. vol. 2, Philadelphia: WB Saunders Company, pp. 3769-3802, 1998.*
Lacy, DB et al. "Crystal structure of the von Willebrand factor A domain of human capillary morphogenesis protein 2: an anthrax toxin receptor." *Proc Natl Acad Sci USA* Apr. 27, 2004; 101(17):6367-72, Epub Apr. 12, 2004.
Wigelsworth, DJ et al. "Binding Stoichiometry and Kinetics of the Interaction of a Human Anthrax Toxin Receptor, CMG2, with Protective Antigen." *J. Biol. Chem.*, vol. 279, Issue 22 (May 28, 2004): 23349-23356.
Jonah, G. et al. "Antitoxins: Novel Strategies to Target Agents of Bioterrorism." *Microbiology*, vol. 2, 721-726, Sep. 2004.
Sellman, Bret R. et al. "Dominant-Negative Mutants of a Toxin Subunit: An Approach to Therapy of Anthrax." *Science*, vol. 292 (Apr. 27, 2001): 695-697.
Mourez, Michael et al. "Designing a polyvalent inhibitor of anthrax toxin." *Nature Biotechnology*, vol. 19 (Oct. 2001): 958-961.
"New Approaches Combat Anthrax's Deadly Effects" Respiratoryreviews.com, Zucker, Mimi, Ph.D. Apr. 4, 2005.
"Mechanism of Anthrax Toxins" *The Biotech Journal*. Nov./Dec. 2003. <www.biotechjournal.com>.
Rodney Boyer. "Anthrax" *Interactive Concepts in Biochemistry* © 2002, John Wiley & Sons Publishers, Inc. <http://www.wiley.com/legacy/college/boyer/0470003790/cutting_edge/anthrax/anthrax.htm> Dated visited Jan. 7, 2005.
Mosier, Donald E. et al. "Transfer of a functional human immune system to mice with severe combined immunodeficiency." *Nature*, vol. 335 (Sep. 15, 1988): 256-259.
Maynard, Jennifer A. et al. "Protection against anthrax toxin by recombinant antibody fragments correlates with antigen affinity." *Nature Biotechnology*. vol. 20 (2002): 597-601.
Turnbull, Peter C. B. et al. "Development of Antibodies to Protective Antigen and Lethal Factor Components of Anthrax Toxin in Humans and Guineas Pigs and Their Relevance to Protective immunity." *Infection and Immunity*, vol. 52, No. 2 (May 1986): 356-363.
Welkos, SL et al. "Sequence and analysis of the DNA encoding protective antigen of *Bacillus anthracix*." *Gene*, vol. 69, No. 2 (1988): 287-300. (Abstract).
Novak, Jeanne M. Novak et al. "Functional Characterization of Protease-treated *Bacillus anthracis* Protective Antigen." *The Journal of Biological Chemistry*, vol. 267, No. 24 (1992): 17186-17193.
Wild et al. "Human antibodies from immunized donors are protective against anthrax toxin in vivo." *Nature Biotechnology*. vol. 21, No. 11 (Oct. 2003): 1305-1306.
Cirino et al. "Disruption of Anthrax Toxin Binding with the Use of Human Antibodies and Competitive Inhibitors." *Infection and Immunity*. vol. 67, No. (Jun. 1999): 2957-2963.
Zolla-Panzer, S. Human Monoclonal Antitoxin to Anthrax Protective Antigen. NLM Doc. No. CRISP/2002/AI53306-01. Pub. Year (as listed): 2002.
Morrow, P.R. "Diverse mix of Human MoAbs to treat Anthrax exposure." NLM Doc. No. CRISP/2002/AI052901-01A1. Pub. Year (as listed): 2003.
Written Opinion of the International Searching Authority of PCT Application No. PCT/US05/01574, filed Jan. 21, 2005.
Physicians' Desk Reference (Edition 55, 2001 pp. 816-818 and 871-876).
Little et al. (Infection and Immunity, 65:12 5171-5175, Dec. 1997).
Brams et al. Antigen-Specific IgG Responses for Naïve Human Splenocytes: In Vitro Priming Followed by the Antigen Boost in the SCID Mouse. The Journal of Immunology. 1998, vol. 160, pp. 2051-2058 (entire document).
Little, et al. "Production and Characterization of Monoclonal Antibodies to the Protective Antigen Component of *Bacillus anthracis* Toxin." infection and Immunity, Jul. 1988. 56:7, 1807-1813.
Peterson, et al. "Human Monoclonal Antibody AVP-21D9 to Protective Antigen Reduces Dissemination of the *Bacillus anthracis* Ames Strain from the Lungs in a Rabbit Model." Infection and Immunity, Jul. 2007. 75:7, 3414-3424.
Peterson, et al. "Human Monoclonal Anti-Protective Antigen Antibody Completely Protects Rabbits and Is Synergistic with Ciprofloxacin in Protecting Mice and Guinea Pigs against Inhalation Anthrax." Infection and Immunity, Feb. 2006. 74:2, 1016-1024.

* cited by examiner

FIG. 3

21D9 Mab heavy chain variable region cDNA and the deduced amino acid sequence

```
       Q   V   Q   L   Q   Q   S   G   G   A   V   V   Q   P   G   G   S   L   R   L
  1    CAGGTACAGC TGCAGCAGTC TGGGGGAGCC GTGGTGCAGC CTGGGGGGTC CCTCAGACTC
                                              CDR1
       S   C   A   A   S   G   F   T   L   D   D   Y   A   M   H   W   V   R   Q   V
 61    TCCTGTGCAG CCTCTGGATT CACGCTTGAT GATTATGCCA TGCACTGGGT CCGACAAGTT
                                                        CDR2
       S   G   K   G   L   E   W   V   C   L   V   S   W   D   G   H   A   T   H   Y
121    TCGGGGAAGG GTCTGGAGTG GGTCTGCCTT GTCAGTTGGG ATGGTCATGC CACCCACTAT

A   D   S   V   K   G   R   F   T   I   S   R   D   N   S   R   N   S   L   F
181    GCAGACTCTG TGAAGGGTCG ATTCACCATC TCCAGAGACA ACAGCAGAAA CTCCCTGTTT

L   Q   M   D   G   L   R   P   E   D   T   A   L   Y   Y   C   V   K   A   F
241    CTGCAAATGG ACGGTCTGAG ACCTGAGGAC ACCGCCTTGT ATTACTGTGT AAAAGCATTT
                          CDR3
       S   S   G   W   S   D   A   F   H   F   W   G   Q   G   T   L   V   T   V   S
301    AGTAGTGGCT GGTCTGATGC TTTTCACTTC TGGGGCCAGG GAACCCTGGT CACCGTCTCC

S
361    TCA
```

FIG. 5

21D9 Mab light chain variable region cDNA and the deduced amino acid sequence

```
        E   I   V   L   T   Q   S   P   S   T   L   S   A   S   V   G   D   R   V   I
1       GAAATTGTGT TGACVCAGTC TCCTTCCACC CTGTCTGCGT CTGTAGGGGA CAGAGTCATT
                                            CDR1
        I   T   C   R   A   S   Q   R   I   R   N   E   L   A   W   Y   Q   Q   K   P
61      ATCACTTGCC GGGCCAGTCA GAGGATTCGT AACGAGTTGG CCTGGTATCA GCAGAAACCA
                                                      CDR2
        G   K   A   P   K   V   L   I   Y   K   A   S   T   L   E   S   G   V   P   S
121     GGGAAAGCCC CTAAAGTCCT GATCTATAAG GCGTCTACTT TAGAAAGTGG GGTCCCATCA

R   F   S   G   S   G   S   G   T   E   F   T   L   T   I   S   S   L   Q   P
181     AGGTTCAGCG GCAGTGGATC TGGGACAGAA TTCACTCTCA CCATCAGCAG CCTGCAGCCT
                                                        CDR3
        D   D   F   A   T   Y   Y   C   Q   Q   Y   S   G   L   W   T   F   G   Q   G
241     GATGATTTTG CAACTTATTA CTGCCAACAA TATAGTGGTT TGTGGACGTT CGGCCAGGGG

T   K   L   E   I   K
301     ACCAAGCTGG AAATCAAA
```

```
          Q   V   Q   L   Q   Q   S   G   G   G   L   V   Q   P   G   G   S   L   K   L
  1   CAGGTACAGC TGCAGCAGTC TGGGGGAGGC TTGGTCCAGC CTGGGGGGTC CCTCAAACTC

S   C   A   A   S   G   F   T   F   S   D   S   A   I   H   W   V   R   Q   A
 61   TCCTGTGCAG CCTCTGGGTT CACCTTCAGT GACTCTGCTA TTCACTGGGT CCGCCAGGCT

S   G   K   G   L   E   W   V   G   R   I   R   S   K   A   N   G   Y   A   T
121   TCCGGGAAAG GGCTGGAGTG GGTTGGCCGT ATTAGAAGCA AAGCTAACGG TTACGCGACA

A   Y   T   A   S   V   K   G   R   F   T   I   S   R   D   D   S   L   N   T
181   GCATATACTG CGTCGGTGAA AGGCAGGTTC ACCATCTCCA GAGATGATTC ACTGAACACG

A   Y   L   Q   M   N   S   L   K   T   E   D   T   A   V   Y   Y   C   T   R
241   GCGTATCTGC AAATGAACAG CCTGAAAACC GAGGACACGG CCGTGTATTA CTGCACTAGA

H   D   S   T   T   W   F   L   R   D   V   F   D   I   W   G   Q   G   T   K
301   CACGATAGCA CCACCTGGTT CTTGAGAGAT GTTTTTGATA TCTGGGGCCA AGGGACAAAG

V   T   V   S   S
361   GTTACCGTCT CTTCA
```

1C6 VK

```
          D   I   Q   V   T   Q   S   P   S   S   L   S   A   S   V   G   D   R   V   T
  1   GACATCCAGG TGACCCAGTC TCCATCCTCC CTGTCTGCAT CTGTCGGAGA CAGAGTCACC

I   T   C   R   A   S   Q   G   I   D   R   A   L   A   W   Y   Q   Q   K   S
 61   ATCACTTGCC GGGCAAGTCA GGGCATTGAC AGAGCTTTAG CCTGGTATCA GCAGAAATCA

G   R   P   P   K   L   L   I   Y   D   A   S   S   L   E   S   G   V   P   S
121   GGTAGACCTC CTAAGCTCCT GATCTATGAT GCCTCCAGTT TAGAAAGTGG GGTCCCATCG

R   F   S   G   S   G   S   G   T   D   F   T   L   T   I   S   S   L   Q   P
181   AGGTTCAGCG GCAGTGGATC TGGGACAGAT TTCACTCTCA CCATCAGCAG CCTGCAGCCT

E   D   F   A   T   Y   Y   C   Q   Q   Y   K   S   Y   L   R   E   L   T   F
241   GAAGATTTTG CGACTTATTA CTGTCAACAG TATAAAAGCT ACCTTCGAGA GCTCACTTTC

G   G   G   T   K   V   E   I   K
301   GGCGGAGGGA CCAAGGTGGA GATCAAA
```

```
         Q   V   Q   L   L   E   S   G   P   G   L   V   K   P   S   E   T   L   S   L
  1    CAAGTGCAGC TGTTGGAGTC TGGCCCAGGA CTGGTGAAGC CTTCGGAGAC CCTGTCCCTC

T   C   T   V   S   G   A   S   I   S   T   K   S   Y   S   W   G   W   I   R
 61    ACCTGCACTG TCTCTGGTGC CTCCATCAGC ACTAAGAGTT ATTCCTGGGG CTGGATCCGC

Q   P   P   G   K   G   L   E   W   I   G   I   A   Y   N   S   G   R   T   Y
121    CAGCCCCCAG GGAAGGGGCT GGAATGGATT GGTATCGCCT ACAATAGTGG GCGCACCTAC

F   N   P   S   L   K   S   R   V   T   I   S   V   D   T   S   K   N   R   F
181    TTCAATCCGT CCCTCAAGAG TCGAGTCACC ATATCCGTGG ACACGTCCAA GAACCGCTTC

S   L   Q   L   T   S   V   T   A   A   D   T   S   A   Y   F   C   V   S   S
241    TCCCTGCAAC TTACCTCTGT GACCGCCGCA GACACGTCTG CATATTTCTG TGTGAGTAGT

R   I   T   T   F   G   V   V   T   H   Y   G   M   D   V   W   G   R   G   T
301    CGTATTACAA CATTCGGAGT GGTCACTCAT TACGGTATGG ACGTCTGGGG CCGAGGGACC

T   V   T   V   S   S
361    ACGGTCACCG TCTCCTCA
```

4H7 VL

```
         Q   S   V   L   T   Q   P   P   S   V   S   V   A   P   G   T   T   A   R   I
  1    CAGTCTGTGT TGACGCAGCC GCCCTCGGTG TCAGTGGCCC CAGGAACGAC GGCCAGAATT

T   C   A   G   N   N   F   A   S   K   N   V   H   W   Y   Q   Q   K   P   G
 61    ACCTGTGCGG GGAACAACTT TGCAAGTAAA AATGTGCACT GGTATCAGCA GAAGCCAGGC

Q   A   P   V   L   V   V   S   A   D   S   D   R   P   S   E   I   P   E   R
121    CAGGCCCCTG TGCTGGTCGT CTCTGCTGAT AGCGACCGGC CCTCCGAAAT CCCTGAGCGA

F   S   A   S   S   T   G   N   T   A   T   L   T   I   S   R   V   D   A   G
181    TTTTCTGCCT CCAGCACTGG GAACACGGCC ACACTGACCA TCAGCAGGGT CGACGCCGGG

D   E   A   D   Y   Y   C   Q   V   W   D   S   S   R   D   D   R   F   V   V
241    GATGAGGCCG ACTATTATTG TCAGGTTTGG GACAGTAGTC GTGATGATCG TTTTGTGGTT

F   G   G   G   T   K   L   T   V   L   G
301    TTCGGCGGAG GCACCAAGCT GACCGTCCTA GGT
```

```
            Q  V  Q  L  Q  Q  S     G  G  G     L  V  K  P     G  G  S     L  R  L
  1         CAGGTACAGC TGCAGCAGTC TGGGGGAGGC TTGGTCAAGC CTGGAGGGTC CCTGAGACTC

S  C  T     A  S  G  F     I  F  S     D  Y  Y  M     S  W  I     R  Q  A
 61         TCCTGTACAG CCTCTGGATT CATCTTCAGT GACTACTATA TGAGTTGGAT CCGCCAGGCT

P  G  K  G     L  E  W     V  S  Y     M  K  N     S  D  G  S     K  Y  Y
121         CCAGGGAAGG GCCTGGAGTG GGTTTCATAC ATGAAAAATA GTGATGGTAG CAAATACTAC

A  D  S  V     K  G  R     F  T  I     S  R  D     N  A  K  N     S  L  Y
181         GCAGACTCTG TGAAGGGCCG GTTCACCATC TCCAGGGACA ACGCCAAGAA CTCATTGTAT

L  Q  M  N     S  L  R     A  G  D     T  A  V  Y     Y  C  V     R  D  L
241         CTGCAGATGA ACAGCCTGAG AGCCGGGGAC ACGGCTGTCT ATTACTGTGT GAGAGATCTT

D  Y  Y  D     R  S  G     Y  H  R     W  F  D  P     W  G  Q     G  T  L
301         GACTACTATG ATAGGAGTGG TTACCACCGG TGGTTCGACC CCTGGGGCCA GGGAACCCTG

V  T  V  S  S
361         GTCACCGTCT CCTCA
```

22G12 VL

```
            Q  S  V  L     T  Q  P     P  S  V     S  V  S  P     G  Q  T     A  S  I
  1         CAGTCTGTGT TGACGCAGCC GCCCTCAGTG TCCGTGTCCC CAGGACAGAC AGCCAGCATC

T  C  S  G     D  K  L     G  H  K     Y  A  C  W     Y  Q  Q     K  P  G
 61         ACCTGCTCTG GAGATAAATT GGGACATAAA TATGCTTGTT GGTATCAGCA GAAGCCAGGC

Q  S  P  V     L  V  I     Y  R  D     N  K  R  P     S  G  I     P  E  R
121         CAGTCCCCTG TACTGGTCAT CTATCGAGAT AACAAGCGGC CCTCAGGGAT CCCTGAGCGA

F  S  G  S     N  S  G     H  T  A     T  L  T  I     S  G  T     Q  A  L
181         TTCTCTGGCT CCAACTCTGG GCACACAGCC ACTCTGACCA TCAGCGGGAC CCAGGCTCTG

D  E  A  D     Y  Y  C     Q  A  W     D  S  S     T  H  V  I     F  G  G
241         GATGAGGCTG ACTATTACTG TCAGGCGTGG GACAGCAGCA CCCATGTGAT ATTCGGCGGA

G  T  K  L     T  V  L     G
301         GGCACCAAGC TGACCGTCCT AGGT
```

FIG. 10

**Effect of Glycosylation on Anti-PA Abs on
Protection of Rats from Lethal Toxin Challenge**
(Administration of Antibody at t = - 5min)

- ● AVP-21D9, 0.5x
- ○ AVP-21D9.1, 0.5x
- ■ AVP-22G12, 1x
- □ AVP-22G12.1, 1x
- △ IgG control, 0.5x
- ▽ IgG control, 1x

FIG. 12

Duration of Protection of Rats from Lethal Toxin Challenge with AVP-21D9

●— AVP-21D9, 1x
○-- IgG control, 1x    t = -17hrs

■— AVP-21D9, 10x
□-- IgG control, 10x   t = -1 week

FIG. 13

SEQUENCE LISTING

```
<160> NUMBER OF SEQ ID NOS: 58

<210> SEQ ID NO 1
<211> LENGTH: 363
<212> TYPE: DNA
<213> ORGANISM: Homo sapiens

<400> SEQUENCE: 1
caggtacagc tgcagcagtc tgggggagcc gtggtgcagc ctggggggtc cctcagactc      60
tcctgtgcag cctctggatt cacgcttgat gattatgcca tgcactgggt ccgacaagtt     120
tcggggaagg gtctggagtg ggtctgcctt gtcagttggg atggtcatgc cacccactat     180
gcagactctg tgaagggtcg attcaccatc tccagagaca acagcagaaa ctccctgttt     240
ctgcaaatgg acggtctgag acctgaggac accgccttgt attactgtgt aaaagcattt     300
agtagtggct ggtctgatgc ttttcacttc tggggccagg gaaccctggt caccgtctcc     360
tca                                                                   363

<210> SEQ ID NO 2
<211> LENGTH: 121
<212> TYPE: PRT
<213> ORGANISM: Homo sapiens

<400> SEQUENCE: 2

Gln Val Gln Leu Gln Gln Ser Gly Gly Ala Val Val Gln Pro Gly Gly
 1               5                  10                  15

Ser Leu Arg Leu Ser Cys Ala Ala Ser Gly Phe Thr Leu Asp Asp Tyr
            20                  25                  30

Ala Met His Trp Val Arg Gln Val Ser Gly Lys Gly Leu Glu Trp Val
        35                  40                  45

Cys Leu Val Ser Trp Asp Gly His Ala Thr His Tyr Ala Asp Ser Val
    50                  55                  60

Lys Gly Arg Phe Thr Ile Ser Arg Asp Asn Ser Arg Asn Ser Leu Phe
65                  70                  75                  80
```

Leu Gln Met Asp Gly Leu Arg Pro Glu Asp Thr Ala Leu Tyr Tyr Cys
                85                  90                  95

Val Lys Ala Phe Ser Ser Gly Trp Ser Asp Ala Phe His Phe Trp Gly
            100                 105                 110

Gln Gly Thr Leu Val Thr Val Ser Ser
        115                 120

<210> SEQ ID NO 3
<211> LENGTH: 318
<212> TYPE: DNA
<213> ORGANISM: Homo sapiens

<400> SEQUENCE: 3
gaaattgtgt tgacvcagtc tccttccacc ctgtctgcgt ctgtagggga cagagtcatt        60
atcacttgcc gggccagtca gaggattcgt aacgagttgg cctggtatca gcagaaacca       120
gggaaagccc ctaaagtcct gatctataag gcgtctactt tagaaagtgg ggtcccatca       180
aggttcagcg gcagtggatc tgggacagaa ttcactctca ccatcagcag cctgcagcct       240
gatgattttg caacttatta ctgccaacaa tatagtggtt tgtggacgtt cggccagggg       300
accaagctgg aaatcaaa                                                    318

<210> SEQ ID NO 4
<211> LENGTH: 106
<212> TYPE: PRT
<213> ORGANISM: Homo sapiens

<400> SEQUENCE: 4

Glu Ile Val Leu Thr Gln Ser Pro Ser Thr Leu Ser Ala Ser Val Gly
1               5                   10                  15

Asp Arg Val Ile Ile Thr Cys Arg Ala Ser Gln Arg Ile Arg Asn Glu
            20                  25                  30

Leu Ala Trp Tyr Gln Gln Lys Pro Gly Lys Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Gly Leu Trp Thr
                85                  90                  95

Phe Gly Gln Gly Thr Lys Leu Glu Ile Lys
            100                 105

<210> SEQ ID NO 5
<211> LENGTH: 375
<212> TYPE: DNA
<213> ORGANISM: Homo sapiens

<400> SEQUENCE: 5
caggtacagc tgcagcagtc tgggggaggc ttggtccagc ctgggggtc cctcaaactc         60 tcctgtgcag cctctgggtt caccttcagt gactctgcta ttcactgggt ccgccaggct       120
tccgggaaag gctgagtg gttggccgt attagaagca agctaacgg ttacgcgaca           180 gcatatactg cgtcggtgaa aggcaggttc accatctcca gagatgattc actgaacacg       240
gcgtatctgc aaatgaacag cctgaaaacc gaggacacgg ccgtgtatta ctgcactaga       300
cacgatagca ccacctggtt cttgagagat gtttttgata tctggggcca agggacaaag       360
gttaccgtct cttca                                                                375

<210> SEQ ID NO 6
<211> LENGTH: 125
<212> TYPE: PRT
<213> ORGANISM: Homo sapiens

<400> SEQUENCE: 6

Gln Val Gln Leu Gln Gln Ser Gly Gly Gly Leu Val Gln Pro Gly Gly
 1               5                  10                  15

Ser Leu Lys Leu Ser Cys Ala Ala Ser Gly Phe Thr Phe Ser Asp Ser
            20                  25                  30

Ala Ile His Trp Val Arg Gln Ala Ser Gly Lys Gly Leu Glu Trp Val
        35                  40                  45

Gly Arg Ile Arg Ser Lys Ala Asn Gly Tyr Ala Thr Ala Tyr Thr Ala
    50                  55                  60

Ser Val Lys Gly Arg Phe Thr Ile Ser Arg Asp Asp Ser Leu Asn Thr
65                  70                  75                  80

Ala Tyr Leu Gln Met Asn Ser Leu Lys Thr Glu Asp Thr Ala Val Tyr
                85                  90                  95

Tyr Cys Thr Arg His Asp Ser Thr Thr Trp Phe Leu Arg Asp Val Phe
           100                 105                 110

Asp Ile Trp Gly Gln Gly Thr Lys Val Thr Val Ser Ser
       115                 120                 125

<210> SEQ ID NO 7
<211> LENGTH: 327
<212> TYPE: DNA
<213> ORGANISM: Homo sapiens

<400> SEQUENCE: 7
gacatccagg tgacccagtc tccatcctcc ctgtctgcat ctgtcggaga cagagtcacc      60
atcacttgcc gggcaagtca gggcattgac agagctttag cctggtatca gcagaaatca     120 ggtagaccte ctaagctcct gatctatgat gcctccagtt tagaaagtgg ggtcccatcg     180
aggttcagcg gcagtggatc tgggacagat ttcactctca ccatcagcag cctgcagcct     240
gaagattttg cgacttatta ctgtcaacag tataaaagct accttcgaga gctcactttc     300
ggcggaggga ccaaggtgga gatcaaa                                         327

<210> SEQ ID NO 8
<211> LENGTH: 109
<212> TYPE: PRT
<213> ORGANISM: Homo sapiens

<400> SEQUENCE: 8

Asp Ile Gln Val Thr Gln Ser Pro Ser Ser Leu Ser Ala Ser Val Gly
 1               5                  10                  15

Asp Arg Val Thr Ile Thr Cys Arg Ala Ser Gln Gly Ile Asp Arg Ala
            20                  25                  30

Leu Ala Trp Tyr Gln Gln Lys Ser Gly Arg Pro Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Ser Tyr Leu Arg
                85                  90                  95

```
Glu Leu Thr Phe Gly Gly Gly Thr Lys Val Glu Ile Lys
            100                 105
```

<210> SEQ ID NO 9
<211> LENGTH: 378
<212> TYPE: DNA
<213> ORGANISM: Homo sapiens

<400> SEQUENCE: 9

```
caagtgcagc tgttggagtc tggcccagga ctggtgaagc cttcggagac cctgtccctc    60
acctgcactg tctctggtgc ctccatcagc actaagagtt attcctgggg ctggatccgc   120
cagcccccag ggaaggggct ggaatggatt ggtatcgcct acaatagtgg gcgcacctac   180
ttcaatccgt ccctcaagag tcgagtcacc atatccgtgg acacgtccaa gaaccgcttc   240
tccctgcaac ttacctctgt gaccgccgca gacacgtctg catatttctg tgtgagtagt   300
cgtattacaa cattcggagt ggtcactcat tacggtatgg acgtctgggg ccgagggacc   360
acggtcaccg tctcctca                                                  378
```

<210> SEQ ID NO 10
<211> LENGTH: 126
<212> TYPE: PRT
<213> ORGANISM: Homo sapiens

<400> SEQUENCE: 10

```
Gln Val Gln Leu Leu Glu Ser Gly Pro Gly Leu Val Lys Pro Ser Glu
 1               5                  10                  15
Thr Leu Ser Leu Thr Cys Thr Val Ser Gly Ala Ser Ile Ser Thr Lys
            20                  25                  30
Ser Tyr Ser Trp Gly Trp Ile Arg Gln Pro Pro Gly Lys Gly Leu Glu
        35                  40                  45
Trp Ile Gly Ile Ala Tyr Asn Ser Gly Arg Thr Tyr Phe Asn Pro Ser
    50                  55                  60
Leu Lys Ser Arg Val Thr Ile Ser Val Asp Thr Ser Lys Asn Arg Phe
65                  70                  75                  80
Ser Leu Gln Leu Thr Ser Val Thr Ala Ala Asp Thr Ser Ala Tyr Phe
                85                  90                  95
Cys Val Ser Ser Arg Ile Thr Thr Phe Gly Val Val Thr His Tyr Gly
            100                 105                 110
Met Asp Val Trp Gly Arg Gly Thr Thr Val Thr Val Ser Ser
        115                 120                 125
```

<210> SEQ ID NO 11
<211> LENGTH: 333
<212> TYPE: DNA
<213> ORGANISM: Homo sapiens

<400> SEQUENCE: 11

```
cagtctgtgt tgacgcagcc gccctcggtg tcagtggccc aggaacgac ggccagaatt      60
acctgtgcgg ggacaacctt tgcaagtaaa aatgtgcact ggtatcagca gaagccaggc   120
caggcccctg tgctggtcgt ctctgctgat agcgaccggc cctccgaaat ccctgagcga   180
ttttctgcct ccagcactgg gaacacggcc acactgacca tcagcagggt cgacgccggg   240
gatgaggccg actattattg tcaggtttgg gacagtagtc gtgatgatcg ttttgtggtt   300
tcggcggag gcaccaagct gaccgtccta ggt                                  333
```

<210> SEQ ID NO 12
<211> LENGTH: 111
<212> TYPE: PRT
<213> ORGANISM: Homo sapiens

<400> SEQUENCE: 12

Gln Ser Val Leu Thr Gln Pro Pro Ser Val Ser Val Ala Pro Gly Thr
1               5                   10                  15

Thr Ala Arg Ile Thr Cys Ala Gly Asn Asn Phe Ala Ser Lys Asn Val
            20                  25                  30

His Trp Tyr Gln Gln Lys Pro Gly Gln Ala Pro Val Leu Val Val Ser
        35                  40                  45

Ala Asp Ser Asp Arg Pro Ser Glu Ile Pro Glu Arg Phe Ser Ala Ser
    50                  55                  60

Ser Thr Gly Asn Thr Ala Thr Leu Thr Ile Ser Arg Val Asp Ala Gly
65                  70                  75                  80

Asp Glu Ala Asp Tyr Tyr Cys Gln Val Trp Asp Ser Ser Arg Asp Asp
                85                  90                  95

Arg Phe Val Val Phe Gly Gly Gly Thr Lys Leu Thr Val Leu Gly
            100                 105                 110

<210> SEQ ID NO 13
<211> LENGTH: 375
<212> TYPE: DNA
<213> ORGANISM: Homo sapiens

<400> SEQUENCE: 13
caggtacagc tgcagcagtc tgggggaggc ttggtcaagc ctggagggtc cctgagactc      60
tcctgtacag cctctggatt catcttcagt gactactata tgagttggat ccgccaggct     120
ccagggaagg gcctggagtg gtttcatac atgaaaaata gtgatggtag caaatactac     180
gcagactctg tgaagggccg gttcaccatc tccagggaca cgccaagaa ctcattgtat     240 ctgcagatga acagcctgag agccggggac acggctgtct attactgtgt gagagatctt     300
gactactatg ataggagtgg ttaccaccgg tggttcgacc cctggggcca gggaaccctg     360
gtcaccgtct cctca                                                      375

<210> SEQ ID NO 14
<211> LENGTH: 125
<212> TYPE: PRT
<213> ORGANISM: Homo sapiens

<400> SEQUENCE: 14

Gln Val Gln Leu Gln Gln Ser Gly Gly Gly Leu Val Lys Pro Gly Gly
1               5                   10                  15

Ser Leu Arg Leu Ser Cys Thr Ala Ser Gly Phe Ile Phe Ser Asp Tyr
            20                  25                  30

Tyr Met Ser Trp Ile Arg Gln Ala Pro Gly Lys Gly Leu Glu Trp Val
        35                  40                  45

Ser Tyr Met Lys Asn Ser Asp Gly Ser Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Gly Asp Thr Ala Val Tyr Tyr Cys
                85                  90                  95

Val Arg Asp Leu Asp Tyr Tyr Asp Arg Ser Gly Tyr His Arg Trp Phe
            100                 105                 110

Asp Pro Trp Gly Gln Gly Thr Leu Val Thr Val Ser Ser
        115                 120                 125

<210> SEQ ID NO 15
<211> LENGTH: 324
<212> TYPE: DNA
<213> ORGANISM: Homo sapiens

<400> SEQUENCE: 15
cagtctgtgt tgacgcagcc gccctcagtg tccgtgtccc caggacagac agccagcatc    60
acctgctctg gagataaatt gggacataaa tatgcttgtt ggtatcagca gaagccaggc   120
cagtcccctg tactggtcat ctatcgagat aacaagcggc cctcagggat ccctgagcga   180
ttctctggct ccaactctgg gcacacagcc actctgacca tcagcgggac ccaggctctg   240
gatgaggctg actattactg tcaggcgtgg gacagcagca cccatgtgat attcggcgga   300
ggcaccaagc tgaccgtcct aggt                                          324

<210> SEQ ID NO 16
<211> LENGTH: 108
<212> TYPE: PRT
<213> ORGANISM: Homo sapiens

<400> SEQUENCE: 16

Gln Ser Val Leu Thr Gln Pro Pro Ser Val Ser Val Ser Pro Gly Gln
  1               5                  10                  15

Thr Ala Ser Ile Thr Cys Ser Gly Asp Lys Leu Gly His Lys Tyr Ala
             20                  25                  30

Cys Trp Tyr Gln Gln Lys Pro Gly Gln Ser Pro Val Leu Val Ile Tyr
         35                  40                  45

Arg Asp Asn Lys Arg Pro Ser Gly Ile Pro Glu Arg Phe Ser Gly Ser
     50                  55                  60

Asn Ser Gly His Thr Ala Thr Leu Thr Ile Ser Gly Thr Gln Ala Leu
 65                  70                  75                  80

Asp Glu Ala Asp Tyr Tyr Cys Gln Ala Trp Asp Ser Ser Thr His Val
                 85                  90                  95

Ile Phe Gly Gly Gly Thr Lys Leu Thr Val Leu Gly
            100                 105

<210> SEQ ID NO 17
<211> LENGTH: 21
<212> TYPE: DNA
<213> ORGANISM: Artificial Sequence
<220> FEATURE:
<223> OTHER INFORMATION: Chemically synthesized primer CVH2

<400> SEQUENCE: 17
tgccagrtca ccttgargga g                                              21

<210> SEQ ID NO 18
<211> LENGTH: 21
<212> TYPE: DNA
<213> ORGANISM: Artificial Sequence
<220> FEATURE:
<223> OTHER INFORMATION: Chemically synthesized primer CVH3

<400> SEQUENCE: 18
tgcsargtgc agctgktgga g                                              21

<210> SEQ ID NO 19
<211> LENGTH: 21

```
<212> TYPE: DNA
<213> ORGANISM: Artificial Sequence
<220> FEATURE:
<223> OTHER INFORMATION: Chemically synthesized primer CVH4

<400> SEQUENCE: 19
tgccagstgc agctrcagsa g                                              21

<210> SEQ ID NO 20
<211> LENGTH: 21
<212> TYPE: DNA
<213> ORGANISM: Artificial Sequence
<220> FEATURE:
<223> OTHER INFORMATION: Chemically synthesized primer CVH6

<400> SEQUENCE: 20
tgccaggtac agctgcagca g                                              21

<210> SEQ ID NO 21
<211> LENGTH: 23
<212> TYPE: DNA
<213> ORGANISM: Artificial Sequence
<220> FEATURE:
<223> OTHER INFORMATION: Chemically synthesized primer CVH1257

<400> SEQUENCE: 21
tgccaggtgc agctggtgsa rtc                                            23

<210> SEQ ID NO 22
<211> LENGTH: 19
<212> TYPE: DNA
<213> ORGANISM: Artificial Sequence
<220> FEATURE:
<223> OTHER INFORMATION: Chemically synthesized primer C-gamma II

<400> SEQUENCE: 22
gccaggggga agacsgatg                                                 19

<210> SEQ ID NO 23
<211> LENGTH: 23
<212> TYPE: DNA
<213> ORGANISM: Artificial Sequence
<220> FEATURE:
<223> OTHER INFORMATION: Chemically synthesized primer VK1F

<400> SEQUENCE: 23
gacatccrgd tgacccagtc tcc                                            23

<210> SEQ ID NO 24
<211> LENGTH: 23
<212> TYPE: DNA
<213> ORGANISM: Artificial Sequence
<220> FEATURE:
<223> OTHER INFORMATION: Chemically synthesized primer VK36F

<400> SEQUENCE: 24
gaaattgtrw tgacrcagtc tcc                                            23

<210> SEQ ID NO 25
<211> LENGTH: 23
<212> TYPE: DNA
<213> ORGANISM: Artificial Sequence
<220> FEATURE:
<223> OTHER INFORMATION: Chemically synthesized primer VK2346F

<400> SEQUENCE: 25
```
gatrttgtgm tgacbcagwc tcc                                          23

<210> SEQ ID NO 26
<211> LENGTH: 22
<212> TYPE: DNA
<213> ORGANISM: Artificial Sequence
<220> FEATURE:
<223> OTHER INFORMATION: Chemically synthesized primer VK5F

<400> SEQUENCE: 26
gaaacgacac tcacgcagtc tc                                           22

<210> SEQ ID NO 27
<211> LENGTH: 24
<212> TYPE: DNA
<213> ORGANISM: Artificial Sequence
<220> FEATURE:
<223> OTHER INFORMATION: Chemically synthesized primer Ck543

<400> SEQUENCE: 27
gtttctcgta gtctgctttg ctca                                         24

<210> SEQ ID NO 28
<211> LENGTH: 23
<212> TYPE: DNA
<213> ORGANISM: Artificial Sequence
<220> FEATURE:
<223> OTHER INFORMATION: Chemically synthesized primer VL1

<400> SEQUENCE: 28
cagtctgtgy tgacgcagcc gcc                                          23

<210> SEQ ID NO 29
<211> LENGTH: 21
<212> TYPE: DNA
<213> ORGANISM: Artificial Sequence
<220> FEATURE:
<223> OTHER INFORMATION: Chemically synthesized primer VL2

<400> SEQUENCE: 29
cagtctgyyc tgaytcagcc t                                            21

<210> SEQ ID NO 30
<211> LENGTH: 23
<212> TYPE: DNA
<213> ORGANISM: Artificial Sequence
<220> FEATURE:
<223> OTHER INFORMATION: Chemically synthesized primer VL3

<400> SEQUENCE: 30
tcctatgagc tgayrcagcy acc                                          23

<210> SEQ ID NO 31
<211> LENGTH: 20
<212> TYPE: DNA
<213> ORGANISM: Artificial Sequence
<220> FEATURE:
<223> OTHER INFORMATION: Chemically synthesized primer VL1459

<400> SEQUENCE: 31
cagcctgtgc tgactcaryc                                              20

<210> SEQ ID NO 32
<211> LENGTH: 23
<212> TYPE: DNA
<213> ORGANISM: Artificial Sequence

```
<220> FEATURE:
<223> OTHER INFORMATION: Chemically synthesized primer VL78

<400> SEQUENCE: 32
cagdctgtgg tgacycagga gcc                                          23

<210> SEQ ID NO 33
<211> LENGTH: 22
<212> TYPE: DNA
<213> ORGANISM: Artificial Sequence
<220> FEATURE:
<223> OTHER INFORMATION: Chemically synthesized primer VL6

<400> SEQUENCE: 33
aattttatgc tgactcagcc cc                                           22

<210> SEQ ID NO 34
<211> LENGTH: 20
<212> TYPE: DNA
<213> ORGANISM: Artificial Sequence
<220> FEATURE:
<223> OTHER INFORMATION: Chemically synthesized primer CL2

<400> SEQUENCE: 34
agctcctcag aggagggygg                                              20

<210> SEQ ID NO 35
<211> LENGTH: 32
<212> TYPE: DNA
<213> ORGANISM: Artificial Sequence
<220> FEATURE:
<223> OTHER INFORMATION: Chemically synthesized primer BsrGIVHF2

<400> SEQUENCE: 35
aaaatgtaca gtgccagrtc accttgargg ag                                32

<210> SEQ ID NO 36
<211> LENGTH: 32
<212> TYPE: DNA
<213> ORGANISM: Artificial Sequence
<220> FEATURE:
<223> OTHER INFORMATION: Chemically synthesized primer BsrGIVHF3

<400> SEQUENCE: 36
aaaatgtaca gtgcsargtg cagctgktgg ag                                32

<210> SEQ ID NO 37
<211> LENGTH: 32
<212> TYPE: DNA
<213> ORGANISM: Artificial Sequence
<220> FEATURE:
<223> OTHER INFORMATION: Chemically synthesized primer BsrGIVHF4

<400> SEQUENCE: 37
aaaatgtaca gtgccagstg cagctrcags ag                                32

<210> SEQ ID NO 38
<211> LENGTH: 32
<212> TYPE: DNA
<213> ORGANISM: Artificial Sequence
<220> FEATURE:
<223> OTHER INFORMATION: Chemically synthesized primer BsrGIVHF6

<400> SEQUENCE: 38
aaaatgtaca gtgccaggta cagctgcagc ag                                32
```

<210> SEQ ID NO 39
<211> LENGTH: 34
<212> TYPE: DNA
<213> ORGANISM: Artificial Sequence
<220> FEATURE:
<223> OTHER INFORMATION: Chemically synthesized primer BsrGIVHF1257

<400> SEQUENCE: 39
aaaatgtaca gtgccaggtg cagctggtgs artc                                34

<210> SEQ ID NO 40
<211> LENGTH: 21
<212> TYPE: DNA
<213> ORGANISM: Artificial Sequence
<220> FEATURE:
<223> OTHER INFORMATION: Chemically synthesized primer C gamma ER

<400> SEQUENCE: 40
gacsgatggg cccttggtgg a                                              21

<210> SEQ ID NO 41
<211> LENGTH: 35
<212> TYPE: DNA
<213> ORGANISM: Artificial Sequence
<220> FEATURE:
<223> OTHER INFORMATION: Chemically synthesized primer AgeIVK1F

<400> SEQUENCE: 41
ttttaccggt gtgacatccr gdtgacccag tctcc                               35

<210> SEQ ID NO 42
<211> LENGTH: 35
<212> TYPE: DNA
<213> ORGANISM: Artificial Sequence
<220> FEATURE:
<223> OTHER INFORMATION: Chemically synthesized primer AgeIVK36F

<400> SEQUENCE: 42
ttttaccggt gtgaaattgt rwtgacrcag tctcc                               35

<210> SEQ ID NO 43
<211> LENGTH: 35
<212> TYPE: DNA
<213> ORGANISM: Artificial Sequence
<220> FEATURE:
<223> OTHER INFORMATION: Chemically synthesized primer AgeIVK2346F

<400> SEQUENCE: 43
ttttaccggt gtgatrttgt gmtgacbcag wctcc                               35

<210> SEQ ID NO 44
<211> LENGTH: 34
<212> TYPE: DNA
<213> ORGANISM: Artificial Sequence
<220> FEATURE:
<223> OTHER INFORMATION: Chemically synthesized primer AgeIVK5F

<400> SEQUENCE: 44
ttttaccggt gtgaaacgac actcacgcag tctc                                34

<210> SEQ ID NO 45
<211> LENGTH: 33
<212> TYPE: DNA
<213> ORGANISM: Artificial Sequence
<220> FEATURE:
<223> OTHER INFORMATION: Chemically synthesized primer Sp1KFR4R12

<400> SEQUENCE: 45
tttcgtacgt ttgayytcca scttggtccc ytg                          33

<210> SEQ ID NO 46
<211> LENGTH: 33
<212> TYPE: DNA
<213> ORGANISM: Artificial Sequence
<220> FEATURE:
<223> OTHER INFORMATION: Chemically synthesized primer Sp1KFR4R3

<400> SEQUENCE: 46
tttcgtacgt ttsakatcca ctttggtccc agg                          33

<210> SEQ ID NO 47
<211> LENGTH: 33
<212> TYPE: DNA
<213> ORGANISM: Artificial Sequence
<220> FEATURE:
<223> OTHER INFORMATION: Chemically synthesized primer Sp1KFR4R4

<400> SEQUENCE: 47
tttcgtacgt ttgatctcca ccttggtccc tcc                          33

<210> SEQ ID NO 48
<211> LENGTH: 33
<212> TYPE: DNA
<213> ORGANISM: Artificial Sequence
<220> FEATURE:
<223> OTHER INFORMATION: Chemically synthesized primer Sp1KFR4R5

<400> SEQUENCE: 48
tttcgtacgt ttaatctcca gtcgtgtccc ttg                          33

<210> SEQ ID NO 49
<211> LENGTH: 32
<212> TYPE: DNA
<213> ORGANISM: Artificial Sequence
<220> FEATURE:
<223> OTHER INFORMATION: Chemically synthesized primer ApaIVL1

<400> SEQUENCE: 49
atatgggccc agtctgtgyt gacgcagccg cc                           32

<210> SEQ ID NO 50
<211> LENGTH: 30
<212> TYPE: DNA
<213> ORGANISM: Artificial Sequence
<220> FEATURE:
<223> OTHER INFORMATION: Chemically synthesized primer ApaIVL2

<400> SEQUENCE: 50
atatgggccc agtctgyyct gaytcagcct                              30

<210> SEQ ID NO 51
<211> LENGTH: 32
<212> TYPE: DNA
<213> ORGANISM: Artificial Sequence
<220> FEATURE:
<223> OTHER INFORMATION: Chemically synthesized primer ApaIVL3

<400> SEQUENCE: 51
atatgggccc agtatgagct gayrcagcya cc                           32

<210> SEQ ID NO 52

<211> LENGTH: 29
<212> TYPE: DNA
<213> ORGANISM: Artificial Sequence
<220> FEATURE:
<223> OTHER INFORMATION: Chemically synthesized primer ApaIVL1459

<400> SEQUENCE: 52
atatgggccc agcctgtgct gactcaryc                                29

<210> SEQ ID NO 53
<211> LENGTH: 32
<212> TYPE: DNA
<213> ORGANISM: Artificial Sequence
<220> FEATURE:
<223> OTHER INFORMATION: Chemically synthesized primer ApaIVL78

<400> SEQUENCE: 53
atatgggccc agdctgtggt gacycaggag cc                            32

<210> SEQ ID NO 54
<211> LENGTH: 32
<212> TYPE: DNA
<213> ORGANISM: Artificial Sequence
<220> FEATURE:
<223> OTHER INFORMATION: Chemically synthesized primer ApaIVL6

<400> SEQUENCE: 54
atatgggccc agttttatgc tgactcagcc cc                            32

<210> SEQ ID NO 55
<211> LENGTH: 29
<212> TYPE: DNA
<213> ORGANISM: Artificial Sequence
<220> FEATURE:
<223> OTHER INFORMATION: Chemically synthesized primer AvrIIVL1IR

<400> SEQUENCE: 55
tttcctagga cggtgacctt ggtcccagt                                29

<210> SEQ ID NO 56
<211> LENGTH: 33
<212> TYPE: DNA
<213> ORGANISM: Artificial Sequence
<220> FEATURE:
<223> OTHER INFORMATION: Chemically synthesized primer AvrIIVL237IR

<400> SEQUENCE: 56
tttcctagga cggtcagctt ggtscctcck ccg                           33

<210> SEQ ID NO 57
<211> LENGTH: 29
<212> TYPE: DNA
<213> ORGANISM: Artificial Sequence
<220> FEATURE:
<223> OTHER INFORMATION: Chemically synthesized primer AvrIIVL6IR

<400> SEQUENCE: 57
tttcctagga cggtcacctt ggtgccact                                29

<210> SEQ ID NO 58
<211> LENGTH: 29
<212> TYPE: DNA
<213> ORGANISM: Artificial Sequence
<220> FEATURE:
<223> OTHER INFORMATION: Chemically synthesized primer AvrIIVLmixIR

```
<400> SEQUENCE: 58
tttcctagga cggtcarctk ggtbcctcc                                              29
```

IMMUNIZATION AND TREATMENT METHODS FOR ANTHRAX

RELATED APPLICATIONS

This application is a continuation of U.S. application Ser. No. 11/040,580, filed Jan. 21, 2005, and is a continuation-in-part of PCT Application No. PCT/US2003/36555, filed Nov. 14, 2003 under 35 U.S.C. § 120, and also claims benefit to U.S. provisional applications Ser. No. 60/538,721, filed Jan. 23, 2004 and Ser. No. 60/562,421, filed Apr. 15, 2004, all herein incorporated by reference.

GOVERNMENT INTEREST

This invention was made, in part, with the support of the United States Government under the following grants: CCAT # 52109B 7806, NIAID # R43 AI52901-1A1, and NIAID # R43 AI 58458-01. The Government has certain rights in this invention.

BACKGROUND OF THE INVENTION

1. Field of the Invention

The present invention relates generally to fully human monoclonal antibodies, method of making same, and their use in preventive and therapeutic applications for anthrax. In one aspect, antibodies that have binding specificity for anthrax protective antigen (PA) toxin are provided.

2. Description of the Related Art

Anthrax is a zoonotic soil organism endemic to many parts of the world. The *Bacillus anthracis* organism was one of the first biological warfare agents to be developed and continues to be a major threat in this regard. The Centers for Disease Control and Prevention (CDC) has emphasized that the United States faces a new wave of terrorism, in the form of a biological attack. For example, in late 2001, *Bacillus anthracis* spores were intentionally distributed through the postal system, causing 22 cases of anthrax, including 5 deaths. Anthrax is a key toxin that can be employed by terrorists to debilitate a nation.

Although vaccine strains have been developed for anthrax, currently there are concerns regarding their efficacy and availability. After inhalation by mammals, *Bacillus anthracis* spores germinate in the alveolar macrophages, then migrate to lymph nodes where they multiply and enter the bloodstream. The vegetative bacteria excrete the tripartite exotoxin that is responsible for the etiology of the disease. Virulent strains of *Bacillus anthracis* secrete a set of three distinct antigenic protein components: protective antigen (PA), edema factor (EF), and lethal factor (LF). PA can bind either LF or EF, forming lethal toxin (LeTx) or edema toxin (EdTx). Collectively these two toxins are seen as a complex exotoxin called anthrax toxin. Each component of the toxin is a thermolabile protein with a molecular weight exceeding 80 kDa. EF is a calmodulin dependent adenylate cyclase that is responsible for the edema seen in anthrax infections. LF is a zinc-metalloprotease that is needed for the lethal effect of the anthrax toxin on macrophages. It is believed that PA contains the binding domain of anthrax toxin, which binds to recently identified receptors on the cell surface called collectively anthrax toxin receptors (ATRs) and allows translocation of LF or EF into the cell by endocytosis.

Evidence that the hu-PBL-SCID system (severe combined immunodeficient (SCID) mice engrafted with human peripheral blood leukocytes) can be used to obtain recall antibody responses dates from the original publication of the method by Mosier and co-workers. Mosier et al., *Nature* 335:256 (1988), herein incorporated by reference. In that report, tetanus toxoid was administered to human PBL engrafted mice, and human antibodies to tetanus were found in the serum post-immunization. Since this original report, many investigators have used the hu-PBL-SCID system to examine aspects of the human recall antibody response to multiple antigens. See, for example, Nonoyama, S. et al., *J. Immunol.*, 151:3894 (1993); Walker, W. et al., *Eur. J. Immunol.*, 25:1425 (1995); Else, K. J., and Betts. C. J., *Parasite Immunology* 19:485 (1997), all herein incorporated by reference. However, reports describing the generation of useful monoclonal antibodies from such engrafted mice have been sporadic. Duchosal, M. A. et al., *Letters To Nature:*258 (1991); Satoh, N. et al., *Immunology Letters* 47:113 (1995); Uchibayashi, N. et al., *Hybridoma* 14:313 (1995). Nguyen, H. et al., *Microbiol. Immunol.* 41:901 (1997); Coccia, M. A and P. Brams, *Amer. Assoc. Immunologists:*5772 (1998); and Smithson, S. L. et al., *Molecular Immunology* 36:113 (1999), all herein incorporated by reference.

SUMMARY OF THE INVENTION

There remains a need for an effective method to produce human monoclonal antibodies that are specific to a particular antigen. Moreover, a need for a fully human monoclonal antibody specific to the anthrax toxin still remains. Accordingly, in a preferred embodiment of the present invention, a novel anti-anthrax antibody that is fully human is provided. This new fully human anthrax antibody can be administered to a mammal to confer immunity to that mammal. Because the antibody is administered directly (instead of the antigen), this technique is called "passive immunization." Thus, in one embodiment of the present invention, a method of passively immunizing a mammal is provided using one or more novel antibodies of the invention. Several embodiments of the present invention are also used to treat mammals that have been exposed to anthrax, thereby preventing the toxic effects of anthrax post-exposure and/or reducing the severity of the illness.

In one embodiment of the present invention, a composition and method to counter the effects of anthrax toxin that is released as a mechanism of bioterrorism are provided. In one embodiment, a prophylactic treatment in the form of passive immunization is provided. In one embodiment, antibodies to anthrax are administered to a mammal to prevent anthrax infection and/or to treat anthrax infection. One advantage of a passive immunization strategy is that it may useful in conferring immediate to medium-term protection, and can also have benefits for non-immunized patients who seek treatment after the point at which antibiotic therapy alone is ineffective. Casadevall, A., *Emerging Infectious Diseases,* 8:8 (2002); Maynard, J. A et al., *Nature Biotechnology,* 20:597 (2002), herein incorporated by reference. Passive immunization, according to some embodiments of the invention, can confer short-term, long-term and/or permanent protection to recipients.

In some embodiments of the present invention, antibodies that bind to the PA component of the tripartite anthrax exotoxin are provided. These antibodies will provide protection either as single agents or combined in a cocktail. A method to generate a series of fully human anti-anthrax PA toxin antibodies is also provided.

In one embodiment, a fully human monoclonal antibody, or fragment thereof, is disclosed which specifically recognizes at least a portion of an anthrax exotoxin. In one variation, the portion of an anthrax exotoxin is selected from the group consisting of protective antigen (PA), lethal factor (LF) and edema factor (EF). In one embodiment, the antibody recognizes only PA.

In one embodiment, a fully human monoclonal antibody or fragment thereof that recognizes at least a portion of an anthrax exotoxin and comprises an amino acid sequence selected from the group consisting of: SEQ ID 2, SEQ ID 4, SEQ ID 6, SEQ ID 8, SEQ ID 10, SEQ ID 12, SEQ ID 14, and SEQ ID 16 is provided. In one embodiment, two or more antibodies are provided. In one embodiment, an antibody comprising SEQ ID 2 and SEQ 4 is provided. In another embodiment, an antibody comprising SEQ ID 6 and SEQ 8 is provided. In a further embodiment, an antibody comprising SEQ ID 2, SEQ 4, SEQ ID 6 and SEQ 8 is provided.

In one embodiment, a fully human monoclonal antibody encoded at least in part by a polynucleotide comprising a nucleotide sequence selected from the group consisting of: SEQ ID 1, SEQ ID 3, SEQ ID 5, SEQ ID 7, SEQ ID 9, SEQ ID 11, SEQ ID 13, and SEQ ID 15 is provided. In one embodiment, two or more antibodies are provided. In another embodiment, a hybridoma comprising one or more of the following nucleotide sequences: SEQ ID 1, SEQ ID 3, SEQ ID 5, SEQ ID 7, SEQ ID 9, SEQ ID 11, SEQ ID 13, and SEQ ID 15 is provided.

In one embodiment, one or more of the following antibodies, or fragments thereof, are provided: antibody 21D9, antibody 22G12, antibody 1C6, and antibody 4H7. In a preferred embodiment, two or three antibodies are provided. For example, in one embodiment, 21D9 and 1C6 are provided. In several embodiments, the administration of two or more antibodies shows enhanced or synergistic effects. Chemical modifications, mutations, and other variants of these antibodies are also provided, including but not limited to 21D9.1 and 22G12.1. Methods of making and using the antibodies, or fragments thereof, are also provided.

In a further embodiment, a pharmaceutical composition for passively immunizing a mammal against anthrax, wherein the pharmaceutical composition comprises one or more of the fully human monoclonal antibodies, or fragments thereof, described above, is provided. In one embodiment, the mammal has not been previously exposed to anthrax.

In one embodiment, a pharmaceutical composition for treating a mammal exposed to anthrax, wherein the pharmaceutical composition comprises one or more of the fully human monoclonal antibodies, or fragments thereof, described above, is provided.

In one embodiment, the pharmaceutical composition comprises two different fully human monoclonal antibodies, or fragments thereof. In some embodiments, the pharmaceutical composition comprises a monoclonal antibody that comprises less than 100% human protein sequences (for example, a humanized antibody or a partially human antibody). In a further embodiment, the pharmaceutical composition further comprises Anthrax Vaccine Adsorbed (AVA) or recombinant protective antigen (rPA). In one embodiment, the pharmaceutical composition comprises an antibiotic.

In another embodiment, the immunoglobulin or fragment thereof comprises an immunoglobulin heavy chain variable region comprising FR1, CDR1, FR2, CDR2, FR3, CDR3, and FR4; wherein the variable region is comprised of the amino acid sequence shown in FIG. 5. A "CDR" is a complementarity determining region. An "FR" is a frame work region. In one embodiment, an antibody comprising CDR1, CDR2, and CDR3 shown in SEQ ID 2 is provided.

In another embodiment, the immunoglobulin or fragment thereof comprises an immunoglobulin light chain variable region comprising FR1, CDR1, FR2, CDR2, FR3, CDR3, and FR4; wherein the variable region is comprised of the amino acid sequence shown in FIG. 6. In one embodiment, an antibody comprising heavy chain CDR1, CDR2, and CDR3, all as shown in FIG. 5, is provided. In another embodiment, an antibody comprising light chain CDR1, CDR2, and CDR3, all as shown in FIG. 6, is provided. In a preferred embodiment, an antibody comprising the heavy and light chain CDRs shown in FIG. 5 and FIG. 6 is provided.

In one preferred embodiment of the present invention, the fully human immunoglobulin or fragment thereof is a single chain that recognizes at least a portion of an anthrax exotoxin.

In one preferred embodiment, a fully human immunoglobulin or fragment thereof is disclosed, that recognizes at least a portion of an anthrax exotoxin, wherein the immunoglobulin or fragment thereof comprises an immunoglobulin heavy chain comprising at least a portion of the amino acid sequence shown in FIG. 8 and/or an immunoglobulin light chain comprising at least a portion of the amino acid sequence shown in FIG. 8. In one embodiment, the antibody comprises an immunoglobulin heavy chain comprising at least a portion of the amino acid sequence shown in FIG. 9 and/or an immunoglobulin light chain comprising at least a portion of the amino acid sequence shown in FIG. 9. In one embodiment, the antibody comprises an immunoglobulin heavy chain comprising at least a portion of the amino acid sequence shown in FIG. 10 and/or an immunoglobulin light chain comprising at least a portion of the amino acid sequence shown in FIG. 10.

In one preferred embodiment, a fully human immunoglobulin or fragment thereof is disclosed, that recognizes at least a portion of an anthrax exotoxin, wherein the immunoglobulin or fragment thereof comprises an immunoglobulin light chain comprising at least one complementary determining region selected from the group consisting of CDR1, CDR2 and CDR3; wherein the CDR1 is comprised of the amino acid sequence, as shown in FIG. 6; the CDR2 is comprised of the amino acid sequence, as shown in FIG. 6; and the CDR3 is comprised of the amino acid sequence, as shown in FIG. 6.

In another preferred embodiment, a fully human immunoglobulin or fragment thereof is disclosed, that recognizes at least a portion of an anthrax exotoxin, wherein the immunoglobulin or fragment thereof comprises an immunoglobulin heavy chain or light chain variable region comprising the amino acid sequence shown in FIG. 8.

In another preferred embodiment, a fully human immunoglobulin or fragment thereof is disclosed, that recognizes at least a portion of an anthrax exotoxin, wherein said immunoglobulin or fragment thereof comprises an immunoglobulin heavy chain or light chain variable region comprising the amino acid sequence shown in FIG. 9.

In another preferred embodiment, a fully human immunoglobulin or fragment thereof is disclosed, that recognizes at least a portion of an anthrax exotoxin, wherein said immunoglobulin or fragment thereof comprises an immunoglobulin heavy chain or light chain variable region comprising the amino acid sequence shown in FIG. 10.

In accordance with other embodiments of the invention the nucleotide sequences shown respectively in FIG. 5 and FIG. 6 are disclosed. These nucleotide sequences encode a heavy chain variable region and a light chain variable region, respectively, of a fully human immunoglobulin or fragment thereof, that recognizes at least a portion of an anthrax exotoxin.

In accordance with other embodiments of the invention, the nucleotide sequences shown in FIG. 8 are disclosed. These nucleotide sequences encode a heavy chain variable region and a light chain variable region, respectively, of a fully human immunoglobulin or fragment thereof, that recognizes at least a portion of an anthrax exotoxin.

In accordance with other embodiments of the invention, the nucleotide sequences shown in FIG. 9 are disclosed. These nucleotide sequences encode a heavy chain variable region and a light chain variable region, respectively, of a fully human immunoglobulin or fragment thereof, that recognizes at least a portion of an anthrax exotoxin.

In accordance with other embodiments of the invention, the nucleotide sequences shown in FIG. 10 are disclosed. These nucleotide sequences encode a heavy chain variable region and a light chain variable region, respectively, of a fully human immunoglobulin or fragment thereof, that recognizes at least a portion of an anthrax exotoxin.

In one embodiment of the invention, a method for passively immunizing a mammal is provided. In one embodiment, the method comprises administering an immunizing dose of one or more fully human monoclonal antibodies to a mammal, wherein said one or more fully human monoclonal antibodies comprise an amino acid sequence selected from the group consisting of: SEQ ID 2, SEQ ID 4, SEQ ID 6, SEQ ID 8, SEQ ID 10, SEQ ID 12, SEQ ID 14, and SEQ ID 16. In one embodiment, the mammal has not been exposed to anthrax. In another embodiment, the mammal has been exposed to anthrax, and the method is operable to immunize the mammal against the effects of subsequent exposures to anthrax.

In one embodiment of the invention, a method for treating a mammal that has been exposed to anthrax is provided. In one embodiment, the method comprises administering a therapeutic dose of one or more fully human monoclonal antibodies to a mammal, wherein said one or more fully human monoclonal antibodies comprise an amino acid sequence selected from the group consisting of: SEQ ID 2, SEQ ID 4, SEQ ID 6, SEQ ID 8, SEQ ID 10, SEQ ID 12, SEQ ID 14, and SEQ ID 16.

In one embodiment, the method comprises providing one or more antibiotics to the mammal. In another embodiment, one or more additional agents are also given to the mammal, wherein the agent comprises an antibody that contains less than 100% human protein sequences.

In one embodiment, at least two different antibodies are administered to a mammal. In one embodiment, the two antibodies differ by at least one amino acid. In one embodiment, the two antibodies are administered sequentially to said mammal (e.g., one antibody immediately after the other, or one antibody within minutes, hours, days, weeks, months etc after the other). In one embodiment, the two antibodies are administered simultaneously to said mammal. In another embodiment, the first antibody binds to at least one different epitope than the second antibody, thereby exerting a different mechanism of action. In one embodiment, both antibodies work by the same mechanism of action. In some embodiments, three or more antibodies are provided to a mammal. In preferred embodiments, one, two or three antibodies are administered for prevention and/or treatment of anthrax. One of skill in the art will understand that more than three antibodies can also be administered.

In one embodiment of the invention, the method comprises administering one or more additional therapeutic agents. Additional therapeutic agents include, but are not limited to, one or more vaccines (e.g., AVA and rPA), antibiotics (e.g., ciprofloxacin hydrochloride, doxycycline, and penicillin), and/or other antibodies. The additional therapeutic agents can be administered simultaneously or sequentially with said one or more fully human monoclonal antibodies. In one embodiment, an antibiotic and an antibody are administered shortly after anthrax exposure, followed by administration of a commercially-available vaccine, such as AVA or rPA. One advantage of such combination therapy is that immediate and long-term protection can be achieved.

In one embodiment of the present invention, a method of screening anthrax exotoxin in a sample is provided. In one embodiment, the method comprises contacting at least a portion of the sample with one or more fully human monoclonal antibodies comprise an amino acid sequence selected from the group consisting of: SEQ ID 2, SEQ ID 4, SEQ ID 6, SEQ ID 8, SEQ ID 10, SEQ ID 12, SEQ ID 14, and SEQ ID 16, and determining binding of anthrax exotoxin with said antibody. In one embodiment, the binding is an indicator of the presence anthrax in said sample, and the absence of binding is an indicator of the absence of anthrax in said sample.

In one embodiment of the present invention, a kit to determine the presence or absence of anthrax exotoxin in a sample is provided. The kit can be a compilation of materials, an article of manufacture, and/or a system of materials assembled for a common purpose. In one embodiment, the kit comprises one or more fully human monoclonal antibodies comprising an amino acid sequence selected from the group consisting of: SEQ ID 2, SEQ ID 4, SEQ ID 6, SEQ ID 8, SEQ ID 10, SEQ ID 12, SEQ ID 14, and SEQ ID 16. Two or more antibodies can be provided in the kit. In a further embodiment, the kit includes an assay to determine the reaction of anthrax exotoxin with said antibody, wherein said reaction is an indicator of the presence or absence of anthrax in said sample. Instructions regarding the use of the assay can also be included. The assay can be a binding test. An ELISA can also be used. In one embodiment, the kit is disposable.

In some embodiments, the kit or method described above is used detect anthrax in biological fluids, such as human serum, saliva, blood cells etc. In one embodiment, the sample is mammalian tissue. In another embodiment, the sample is inorganic or non-biological. In one embodiment, the kit and method will have utility in determining not just the presence, but the absence of anthrax contamination.

In one embodiment of the current invention, a kit to protect a mammal from anthrax is provided. In one embodiment, the kit comprises one or more fully human monoclonal antibodies comprises an amino acid sequence selected from the group consisting of: SEQ ID 2, SEQ ID 4, SEQ ID 6, SEQ ID 8, SEQ ID 10, SEQ ID 12, SEQ ID 14, and SEQ ID 16. In one embodiment, a medical device for delivering the antibody composition is included. The antibody composition can comprise one antibody, two antibodies, or three or more antibodies. The composition can be contained within or disposed onto the medical device. Alternatively, the composition is independent from said medical device. For example, the kit can include a syringe that contains one or more antibodies in a pre-determined dose. Or, the kit can include a vial of one or more antibodies, which is to be drawn into the syringe at the time of administration. In one embodiment, the medical device is a syringe, patch, nasal spray, or inhaler. Instructions for using the kit can also be included.

In one embodiment, the kit to protect a mammal from anthrax is to confer immunity to the mammal, wherein said mammal has not been exposed to anthrax. In another embodiment, the kit is to confer treatment to the mammal, wherein the mammal has been exposed to anthrax. In some embodiments, the kit includes an additional therapeutic agent such as an antibiotic (e.g., ciprofloxacin, doxycycline, and/or penicillin). The kit can also include a vaccine such as AVA and rPA. These additional ingredients can be packaged separately from the monoclonal antibodies, or can be combined with the monoclonal antibodies.

In one embodiment of the present invention, a method for immunizing a mammal and/or treating a mammal is provided. In one embodiment, the method comprises providing an antibody for administration to a mammal. The antibody prevents the assembly of a PA63 heptamer. An effective dose of the antibody is administered to the mammal, thereby preventing the assembly of the PA63 heptamer, thereby inhibiting transport of at least one of EF and LF into a mammalian host cell, thereby protecting the mammal from anthrax infection. Inhibiting the transport of at least one of EF and LF into the host cell comprises one or more of the following actions: preventing the entry of said at least one of EF and LF into the host cell, decreasing the number of said at least one of EF and LF that enters the host cell, and increasing the length of time for said at least one of EF and LF to enter the host cell. Inhibiting the transport of EF and/or LF may include any action that disrupts the natural toxic course of EF and/or LF.

In one embodiment, the antibody prevents the assembly of the PA63 heptamer by binding to a site on a PA83. In another embodiment, the method comprises providing one or more non-antibody agents that are operable to inhibit transport of said at least one of EF and LF into said mammalian host cell.

In one embodiment, the antibody is a monoclonal antibody. In a further embodiment, the antibody is a fully human monoclonal antibody. In yet another embodiment, the antibody for preventing heptamer assembly comprises the amino acid sequence selected from the group consisting of one or more of the following: SEQ ID 2, SEQ ID 4, SEQ ID 14, and SEQ ID 16.

In one embodiment, the method for immunizing a mammal and/or treating a mammal by preventing PA63 hepatmer formation comprises providing a first antibody and a second antibody to the mammal, wherein the two antibodies differ by at least one amino acid. In one embodiment, three or more antibodies are used.

In one embodiment, a pharmaceutical formulation for protecting a mammal from one or more toxic effects of anthrax is provided. The formulation can be for immunizing a mammal or for treating a mammal. In one embodiment, the formulation includes a binding agent (such as an antibody), wherein the binding agent binds to at least a portion of an anthrax toxin (e.g., PA, EF, and/or LF). In one embodiment, the binding agent interferes with the assembly of a PA63 oligomer. PA comprises a protein having a weight of about 83 kD (PA83) that is cleaved into a protein having a weight of about 63 kD (PA63). The binding agent inhibits the access of at least one of EF and LF to at least a portion of a host mammalian cell, thereby preventing one or more toxic effects of anthrax in said mammal.

In one embodiment, the pharmaceutical formulation is preventative and formulated for administration to a mammal that has not previously been exposed to anthrax. In one embodiment, the formulation is to immunize a mammal against one or more subsequent exposures to anthrax, and may, in some cases, serve to supplement a pre-existing immunity. In another embodiment, the pharmaceutical formulation is therapeutic and is formulated for administration to a mammal that has been exposed to anthrax.

In one embodiment, the binding agent is a monoclonal antibody. In another embodiment, the binding agent is a fully human monoclonal antibody. In one embodiment, the binding agent comprises the amino acid sequence selected from the group consisting of one or more of the following: SEQ ID 2, SEQ ID 4, SEQ ID 6, SEQ ID 8, SEQ ID 10, SEQ ID 12, SEQ ID 14, and SEQ ID 16. In another embodiment, the formulation comprises one, two or more than two antibodies. In one embodiment, the binding agent comprises a first binding agent and a second binding agent, wherein the two binding agents differ by at least one amino acid. The two binding agents may or may not bind to the same portion of the exotoxin. In one embodiment, the two binding agents bind to different portion of PA, thereby exerting a synergistic effect when co-administered.

In accordance with another embodiment of the invention, a method is disclosed for inhibiting the assembly of PA, the binding of the PA to ATRs, or the binding of LF or EF to the PA heptamer in a human. Preferably, the method comprises administering to such human the antibody of any of the immunoglobulins or fragments thereof described above, including those encoded by the sequences listed in FIGS. 5, 6, 8, 9, and 10.

In one embodiment of the present invention, a method of generating a fully human monoclonal antibody which recognizes at least a portion of an anthrax exotoxin is provided. In one embodiment, the method comprises administering cells (such as peripheral blood mononuclear cells, lymphocytes) from one or more human donors exposed to anthrax to an immuno-compromised animal, isolating at least one cell from said animal, and fusing the cell(s) with a fusion partner, thereby generating a hybridoma wherein the hybridoma produces a fully human monoclonal antibody which recognizes at least a portion of the anthrax exotoxin. In a preferred embodiment, one or more fully human monoclonal antibodies produced by the methods described herein are provided. In one embodiment, a cell line that generates fully human antibodies is obtained.

In one embodiment, the method for generating antibodies comprises screening the generated antibodies. In another embodiment, the method includes transforming at least a portion of the cells with Epstein Barr Virus (EBV). In yet another embodiment, the method comprises characterizing the animal's immune response using a test bleed. In a further embodiment, one or more booster injections of anthrax antigen are administered to the animal. One or more injections of anti-CD8 can also be administered. In one embodiment, a double selection method (e.g., HAT and ouabain) to select against undesirable cells is used.

In one embodiment, the method for generating antibodies uses cells from human donors that have been vaccinated against anthrax. A human donor that has been inadvertently exposed to anthrax can also be used.

In one embodiment, the method for generating antibodies uses immuno-compromised (immuno-deficient) animals such as the SCID mouse. One of skill in the art will understand that the SCID mouse, or other mammal, can be irradiated to further compromise the immune system. In one embodiment, the fusion partner is a hybridoma. In one embodiment, the fusion partner is a myeloma. In one embodiment, the fusion partner is derived from a mouse myeloma MOPC2 or P3x63Ag8.653.

BRIEF DESCRIPTION OF THE DRAWINGS

FIG. 3 shows testing of the presence of neutralizing PA bioactivity in donor and HuPBL-SCID engrafted mice sera.

FIG. 5 shows the nucleotide (SEQ ID NO: 1) and amino acid (SEQ ID NO: 2) sequence of the 21D9 MAb heavy chain variable region.

FIG. 6 shows the nucleotide (SEQ ID NO: 3) and amino acid (SEQ ID NO: 4) sequence of the 21D9 MAb light chain variable region.

FIG. 8 shows the nucleotide sequence (SEQ ID NOS: 5 & 7) and amino acid sequence (SEQ ID NOS: 6 & 8) of the 1C6 Mab heavy (SEQ ID NOS: 5 & 6) and light chain (SEQ ID NOS: 7 & 8) variable regions.

FIG. 9 shows the full nucleotide sequence (SEQ ID NOS: 9 & 11) and amino acid sequence (SEQ ID NOS: 10 & 12) of the 4H7 Mab heavy (SEQ ID NOS: 9 & 10) and light chain (SEQ ID NOS: 11 & 12) variable regions.

FIG. 10 shows the full nucleotide sequence (SEQ ID NOS: 13 & 15) and amino acid sequence (SEQ ID NOS: 14 & 16) of the 22G12 Mab heavy (SEQ ID NOS: 13 & 14) and light chain (SEQ ID NOS: 15 & 16) variable regions.

FIG. 12 shows protection of rats from a lethal toxin challenge by aglycosylated antibody.

FIG. 13 shows protection of rats from a lethal toxin challenge 17 hours and 1 week after administration of antibody.

FIG. 16A shows a schematic of fragments of PA83 generated by trypsin and chymotrypsin digest based on the sequences and mapping studies. FIG. 16B shows a Western blot analysis of intact (I), trypsin (T), chymotrypsin (C) and combination of trypsin and chymotrypsin (T+C) generated PA fragments probed with AVP-1C6, AVP-22G12 and AVP-21D9. FIG. 16C shows Coomassie stained SDS-PAGE of antibody bound PA83 treated with trypsin lane (1) Molecular weight markers; (2) PA83 no trypsin; (3) no antibody; (4) AVP-22G12; (5) AVP-21D9; (6) AVP-1C6; (7) AVP-1451 isotype matched human IgG anti-tetanus control.

DETAILED DESCRIPTION OF THE PREFERRED EMBODIMENT

A preferred embodiment of the present invention provides a prophylactic or therapeutic agent to counter the effects of anthrax toxin that is released as a mechanism of bioterrorism. Thus, in one embodiment of the present invention, a potent counter-terrorism measure is provided. Antibodies which bind to one or more components of the tripartite anthrax exotoxin, the methods of making said antibodies, and the methods of using said antibodies are provided. In a preferred embodiment, a method of passive immunization is used to protect a mammal against anthrax infection. Passive immunization, as used herein, shall be given its ordinary meaning and shall also mean the introduction of antibodies, for example, from an individual with active immunity, or of genetically-engineered or synthetic antibodies, to treat infection. Passive immunization shall also include the administration of one or more antibodies, or fragments thereof, to confer immunity to a specific pathogen or toxin In several embodiments, the antibodies provide protection either as single agents or combined in a cocktail. Anthrax, as defined herein, shall be given its ordinary meaning and shall also include the toxin secreted by *Bacillus anthracis*, and shall include the tripartite anthrax toxin, synthetic or naturally-occurring, and shall also be defined broadly to include one or more of the following components, synthetic or naturally-occurring: protective antigen (PA), lethal factor (LF) and edema factor (EF). Thus, antibodies to "anthrax" shall include antibodies to any portion of one or more components of the anthrax toxin. Moreover, as used herein, the singular forms "a", "an", and "the" include plural reference, unless the context clearly dictates otherwise. Thus, for example, a reference to "a host cell" includes a plurality of such host cells, and a reference to "an antibody" is a reference to one or more antibodies and equivalents thereof known to those skilled in the art.

The term "fully human antibodies," as used herein, shall mean antibodies with 100% human protein sequences. A fully human monoclonal antibody to anthrax may be generated by administering human cells (typically from one or more human donors exposed to anthrax) to an immuno-compromised animal, isolating a lymphocytic cell from that animal, and fusing the lymphocytic cell with a fusion partner, which then produces a fully human monoclonal antibody which recognizes at least a portion of an anthrax exotoxin. The terms "antibody" and "immunoglobulin" shall be used interchangeably. Antibodies for immunizing mammals and/or for treating mammals are provided in preferred embodiments of the invention. Preferred mammals include humans, but non-human mammals, livestock and domesticated mammals may also benefit from certain embodiments of the invention.

Figure 1:
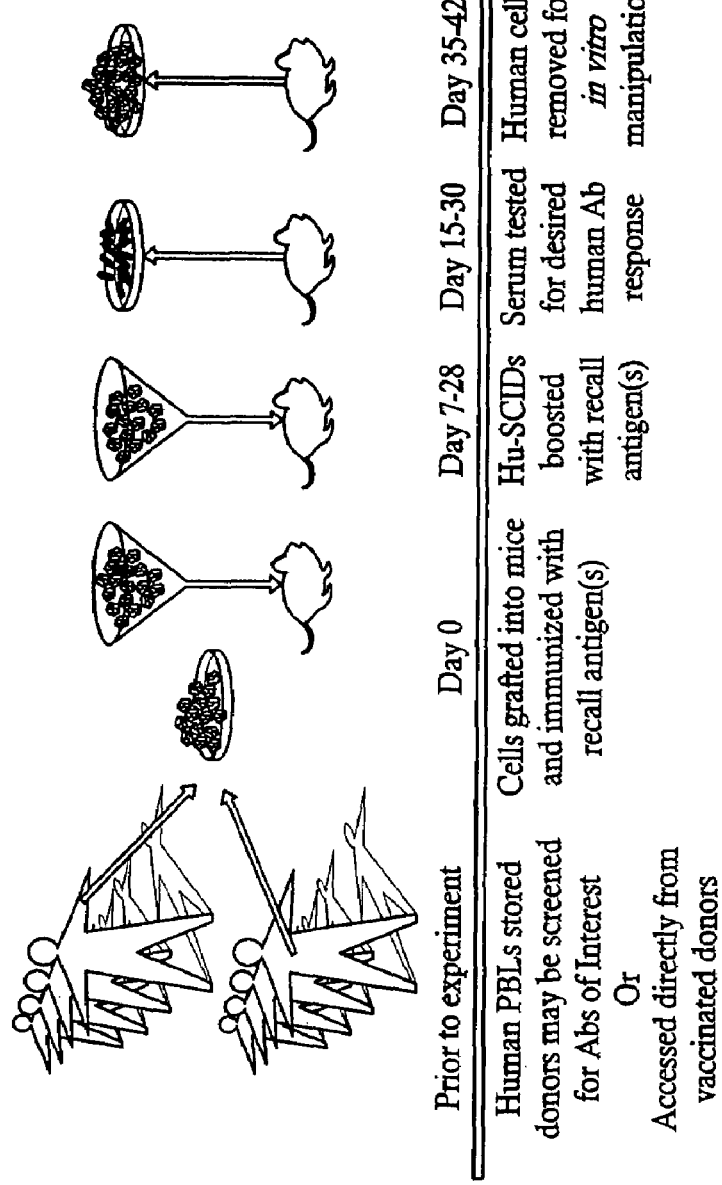
FIG. 1 shows a timeline of the engraftment of SCID mice with human PBMC from anthrax-vaccinated donors.
Figure 2A:
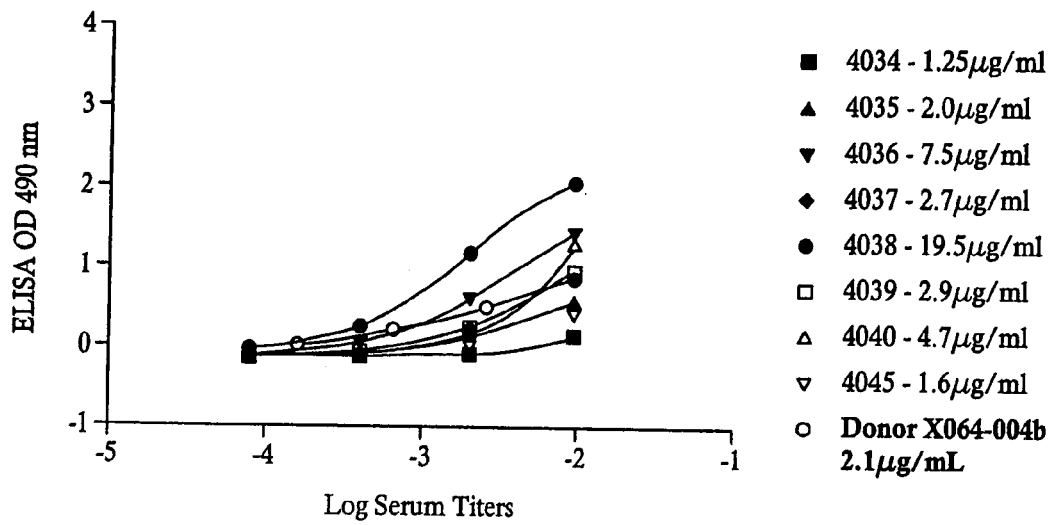
FIGS. 2A-H show anti-anthrax toxin (PA83) or non-specific IgG levels in donor plasma compared to the engrafted mice.
Figure 2B:
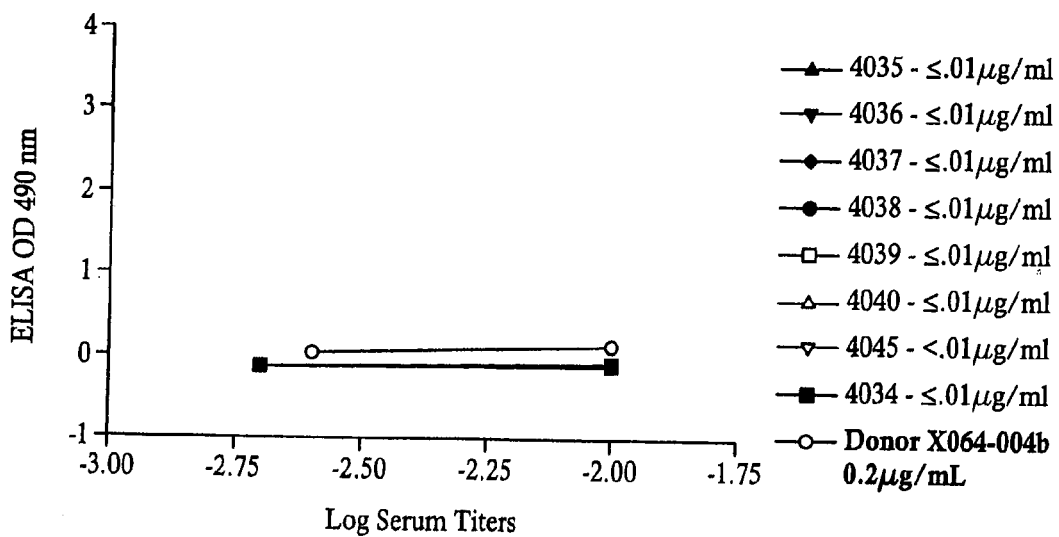
Figure 2C:
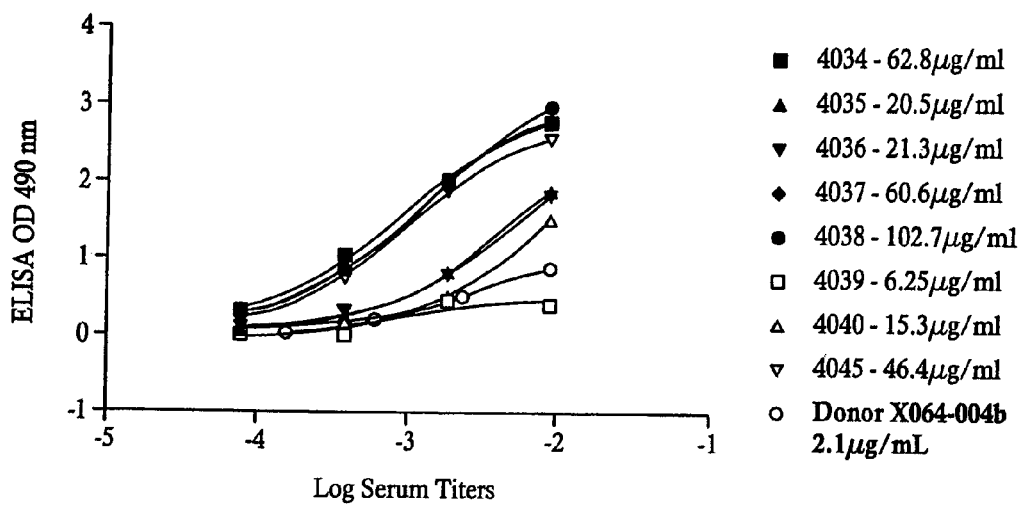
Figure 2D:
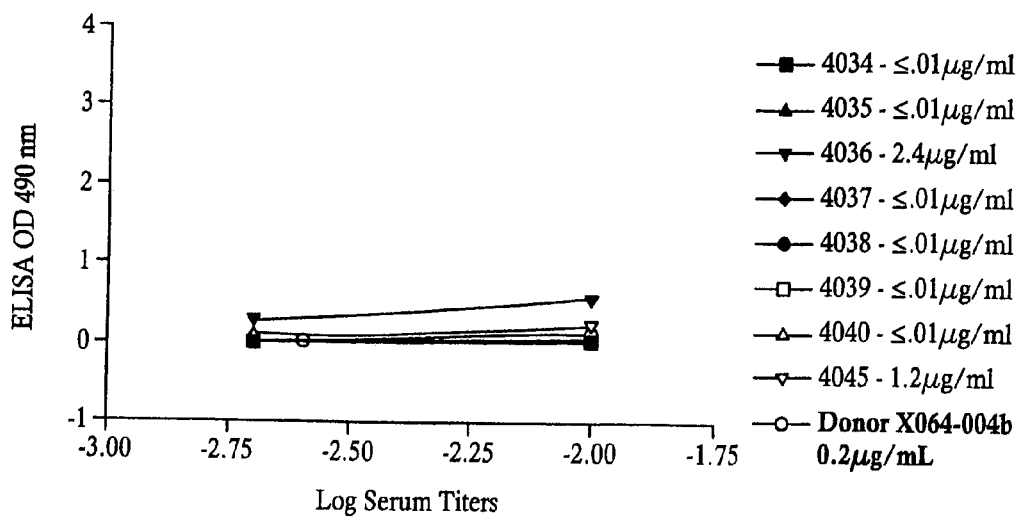
Figure 2E:
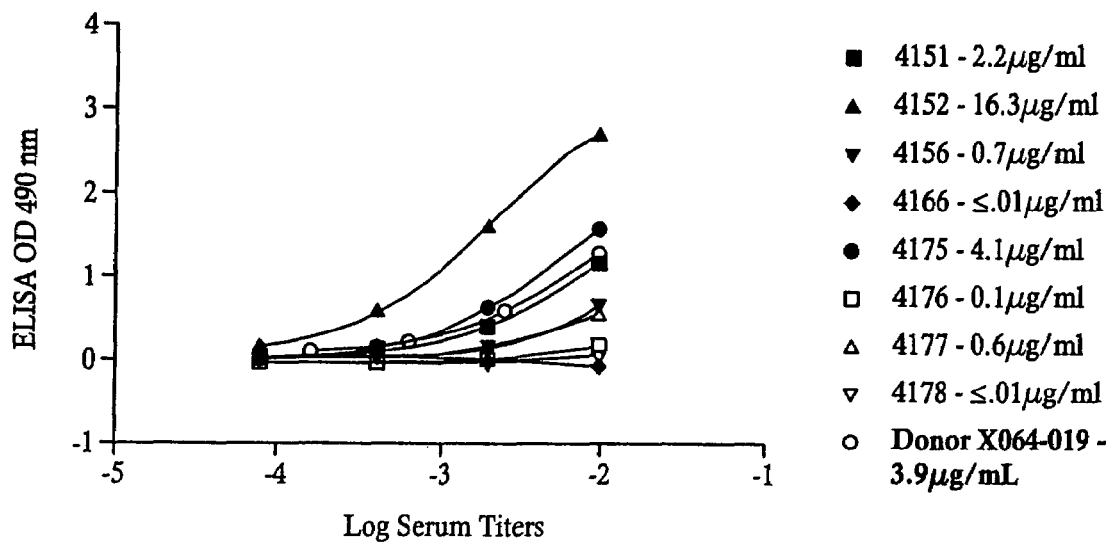
Figure 2F:
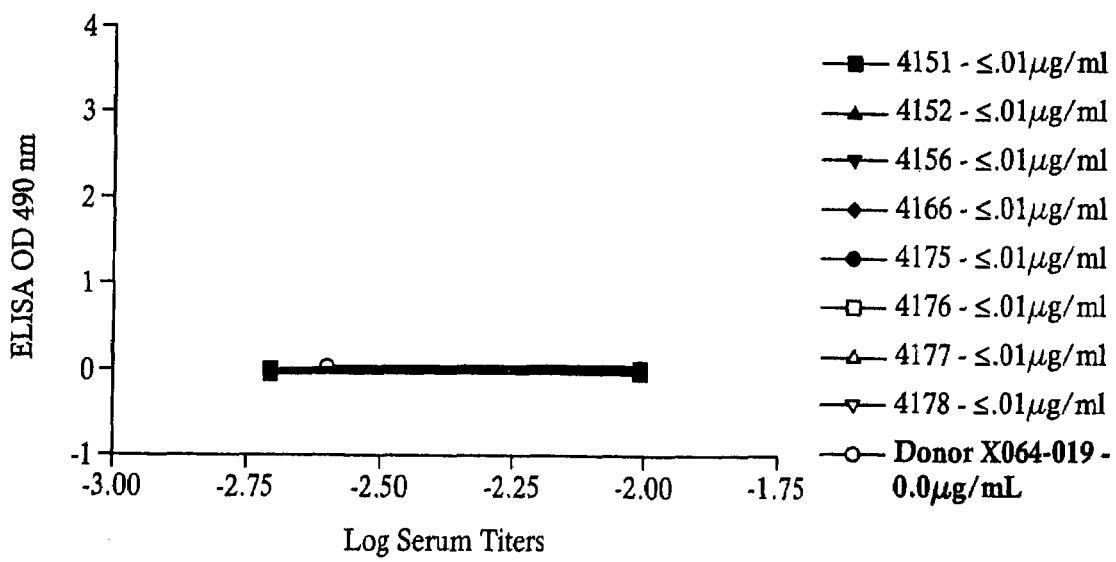
Figure 2G:
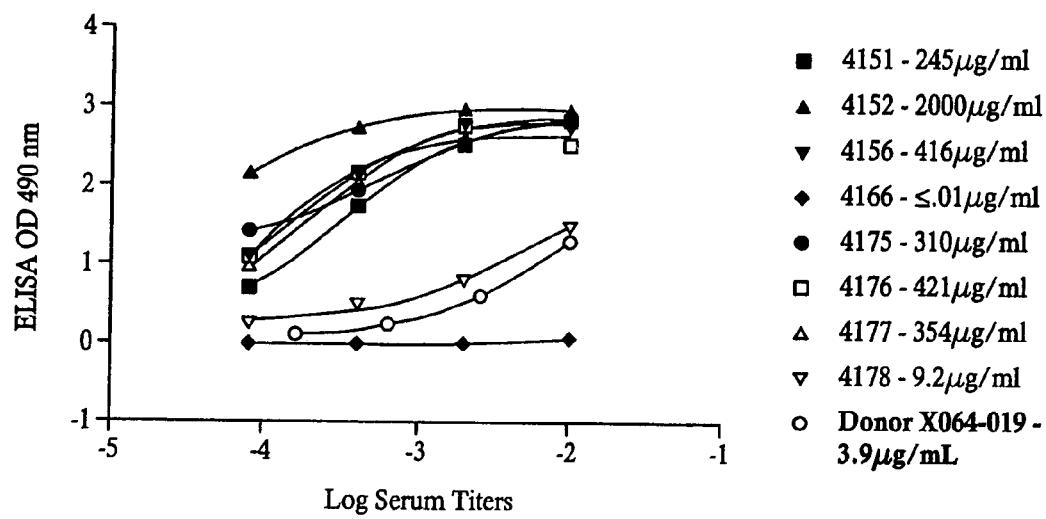
Figure 2H:
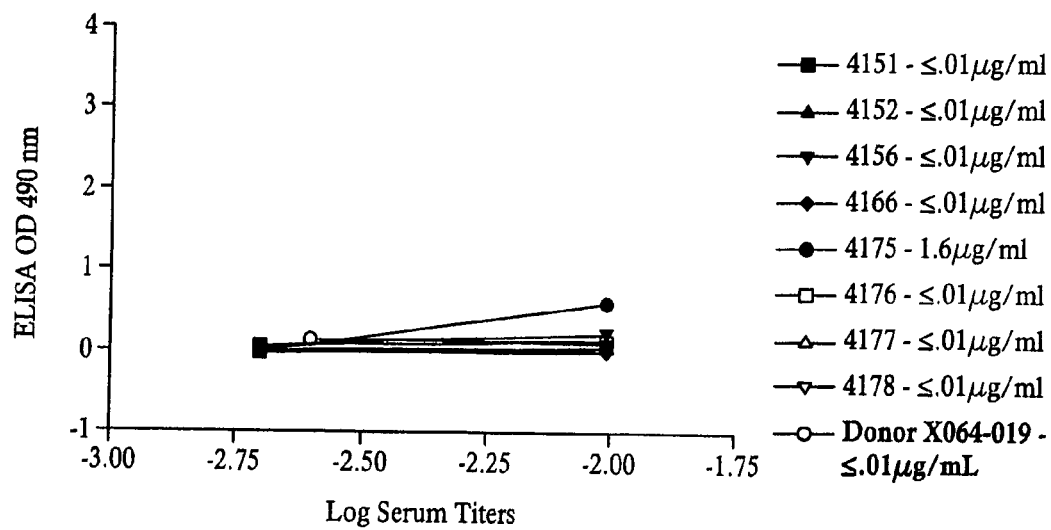

As shown generally in FIG. 1, in one embodiment, a method of preparing a fully human monoclonal antibody which specifically recognizes at least a portion of the protective antigen (PA) of an anthrax exotoxin is provided. In one embodiment, this method includes obtaining peripheral blood mononuclear cells from human donors. After obtaining the peripheral blood mononuclear cells from donors, the blood cells are administered to an immuno-compromised animal. The lymphocytic cells are isolated and fused with a hybridoma fusion partner.

In a preferred embodiment, blood cells from donors who have been exposed to anthrax are obtained. Such exposure may have occurred naturally through exposure, or may have occurred by vaccination. Moreover, in one embodiment, exposure may have occurred decades, years or days prior to obtaining the donor's blood cells. In one embodiment, the "memory" of said exposure is captured or recalled and is selectably expanded by immunizing the engrafted SCID mice. Thus, in a preferred embodiment, said recall technology is used to generate human monoclonal antibodies. In one embodiment, the human donor has been vaccinated against anthrax. The use of human blood cells that have been "pre-exposed" to anthrax, or another target antigen, yields surprising and unexpected advantages. These advantages include the generation of antibodies with higher affinity, higher specificity, and more potent neutralization capabilities.

In another embodiment, unexposed or naïve blood cells are used. In one embodiment, the unexposed blood cells are exposed to anthrax ex vivo or in vitro, prior to engraftment in the immuno-deficient mouse. Thus, said initially unexposed cells are transformed into exposed cells and can be used in accordance with the recall technology described above.

In a preferred embodiment, peripheral blood mononuclear cells are obtained from a donor. In another embodiment, other cell types are obtained, including but not limited to lymphocytes, splenocytes, bone marrow, lymph node cells, and immune cells.

In one embodiment, the blood cells are administered to an immuno-compromised or immuno-deficient animal. In one embodiment, the animal is a SCID mouse. In one embodiment, the animal is irradiated.

In one aspect of the invention, the animal's immune response is characterized using a test bleed. In another embodiment, the generated antibodies are screened and isolated. In yet another embodiment, the lymphocytic cells are transformed with EBV. In one embodiment, one or more booster injections of anthrax antigen are administered to the immuno-compromised animal. In another embodiment, one or more injections of anti-human CD8 is administered to the animal. In yet another aspect, a double selection method to select against undesirable cells is used, including, but not limited to using HAT and ouabain. In one embodiment of the present invention, the hybridoma fusion partner is the mouse myeloma P3x63Ag8.653. In another embodiment of the present invention, the hybridoma fusion partner is derived from the mouse myeloma P3x63Ag8.653.

In one embodiment of the present invention, a series of human anti-anthrax PA toxin antibodies is provided. In one embodiment, a monoclonal antibody (AVP-21D9, or "21D9") is provided. As illustrated in FIG. 4, antibody 21D9 was effective in RAW cell assays in toxic inhibition. The $IC_{50}$ of 21D9 was found to be in the picomolar range and in approximately equimolar stoichiometry with the input PA toxin. The equilibrium dissociation constant ($K_d$) as determined by BiaCore analysis revealed this embodiment to bind antigen with high affinity in the picomolar range (Table 1). Deduced amino acid sequence from the 21D9 hybridoma heavy and light chain cDNA allowed assignment to known VH and VL gene families, although significant mutation away from these germline sequences was also observed thereby indicating the occurrence of somatic hypermutation. In one embodiment, the mechanism by which 21D9 provides protection is also provided.

Antibody 21D9, and other antibodies described herein, can be used for human use in vivo for prophylaxis and treatment of Anthrax Class A biowarfare toxins. Thus, in several embodiments, a method for preventing anthrax infection is provided. In one embodiment, a method for treating mammals to prevent anthrax infection is provided. In a further embodiment, a method to treat mammals that have been exposed to anthrax is provided. In particular, FIG. 4 shows the determination of AVP-21D9 $IC_{50}$ using RAW 264.7 cell-based assay. The results demonstrate that 1.2 nM PA and 0.56 nM LF in a 96 well assay on confluent RAW 264.7 cells cause 100% cell lysis. The AVP-21D9 was assessed at various concentrations for the ability to inhibit the lethal toxin. From the dose response curve an $IC_{50}$ values was estimated. AVP-1C6 and AVP-22G12 $IC_{50}$ determinations were carried out likewise. The $IC_{50}$ values for AVP-21D9, AVP-1C6, and AVP-22G12 was 0.21 nM, 0.36 nM, and 0.46 nM, respectively.

In one embodiment, antibody 22G12, and methods of making and using same, are provided. In another embodiment, antibody 1C6, and methods of making and using same, are provided. In a further embodiment, antibody 4H7, and methods of making and using same, are provided. Chemical modifications, mutations, and other variants of these antibodies are also provided, including but not limited to 21D9.1 and 22G12.1.

Preferred embodiments provide a fully human monoclonal antibody that specifically binds to a component of an anthrax exotoxin or combinations of components thereof. The anthrax exotoxin can be in tripartite form. The anthrax toxin can be naturally-occurring or synthetic. In a tripartite form, the anthrax exotoxin comprises PA, EF, and LF.

In preferred embodiments, a monoclonal antibody is produced by rescuing the genes encoding antibody variable region from the antibody-producing cells, and establishing stable recombinant cell lines producing whole IgG/kappa or IgG/lambda. In one embodiment, antibody-producing cells recovered from the immunized animal are subjected to cell fusion with an appropriate fusion partner. The resulting hybridomas are then screened in terms of the activity of the produced antibodies. The hybridomas subjected to selection are screened first in terms of the binding activity to a component of the tripartite anthrax exotoxin. In one embodiment, the hybridomas are selected based on ability to bind to PA, LF and/or EF proteins in an immunoassay, such as an ELISA test and also a bioassay. In one embodiment, the hybridoma shows protection in the bioassay. The cells from positive wells are used to isolate mRNA. From the mRNA, cDNA is reverse transcribed. The variable domains are PCR amplified using primers for the 5' end of the variable chain, and constant region or frame work primers.

In one embodiment, the amino acid sequences constituting the variable regions of the antibodies having a desired binding activity to PA, LF and/or EF and the nucleotide sequences encoding the same is provided. Several embodiments provide immunoglobulin variable regions containing the amino acid and nucleotide sequences shown in FIGS. 5, 6, 8, 9, and 10.

FIGS. 5 and 6 show specific heavy chain and light chain variable regions of 21D9. In one embodiment, one or more of these sequences, or portions thereof, produce antibodies having a desired binding activity to PA, LF and/or EF. One skilled in the art will appreciate that these sequences, and any products thereof, can comprise one or more variations or modifications. Variants include amino acid, codon, or base pair substitutions, additions, and deletions. In some embodiments, these changes are silent such that they do not substantially alter the properties or activities of the polynucleotide or polypeptide. Variants also include alterations in the nucleic acid sequence encoding the amino acid or peptide sequences. Such variations or modifications may be due to degeneracy in the genetic code or may be engineered to provide desired properties. Variations or modifications of the nucleotide sequence may or may not result in modifications of the encoded amino acid sequence.

In a further embodiment, cDNA encoding the immunoglobulin variable regions containing the nucleotide sequences shown in FIG. 5 and FIG. 6, and variants thereof, is provided.

In one embodiment, these amino acid sequences or cDNA nucleotide sequences are not necessarily identical but may vary so long as the specific binding activity to PA, LF and/or EF is maintained. In another embodiment, variation in nucleotide sequence is accommodated. In several embodiments, the site corresponding to CDR is highly variable. In the CDR region, even entire amino acids may vary on some occasions. Results from experimental data show that in one embodiment, the heavy chain of 21D9 exhibits a VH3 class, a 3-43 VH locus, 26 mutations from the germ line, 6-19(1) DH(RF), and JH4B. Results from experimental data show that in one embodiment, the light chain of 21D9 exhibits a VK1 light chain class, a L12 locus, 14 mutations from the germ line, and JK1.

In one embodiment, each immunoglobulin molecule consists of heavy chains having a larger molecular weight and light chains having a smaller molecular weight. The heavy and light chains each carries a region called "a variable region" in about 110 amino acid residues at the N-terminus, which are different between the molecules. Variable regions of a heavy chain and a light chain are designated VH and VL, respectively. The antigen-binding site is formed by forming a dimer between the heavy chain variable region VH and the light chain variable region VL. In one embodiment, the coupling of the antigen-binding site and the antigen is through electrostatic interaction. The variable region consists of three CDRs and four frameworks. The CDR forms a complementary steric structure with the antigen molecule and determines the specificity of the antibody. The three CDRs inserted between the four framework regions (FRs) are present like a mosaic in the variable region (E. A. Kabat et al., Sequences of proteins of immunological interest, vol. I, 5th edition, NIH Publication, 1991). The amino acid sequences of FRs are well conserved, but those of CDR are highly variable and may thus be called hypervariable regions. Among the amino acid sequences of the antibody specifically recognizing PA, LF and/or EF, a CDR that determines the binding activity to antigens is provided in some embodiments. Preferred embodiments provide CDRs shown in FIG. 5 and FIG. 6.

The cDNAs bearing the nucleotide sequences coding the variable regions in immunoglobulin molecules can be cloned from hybridomas that produce the monoclonal antibody to PA, LF and/or EF of the tripartite anthrax exotoxin. To amplify the sequences, PCR can be performed. To identify active clones, ELISA can be used to determine binding to PA, LF and/or EF of the tripartite anthrax exotoxin. Further studies on affinities of an antibody that can bind to PA, LF and/or EF of the tripartite anthrax exotoxin can be determined with kinetic and thermodynamic studies using apparatus, such as BiaCore (Biacore, Piscataway, N.J.) surface plasmon resonance apparatus for measuring binding affinity and binding kinetics. Thus, in one embodiment, specific cDNA sequences are provided.

In one embodiment, a monoclonal antibody that can block oligomerization of the PA component of anthrax exotoxin is provided. Accordingly, a monoclonal antibody of preferred embodiments can have preventive or therapeutic uses. A preferred monoclonal antibody can be used in a pharmaceutical composition as a treatment for a mammal exposed to anthrax exotoxin. Accordingly, preferred embodiments provide methods of passive immunization of a mammal against anthrax and/or treating a mammal exposed to anthrax.

A monoclonal antibody of several embodiments can be administered as a pharmaceutical composition. Thus, in one embodiment, the antibody can be administered by several different routes, including but not limited to: parenterally, topically, and orally. The term "parenterally", as used herein, shall be given its ordinary meaning and shall also include subcutaneous, intravenous, intraarterial, injection or infusion techniques, without limitation. In one embodiment, the antibody is administered intramuscularly. The term "topically", as used herein, shall be given its ordinary meaning and shall also encompasses administration rectally and by inhalation spray, as well as the more common routes of the skin and the mucous membranes of the mouth and nose. In some embodiments, one or more anti-anthrax antibodies are administered via a syringe, patch, inhalants, and/or oral formulation. Pre-prepared and pre-dosed anti-anthrax antibody formulations can be available in kits so that individuals have easy and quick access to the antibody in the event that those persons are warned of an impending anthrax exposure or have discovered that they have recently been exposed to anthrax. Such pre-dosed formulations (e.g., syringes, patches, sprays, oral compositions) may be particularly useful for the military. Government workers and individuals working in hospitals may also benefit from such anti-anthrax preparations. Such pre-prepared kits may also be made available to the general public as a safety measure.

One skilled in the art will understand the appropriate dosage to be administered. Actual dosage levels of preferred antibody in a pharmaceutical composition may be varied so as to administer an amount of a preferred antibody that is effective to achieve the desired therapeutic response for a particular patient. The selected dosage level will depend upon the activity of the particular agent the route of administration, the severity of the condition being treated, and the condition and prior medical history of the patient being treated. If desired, the effective daily dose may be divided into multiple doses for purposes of administration, e.g., two to four separate doses per day. It will be understood, however, that the specific dose level for any particular patient will depend upon a variety of factors including the body weight, general health, diet, time and route of administration, combination with other drugs and the severity of the particular disease being treated.

According to several embodiments of the present invention, the pharmaceutical formulation can be in a variety of forms, including, but not limited to, injectable fluids, suppositories, powder, tablets, capsules, syrups, suspensions, liquids and elixirs. The preferred route is by injection. In one embodiment, an antibody preparation is pre-packaged in self-injectable devices, such as syringes. One advantage of such pre-packaged antibody devices is that individuals could protect themselves on short notice in response to a biological attack, or threat of a biological attack.

Preferred embodiments of the present invention provide a kit for identifying the presence of anthrax exotoxin in a sample. In a preferred kit, there is a monoclonal antibody which specifically recognizes at least a portion of a component of an anthrax exotoxin. A sample is contacted with a monoclonal antibody which specifically recognizes at least a portion of a component of an anthrax exotoxin. If an anthrax exotoxin is present, then the binding of the anthrax exotoxin with the monoclonal antibody can be determined. The term "kit" as used herein shall be given its ordinary meaning and shall also include a compilation, collection, or group of materials used for a common goal or purpose. A kit to test for the presence or absence of anthrax, according to on embodiment of the invention includes one or more of the following: an anti-anthrax antibody, a swabbing material, gloves, an assay kit, and instructions.

In one embodiment, passive immunization is provided in conjunction with one or more other therapies, including but not limited to antibiotic therapy. In one embodiment, ciprofloxacin hydrochloride and/or other antibiotics are administered before, after, and/or simultaneously with one or more of the antibodies, or fragments thereof, described herein. In some embodiments, the treatment of anthrax infection by two or more therapies provides a synergistic effect.

The disclosure below is of specific examples setting forth preferred methods for making agents according to several embodiments of the present invention. These examples are not intended to limit the scope, but rather to exemplify preferred embodiments. For example, although the following examples describe the generation of antibodies to anthrax, antibodies to other antigens can also be made by following the examples set forth below. Various adaptations and modifications to adapt the protocols described herein will be understood by those skilled in the art.

EXAMPLE 1

Indirect Elisa

Flat bottom microtiter plates (Nunc F96 Maxisorp) were coated with 50 μl of *Bacillus anthracis* Protective Antigen (PA) or Lethal Factor (LF)(List Biological Laboratories (Campbell, Calif.) at a concentration of 1 μg/mL in PBS overnight at 4° C. Plates were washed four times with PBS with Tween 20 at 0.1% and 50 μl of diluted sera was added to the wells for one hour at room temperature. Plates were washed as before and 50 μl of secondary antibody, HRP conjugated Goat anti-Human IgG, Fcγ specific, or HRP conjugated Goat anti-Human IgM, Fc5μ specific, (Jackson ImmunoResearch, West Grove, Pa.) were added and incubated for one hour at room temperature. After another wash step, 100 μL of a substrate solution containing 0.4 mg/mL OPD (O-phenlenediamine dihydrochloride) in citrate buffer (0.025 M at pH 5.0) was added; after 15 minutes, 25 μl of 3N HCl was added to stop the reaction and plates were then read on a Microplate reader (VersaMax, Molecular Devices, Sunnyvale, Calif.) at 490 nm.

EXAMPLE 2

Raw 264.7 Cell Line in Vitro Bioassay

The presence of neutralizing (protective) antibody to anthrax toxins PA and LF in the antisera were determined using an in vitro protection bioassay with the mouse macrophage RAW 264.7 target cell line. Hanna, P. et al., *Microbiology* 90:10198 (1993). PA (100 ng/ml) and LF (50 ng/ml) were pre-incubated with the indicated dilutions of antiserum for 30 minutes at 37° C. in a working volume of 100 μl of DMEM medium supplemented with 10% fetal calf serum, 2 mM L-glutamine, 100 IU/ml penicillin and 100 μg/ml streptomycin. This 100 μl volume was subsequently transferred into a 96 well flat bottom tissue culture plate containing $1\times10^4$ RAW 264.7 cells/well in 100 μl of the same medium. The culture was incubated for 3 hours at 37° C. The wells were washed twice with media. The residual attached cells were lysed and the released Lactate dehydrogenase (LDH) levels were measured using a CytoTox 96 kit (Promega, Madison, Wis.). Briefly, 10 μl Lysis Solution was added to 100 μl media per well and the mix incubated 45 minutes in a humidified chamber at 37° C., 5% $CO_2$. An aliquot of the lysed material (50 μl) was transferred to a new plate and 50 μl assay buffer added. The plate was incubated for 30 minutes prior to adding 50 μl stop solution. The plates were read at 490 nm using a Tecan Spectra Fluor (Zurich, Switzerland) reader.

EXAMPLE 3

Engraftment of SCID Mice with Human PBMC from Anthrax-vaccinated Donors

Peripheral blood mononuclear cells were enriched from whole blood of anthrax-vaccinated donors by density gradient centrifugation using Histopaque, 1077-1 (Sigma, St. Louis, Mo.). One of skill in the art will understand that other types of cells can also be used in accordance with several embodiments of the present invention. Typically, one unit of blood from donors was obtained. Female SCID/bg 12 week old mice were each engrafted (via i.p. inoculation) with $2.5\times10^7$ isolated human PBMC. They were treated concomitantly i.p. with a volume of conditioned medium from the OKT8 mouse hybridoma grown in Ex-cell 620 hybridoma serum free medium (JRH, KS) and 2 mM L-glutamine which contained 0.2 mg of the anti-CD8 antibody (used directly without further purification). The mice were immunized with a combination of PA and LF (i.p.) 2 μg each adsorbed to Alum (Imject®, Pierce, Rockford, Ill.) and subsequently boosted (i.p.) on day 7, 19 and day 26. Mice were inoculated with 0.5 ml of EBV obtained from spent conditioned culture medium of the B95-8 marmoset cell line on day 7. Test bleeds were obtained from the orbital sinus on days 14 and 29. Two consecutive i.p. and iv boosts with PA and LF were administered (5 μg via each route on day 40 and 41, both in saline) prior to harvesting cells for fusion on day 42, also at which time an additional test bleed sample was obtained.

EXAMPLE 4

Generation of Human Hybridomas

Splenocytes, as well as lymphoblastoid cell line (LCL) tumors were harvested on day 42 from those mice showing positive test bleeds in indirect ELISA. Human hybridomas were generated from these in separate fusions using a murine myeloma P3x63Ag8.653 with PEG-1500 (Sigma, St. Louis, Mo.) as described by Kearney J F, Radbruch A, Liesegang B, Rajewski K (1979), with the modification that the P3x63Ag8.653:lymphocyte ratio for fusion was between 1:3-1:5. A mouse myeloma cell line that has lost immunoglobulin expression, but permits the construction of antibody-secreting hybridoma cell lines. J Immunol 123:1548-1558.

Although P3x63Ag8.653 was used in this exemplary method, one skilled in the art will understand that several fusion partners can be used in accordance with various embodiments of the current invention, including, but not limited to, cells derived from the mouse myeloma MOPC2, triomas, etc. Double selection to select against the EBV-LCL and the unfused P3x63Ag8.653 fusion partner was carried out using a combination of HAT selection and ouabain. A concentration of 8 μM ouabain (Sigma, St. Louis, Mo.) was used. One skilled in the art will appreciate that other poisons or toxins that interfere with the Na+/K+ ATPase can also be used in accordance with several embodiments of the present invention. In addition, one skilled in the art will understand that other selection methods can also be used.

EXAMPLE 5

Treatment and Subcloning of 21D9 Hybridoma Cells 16 days after fusion, hybridoma supernatants from 96 well plates were tested in indirect ELISA. Approximately 17 out of 1248 wells (13 plates) showed an initial positive ELISA signal on PA. All of them were chosen for further analysis and were subcloned at 5 cells/well on a feeder layer of irradiated NHLF (Cambrex, Baltimore, Md.) in RPMI (Omega, San Diego, Calif.) supplemented with 10% FBS, 20% hybridoma cloning factor (IGEN, Gaithersbourg, Md.), 5 ng/ml human IL6 (I-188, Leinco), 1×HT (Sigma), 1× Vitamins (Omega), 1× Sodium pyruvate (Omega), 1×NEAA (Omega), 2× L-glutamine (Omega) and without antibiotics. The subcloning plates were tested in indirect ELISA after 10 days. Individual colonies from highly positive wells were hand-picked under a microscope using Pasteur pipets drawn out to fine points. After 2 weeks, individually picked clones were retested in indirect ELISA. Positive cells were recovered and the transcript mRNA encoding the immunoglobulins were reverse transcribed to form cDNA. Although the methodology for antibody 21D9 is described herein, one of skill in the art will understand that the exemplary methodology described herein can also be used to make and test the other antibodies described and claimed herein.

EXAMPLE 6

Variable Region 21D9 IGG and IGK cDNA Cloning and Expression

Total RNA was prepared from specific ELISA positive hybridomas using RNeasy Mini Kit (Qiagen, Valencia, Calif.). Mixture of VH and VL cDNAs were synthesized and amplified in a same tube using One-Step RT-PCR Kit (Qiagen, Valencia, Calif.). Cycling parameters were 50° C. for 35 min, 95° C. for 15 min, 35 cycles of 94° C. for 30 sec, 52° C. for 20 sec and 72° C. for 1 min 15 sec, and 72° C. for 5 min.

Primers used for RT-PCR were:

```
For VHγ
Forward
a. CVH2
TGCCAGRTCACCTTGARGGAG          (SEQ ID NO: 17)

b. CVH3
TGCSARGTGCAGCTGKTGGAG          (SEQ ID NO: 18)

c. CVH4
TGCCAGSTGCAGCTRCAGSAG          (SEQ ID NO: 19)

d. CVH6
TGCCAGGTACAGCTGCAGCAG          (SEQ ID NO: 20)

e. CVH1257
TGCCAGGTGCAGCTGGTGSARTC        (SEQ ID NO: 21)

Reverse (located at 5' of CH1 region)
a. CγII
GCCAGGGGGAAGACSGATG            (SEQ ID NO: 22)

For VLκ
Forward
a. VK1F
GACATCCRGDTGACCCAGTCTCC        (SEQ ID NO: 23)

b. VK36F
GAAATTGTRWTGACRCAGTCTCC        (SEQ ID NO: 24)

c. VK2346F
GATRTTGTGMTGACBCAGWCTCC        (SEQ ID NO: 25)

d. VK5F
GAAACGACACTCACGCAGTCTC         (SEQ ID NO: 26)

Reverse (located in constant region)
a. Ck543
GTTTCTCGTAGTCTGCTTTGCTCA       (SEQ ID NO: 27)

For VLλ
Forward
a. VL1
CAGTCTGTGYTGACGCAGCCGCC        (SEQ ID NO: 28)

b. VL2
CAGTCTGYYCTGAYTCAGCCT          (SEQ ID NO: 29)

c. VL3
TCCTATGAGCTGAYRCAGCYACC        (SEQ ID NO: 30)

d. VL1459
CAGCCTGTGCTGACTCARYC           (SEQ ID NO: 31)

e. VL78
CAGDCTGTGGTGACYCAGGAGCC        (SEQ ID NO: 32)

f. VL6
AATTTTATGCTGACTCAGCCCC         (SEQ ID NO: 33)

Reverse (located in constant region)
a. CL2
AGCTCCTCAGAGGAGGYGG            (SEQ ID NO: 34)
```

The RT-PCR was followed by nested PCR using High Fidelity Platinum PCR Mix (Invitrogen, Carlsbad, Calif.). A micro liter of RT-PCR products was used for VHγ, VLκ or VLλ specific cDNA amplification in the separate tube. At substantially the same time, restriction enzyme sites were introduced at both ends. Cycling parameters were 1 cycle of 94° C. for 2 min, 6° C. for 30 sec and 68° C. for 45 sec, 35 cycles of 94° C. for 40 sec, 54° C. for 25 sec and 68° C. for 45 sec, and 68° C. for 5 min.

Each specific PCR product was separately purified, digested with restriction enzymes, and subcloned into appropriate mammalian full-length Ig expression vectors as described below.

EXAMPLE 7

Subcloning into Vectors

Primers for nested PCR were used. These primers were as follows:

```
For VHγ
Forward (adding BsrGI site at 5' end)
a. BsrGIVHF2
AAAATGTACAGTGCCAGRTCACCTTGARGGAG    (SEQ ID NO: 35)

b. BsrGIVHF3
AAAATGTACAGTGCSARGTGCAGCTGKTGGAG    (SEQ ID NO: 36)

c. BsrGIVHF4
AAAATGTACAGTGCCAGSTGCAGCTRCAGSAG    (SEQ ID NO: 37)

d. BsrGIVHF6
AAAATGTACAGTGCCAGGTACAGCTGCAGCAG    (SEQ ID NO: 38)

e. BsrGIVHF1257
AAAATGTACAGTGCCAGGTGCAGCTGGTGSARTC  (SEQ ID NO: 39)

Reverse (including native ApaI site)
a. CγER
GACSGATGGGCCCTTGGTGGA               (SEQ ID NO: 40)
```

VHγPCR products are digested with BsrG I and Apa I and ligated into pEEG1.1 vector that is linearized by Spl I and Apa I double digestion.

```
For VLκ
Forward (adding AgeI site, Cys and Asp at
5' end)
a. AgeIVK1F
                                      (SEQ ID NO: 41)
TTTTACCGGTGTGACATCCRGDTGACCCAGTCTCC b. AgeIVK36F
                                      (SEQ ID NO: 42)
TTTTACCGGTGTGAAATTGTRWTGACRCAGTCTCC c. AgeIVK2346F
                                      (SEQ ID NO: 43)
TTTTACCGGTGTGATRTTGTGMTGACBCAGWCTCC d. AgeIVK5F
                                      (SEQ ID NO: 44)
TTTTACCGGTGTGAAACGACACTCACGCAGTCTC Reverse (adding SplI site, located between
FR4 and 5' of constsnt region)
a. SplKFR4R12
                                      (SEQ ID NO: 45)
TTTCGTACGTTTGAYYTCCASCTTGGTCCCYTG b. SplKFR4R3
                                      (SEQ ID NO: 46)
TTTCGTACGTTTSAKATCCACTTTGGTCCCAGG c. SplKFR4R4
                                      (SEQ ID NO: 47)
TTTCGTACGTTTGATCTCCACCTTGGTCCCTCC d. SplKFR4R5
                                      (SEQ ID NO: 48)
TTTCGTACGTTTAATCTCCAGTCGTGTCCCTTG
```

VLκ PCR products are digested with Age I and Spl I and ligated into pEEK1.1 linearlized by Xma I and Spl I double digestion.

```
For VLλ
Forward (adding ApaI site at 5' end)
a. ApaIVL1
ATATGGGCCCAGTCTGTGYTGACGCAGCCGCC      (SEQ ID NO: 49)

b. ApaIVL2
ATATGGGCCCAGTCTGYYCTGAYTCAGCCT        (SEQ ID NO: 50)

c. ApaIVL3
ATATGGGCCCAGTATGAGCTGAYRCAGCYACC      (SEQ ID NO: 51)

d. ApaIVL1459
ATATGGGCCCAGCCTGTGCTGACTCARYC         (SEQ ID NO: 52)

e. ApaIVL78
ATATGGGCCCAGDCTGTGGTGACYCAGGAGCC      (SEQ ID NO: 53)

f. ApaIVL6
ATATGGGCCCAGTTTTATGCTGACTCAGCCCC      (SEQ ID NO: 54)

Reverse (adding Avr II site, located between FR4
and 5' of constant region)
a. AvrIIVL1IR
TTTCCTAGGACGGTGACCTTGGTCCCAGT         (SEQ ID NO: 55)

b. AvrIIVL237IR
TTTCCTAGGACGGTCAGCTTGGTSCCTCCKCCG     (SEQ ID NO: 56)

c. AvrIIVL6IR
TTTCCTAGGACGGTCACCTTGGTGCCACT         (SEQ ID NO: 57)

d. AvrIIVLmixIR
TTTCCTAGGACGGTCARCTKGGTBCCTCC         (SEQ ID NO: 58)
```

VLλPCR products are digested with Apa I and Avr II and ligated into pEELg vector linearlized by Apa I and Avr II double digestion. The positive clones were identified after transient co-transfection by determining expression in the supernatants by indirect ELISA on PA coated plates. CHO K1 cells were transfected with different combinations of IgG and IgK cDNAs using Lipofectamine-2000 (Invitrogen, Carlsbad, Calif.). The supernatants were harvested about 48 hours to about 72 hours after transfection. Multiple positive clones were sequenced with the ABI 3700 automatic sequencer (Applied Biosystems, Foster City, Calif.) and analyzed with Sequencher v4.1.4 software (Gene Codes, Ann Arbor, Mich.).

EXAMPLE 8

Stable Cell Line Establishment

Ig heavy chain or light chain expression vector were double digested with Not I and Sal I, and then both fragments were ligated to form a double gene expression vector. CHO-K1 cells in 6 well-plate were transfected with the double gene expression vector using Lipofectamine 2000 (Invitrogen, Carlsbad, Calif.). After 24 hrs transfection cells were transferred to a 10 cm dish with selection medium (D.MEM supplemented with 10% dialyzed FBS, 50 µM L-methionine sulphoximine (MSX), penicillin/streptomycin, GS supplement). Two weeks later MSX resistant transfectants were isolated and expanded. Anti-PA antibody high producing clones were selected by measuring the supernatant with PA specific ELISA assay. MSX concentration was increased from 50 µM to 100 µM to enhance the antibody productivity.

EXAMPLE 9

Serum Free Adaptation Procedure

A stable cell line was cultured in 10% dialyzed FBS in ExCell 302 Serum Free Medium (JRH, 1000M) with 1×GS (JRH, 100 M) and 25-100 µM L-Methionine Sulphoximine (Sigma). Cells were treated with trypsin (Omega) and split 1:5. The culture medium was switched to 5% FBS containing media and the cells were cultured 2 days. When the cells adapted to growing in 5% FBS containing media, the media was changed to serum free medium containing 2.5% dialyzed FBS for 1-2 days, then to 100% of serum free media. At this point the cells were no longer adherent and then transferred to and cultured in Integra flasks for small scale production in serum free media. Purification was carried out by filtering the spent culture media through a 0.2µ filter and then loaded directly to a HiTrap Protein A column (Pharmacia), followed by washing with 20 mM Sodium phosphate pH 7.4, and the antibody was eluted with 0.1M glycine HCl pH3.4 and immediately neutralized with ⅟10 volume of 1M Tris-HCl pH 8.0. The protein content in eluted fractions was determined by absorbance at 280 nm, the fractions containing antibody were pooled and dialyzed against phosphate buffered saline pH 7.4 (2×500 volumes), and filter sterilized through a 0.2µ filter. The antibody was further characterized by SDS-PAGE and the purity exceeded 95%.

EXAMPLE 10

Affinity Determinations

Affinity constants were determined using the principal of surface plasmon resonance (SPR) with a Biacore 3000 (Biacore Inc.). A Biacore CM5 chip was used with affinity purified goat anti-human IgG+A+M (Jackson Immuno Research) conjugated to two flowcells of the CM5 chip according to manufacturer's instructions. An optimal concentration of an antibody preparation is first introduced into one of the two flowcells, and is captured by the anti-human Ig. Next, a defined concentration of antigen is introduced into both flow-cells for a defined period of time, using the flowcell without antibody as a reference signal. As antigen binds to the captured antibody of interest, there is a change in the SPR signal, which is proportional to the amount of antigen bound. After a defined period of time, antigen solution is replaced with buffer, and dissociation of the antigen from the antibody is then measured, again by the SPR signal. Curve-fitting software provided by Biacore generates estimates of the association and dissociation rates, and affinities.

The results from this study are summarized in Table 1, below. The equilibrium dissociation constant ($K_d$) for recombinant form of the 21D9, 1C6, 4H7 and 22G12 MAb was determined by BiaCore analyses. The rate constants $k_{on}$ and $k_{off}$ were evaluated directly from the sensogram in the BiaCore analysis and the $K_d$ was deduced.

TABLE 1

Affinity Determination Of Antibody 21D9 And Other Antibodies On PA (83 Kd) Protein.

| Antibody | Dissociation Constant ($K_D$) M | Association Rate ($k_{on}$) | Dissociation Rate ($k_{off}$) |
|---|---|---|---|
| AVP-21D9 | $8.21 \times 10^{-11}$ | $1.80 \times 10^5$ | $1.48 \times 10^{-5}$ |
| AVP-1C6 | $7.11 \times 10^{-10}$ | $1.85 \times 10^5$ | $1.31 \times 10^{-4}$ |
| AVP-4H7 | $1.41 \times 10^{-10}$ | $1.74 \times 10^5$ | $2.45 \times 10^{-5}$ |
| AVP-22G12 | $5.12 \times 10^{-10}$ | $1.01 \times 10^5$ | $5.17 \times 10^{-5}$ |

EXAMPLE 11

Human IGG Quantification by Immunoenzymetric Assay

Flat bottom microtiter plates (Nunc F96 Maxisorp) were coated overnight at 4° C. with 50 µl of Goat anti-Human IgG, Fcγ specific, (Jackson ImmunoResearch) at 1 µg/mL in PBS. Plates were washed four times with PBS-0.1% Tween 20. Meanwhile, in a separate preparation plate, dilutions of standards (in duplicate) and unknowns were prepared in 100 µl volume of PBS with 1 mg/ml BSA. A purified monoclonal human IgG1κ myeloma protein (Sigma, St. Louis, Mo.) was used as the standard and a different IgG1κ myeloma protein (Athens Research, Athens, Ga.) served as an internal calibrator for comparison. Diluted test samples (50 µl) were transferred to the wells of the assay plate and incubated for one hour at room temperature. Plates were washed as before and 50 µl of the detecting antibody (1:4000 in PBS with 1 mg/ml BSA.) Goat anti-Human Kappa-HRP (Southern Biotechnology Associates, Inc., Birmingham, Ala.) was added and incubated for one hour at room temperature. After another wash step, 100 µl of a substrate solution containing 0.4 mg/ml OPD (O-phenlenediamine dihydrochloride) in citrate buffer (0.025 M at pH 5.0) was added. Following a 15 minute substrate incubation, 25 µl of 3N HCl stop solution was added and plates were read on a Microplate reader (VersaMax, Molecular Devices, Sunnyvale, Calif.) at 490 nm. Unknowns were interpolated from standard curve values using SoftMaxPro v4.0 software (Sunnyvale, Calif.).

EXAMPLE 12

Results

Testbleeds from mice engrafted with human PBMC from an anthrax-vaccinated donor and further boosted via immunization in vivo were obtained. FIG. 2A-H shows comparison results of the anti-anthrax toxin levels in the donor plasma as compared to the sera of engrafted mice. These figures show an IgG response to PA83 in engrafted sera. The presence of IgG antibody to anthrax toxin PA83 components in sera of engrafted SCID mice sera were determined by ELISA after the first and second boosts. The specific levels of IgG and donor levels are shown. The IgG response from Donor X064-0042 cells engrafted into SCID mice at day 15 (A) and day 30 (C). The IgG response from Donor X064-043 cells engrafted into SCID mice at day 15 (E) and day 30 (G). Control data with PBS is also shown.

Figure 3:
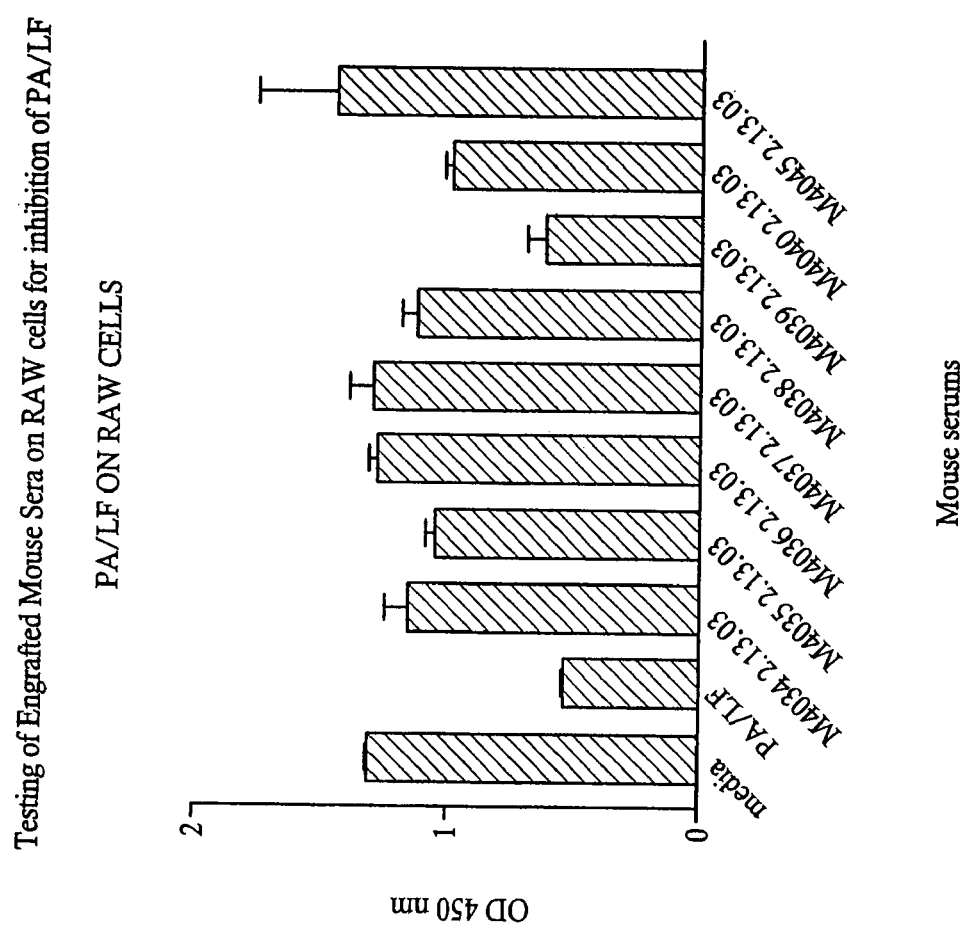

FIG. 2A-H shows that the mouse sera level of functional immunoreactive (indirect ELISA) antibody is considerably higher than that observed in the donor. A range of levels of immunoreactive antibody was observed in the engrafted mice. Test bleeds from engrafted mice were also evaluated for the presence of anti-PA/LF protective antibody in the mouse macrophage RAW cell bioassay (FIG. 3). In this bioassay, the translocation of PA/LF complex into the cell triggers signal transduction events (MAPKK mediated) that lead to cell death, and a lower bioassay signal. The presence of protective antibody reverses this. The original donor plasma did not appear to contain detectable levels of protective antibody (even when tested at a lower dilution) in comparison with the engrafted mice. Both the increase in immunoreactive (ELISA) antibody and the appearance of seroprotection in the engrafted mice show the amplification of a seroprotective immune response to anthrax toxin elicited by repeated immunization of human PBMC-engrafted SCID mice. In one embodiment, the presence of appropriate seropositivity is one preferred criterion for selecting appropriate animals for fusion to generate human hybridomas.

A series of 14 individual fusions was carried out with cells obtained from various compartments (either peritoneal wash (PW), spleen (SP), or LCL tumors (TU) within the peritoneal cavity) of the engrafted mice. In several fusions, the cells were pooled from several engrafted mice determined to be producing specific anti-anthrax toxin antisera by Indirect ELISA and RAW Cell bioassay prior to fusion. A summary of the fusion results is shown in Table 2.

TABLE 2

Origin Of Resulting Hybridomas Obtained In IJ-8 Anti-Anthrax Toxin Study.

| Plate # | Mouse # | Cell Sources | Partner | Positive Wells | Subcloned |
|---|---|---|---|---|---|
| 1 | 4034/35/37/38/40/41 | PW | P3X | 0 | – |
| 2 | 4034/35/37/38/40/41 | PW | P3X | 0 | – |
| 3 | 4034/35/37/38/40/41 | PW | P3X | 0 | – |
| 4 | 4037/38 | SP | P3X | 0 | – |
| 5 | 4034/45 | SP | P3X | 6 | + |
| 6 | 4034/45 | SP | P3X | 10 | + |
| 7 | 4035/40 | SP | P3X | 0 | – |
| 8 | 4035/40 | SP | P3X | 0 | – |
| 9 | 4035/40 | SP | P3X | 0 | – |
| 10 | 4035/40 | SP | P3X | 0 | – |
| 11 | 4035/40 | SP | P3X | 1 | + |
| 12 | 4035/38/40 | TU | P3X | 0 | – |
| 13 | 4035/38/40 | TU | P3X | 0 | – |
| 14 | 4034/45 | TU | P3X | 0 | – |

Hybridomas were initially selected based on their ability to bind to PA (83 kD) protein adsorbed to polystyrene microtiter plate wells in an indirect ELISA. A wide range of values for the relative amount of specific anti-PA antibody in the supernatants was observed. In parallel, each of the supernatants was tested individually in the Anthrax toxin protection RAW cell bioassay.

Figure 4:
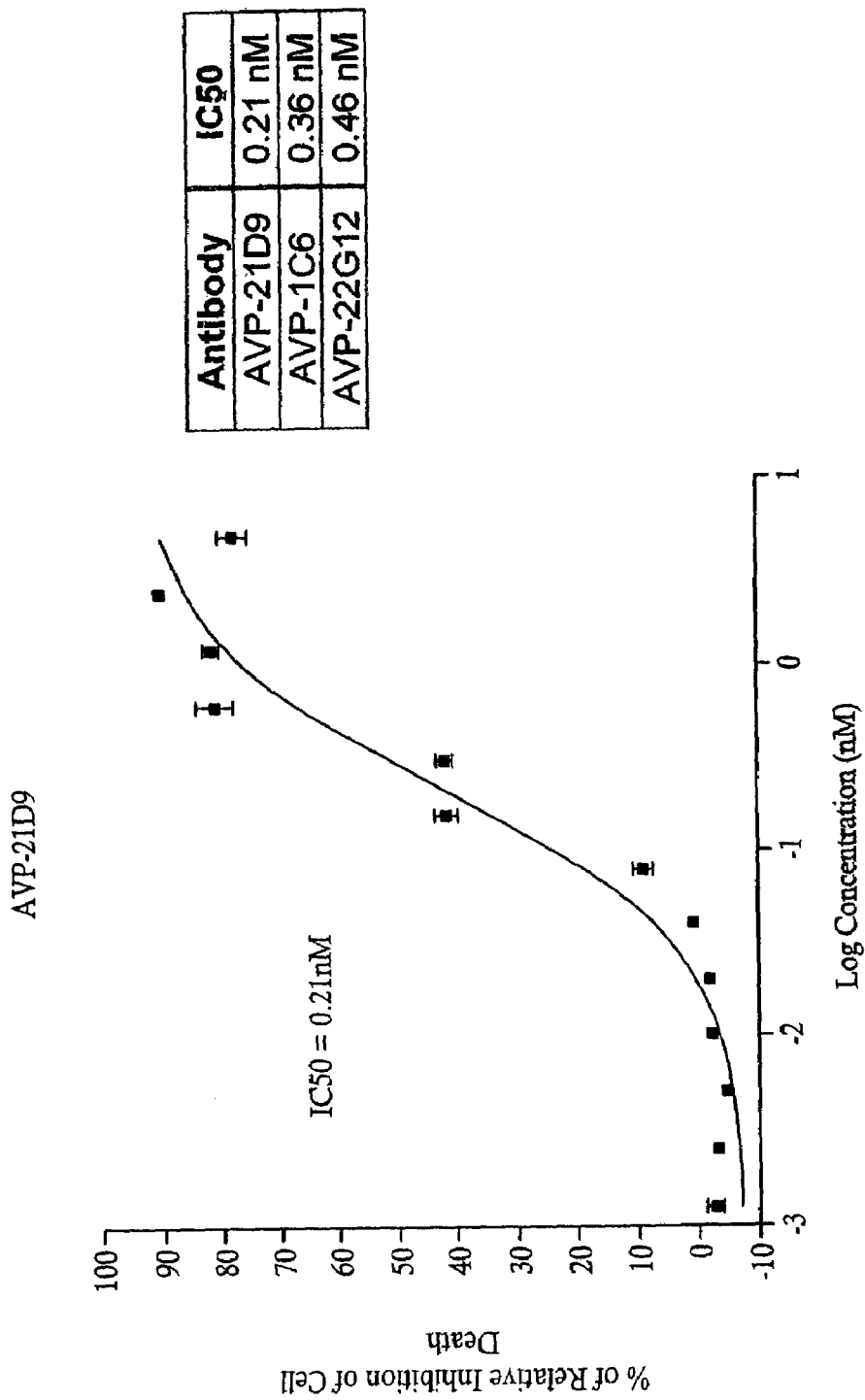
FIG. 4 shows determination of AVP-21D9 IC50 using RAW 264.7 cell based assay. AVP-21D9, AVP-22G12 and AVP-1C6 IC50 were assessed at various concentrations for the ability to inhibit the lethal toxin.

A dose-response curve of hybridoma-derived 21D9 in the RAW cell bioassay was used to evaluate the effective in vitro $IC_{50}$ protective concentration using a cocktail of the PA (83 kD) and LF toxins. An antibody $IC_{50}$ of 0.21 nM was observed for AVP-21D9 and IC50s for the other antibodies are shown in the inset table (FIG. 4).

Figure 17A:
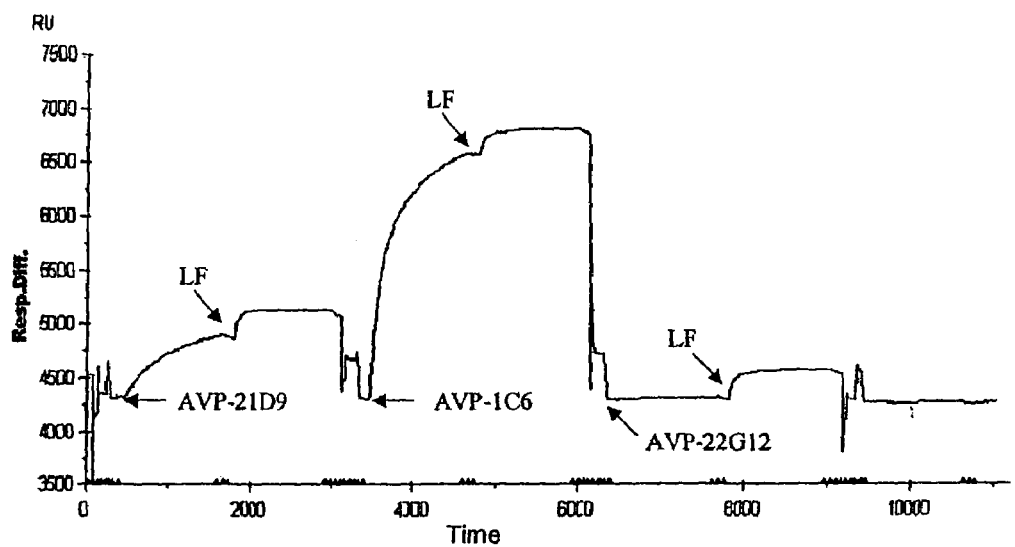
FIGS. 17A-B show the interaction of human anti-anthrax PA antibodies with PA63 and lethal factor (FIG. 17A) and PA83 and soluble anthrax toxin receptor (FIG. 17B) by surface plasmon resonance analysis.

The 21D9 antibody was found to bind to the intact (83 kD) form as well as the cleaved (63 kD) form of the PA toxin, but to a lesser degree to the heptamer as determined by BiaCore analysis (Pharmacia, Peapack, N.J.). Additionally, there was no evidence that the antibody was able to inhibit LF binding to PA (63 kD) heptamer as determined by sequential incubations in the BiaCore (FIG. 17A). This finding potentially implicates the domain 2 on the PA toxin as the epitope blocked by this antibody.

The nucleotide sequences of the 21D9 MAb heavy and light chains variable regions were determined (FIG. 5 and FIG. 6).

The alignment of variable regions using V BASE DNAPLOT software (18) showed that 21D9 heavy chain used VH gene from VH3 family (3-43 locus), D region segment 6-19 (in first reading frame) with N region addition and JH4b. 21D9 light chain was from the VKI family (L12 locus), and used the JK1 region segment. The number of mutations from most closely related germline were 26 (heavy chain) and 14 (light chain), respectively. Comparisons with germline V genes suggest that the 21D9 V regions had undergone extensive somatic mutations, characteristic of an Ag-driven immune response. Table 3, provided below, shows the germline deviation of the antibodies.

Anthrax exotoxins, the dominant virulence factors produced by *Bacillus anthracis* are a tripartite combination of protective antigen (PA), lethal factor (LF) and edema factor (EF). Although not wishing to be bound by this theory, these toxins are thought to have an important role in anthrax pathogenesis; initially to impair the immune system, permitting the anthrax bacterium to evade immune surveillance to disseminate and reach high concentrations; and later in the infection the toxins may contribute directly to death in the host animals including humans. Antibodies that neutralize the PA component of the exotoxin could provide an effective protection from anthrax toxin exposure, early and potentially late in the infection. In one embodiment, the generation of a panel of very potent fully human anti-PA neutralizing antibodies derived from PBMCs obtained from vaccinated donors is provided.

The antibodies were generated through the combined use of in vivo immunization of SCID mice reconstituted with human PBMC (U.S. Pat. Nos. 5,476,996; 5,698,767; 5,811,524; 5,958,765; 6,413,771; and 6,537,809, all herein incorporated by reference), subsequent recovery of human B cells expressing anti-PA antibodies and immortalization via cell fusion with the mouse myeloma cells. Human immunoglobulin cDNAs were isolated and subcloned into the mammalian expression vector. Recombinant antibodies were first screened by an in vitro neutralization assay using the RAW264.7 mouse macrophage cell line. Furthermore, selected antibodies were evaluated for neutralization of lethal toxin in vivo in the Fisher 344 rat bolus toxin challenge model (Maynard, 2002; Wild, 2003, herein incorporated by reference).

Analysis of the variable regions indicated that antibodies recovered from SCID mice were diverse and hyper-mutated. Among these antibodies, a single IV administration of AVP-21D9 or AVP-22G12 was found to confer full protection with only 0.5×(AVP-21D9) or 1×(AVP-22G12) molar excess relative to PA in the rat toxin challenge prophylaxis model. Aglycosylated PA neutralizing antibodies also protected rats from lethal toxin challenge. Although not wishing to be bound by the following theory, it is believed that the PA toxin neutralizing activity in vivo is not depended on Fc mediated effector functions.

In one embodiment, these potent fully human anti-PA toxin-neutralizing antibodies generated may be used for in vivo human use for prophylaxis and/or treatment against Anthrax Class A bioterrorism toxins.

In one embodiment, antibodies that bind to the PA component of the tripartite anthrax-toxin and which provide protection as single agents are provided. In one embodiment, antibody 21D9 is provided. In another embodiment, antibody 22G12 is provided. In a further embodiment, antibody 1C6 is provided. In one embodiment, these antibodies are used as single agent in preventing and/or treating anthrax infection. In other embodiments, combination of two or more of these antibodies are used to treat mammals who have been exposed to aerosolized *Bacillus anthracis* spores, or exposed to other forms of anthrax.

Figure 19:
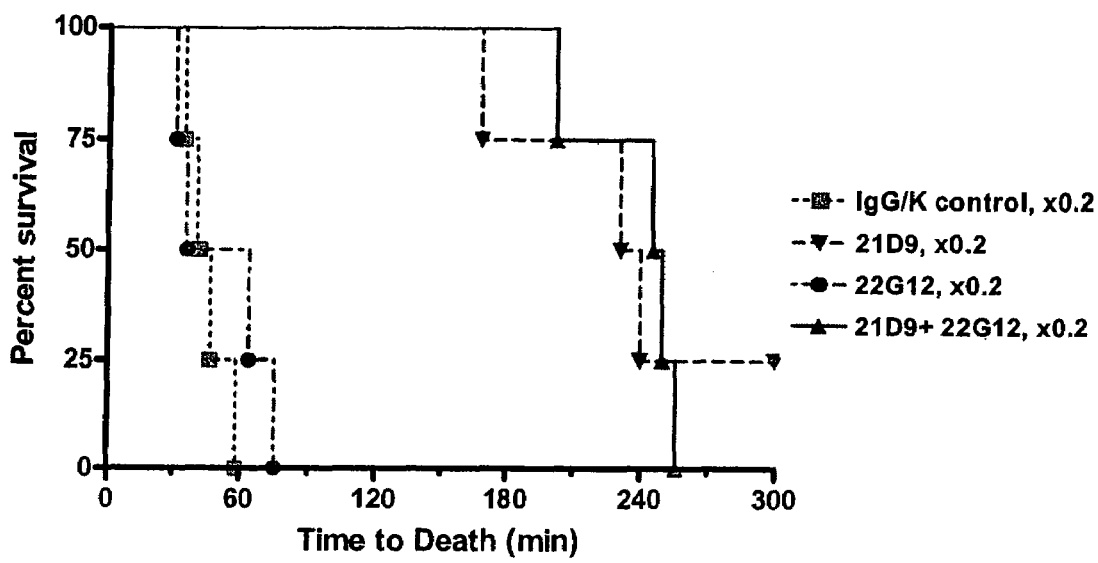
FIG. 19 shows rat survival data when a combination of AVP-22G12 and AVP-21D9 are administered together.

In some embodiments, two or more anti-anthrax antibodies are administered to the same patient. The antibodies can be administered simultaneously, or sequentially. In one embodiment, administration of two or more antibodies provided a synergistic effect. For example, FIG. 19 shows rat survival data when a combination of AVP-22G12 and AVP-21D9 are administered together. When administered together, even at very low concentrations, the combination has an enhanced activity as compared to the individually administered antibodies. It is important to note that FIG. 19 shows rat survival data in a very sensitive rat model; survival data is shown in minutes. Further, although AVP-22G12 is an effective anti-anthrax antibody, the survival data for AVP-22G12 in this model is similar to that for the IgG/K control. This is because extremely low doses of AVP-22G12 were administered to the animals. At higher doses, AVP-22G12, like AVP-21D9, is an effective and efficacious anti-anthrax antibody.

In one embodiment, two or more antibodies that exert their actions via different mechanisms are administered to a mammal. In this manner, the treatment and prevention of anthrax infection may be enhanced because the two (or more) antibodies are acting on different pathways. In this manner, an anti-anthrax embodiment according to one embodiment of the invention can be combined with an anti-anthrax antibody of the prior art. Further, an anti-anthrax embodiment according to one embodiment of the invention can also be combined with another anti-anthrax prophylactic or therapeutic, such an antibiotic.

Figure 7:
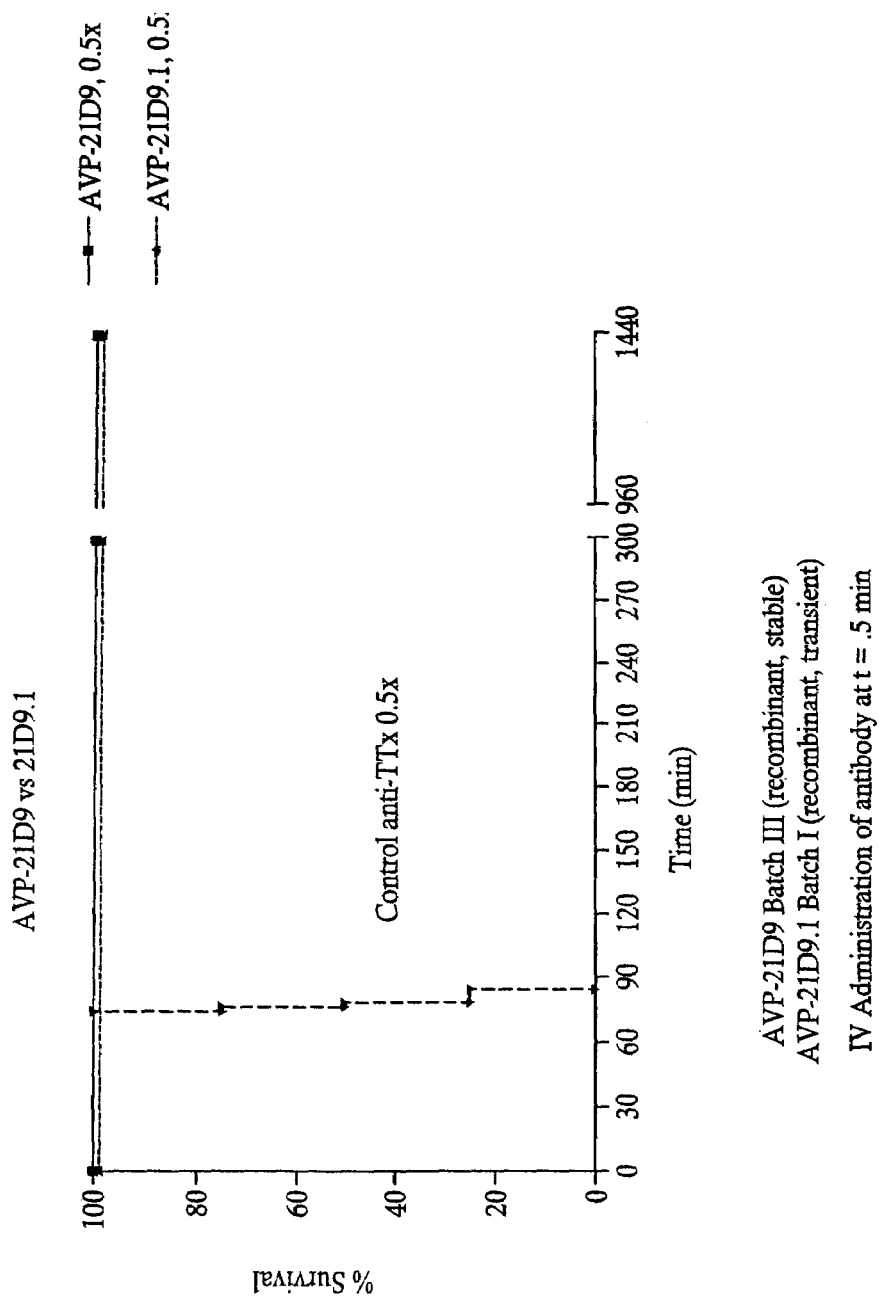
FIG. 7 shows protection of rats from a lethal toxin challenge.

In one embodiment, antibodies that bind to PA with a range of high affinities, from about 82 pM to about 700 pM, as determined by surface plasmon resonance (BiaCore 3000), is provided. Experimental data showed that antibodies IC6, 21D9 and 22G12 recognize unique non-competing sites and also, 21D9, 22G12 and 1C6 do not appear to interfere with PA recognition of soluble TEM-8. The biological efficacy of these three antibodies were determined in an in vitro anthrax lethal toxin neutralization assay. All three antibodies protected RAW 264.7 cell from toxin induced cell death and provided 50% neutralization at sub-equimolar ratio of antibody to toxin (FIG. 7).

EXAMPLE 13

Human Monoclonal Antibodies from Anthrax Vaccinated Donors are Protective Against Anthrax Lethal Toxin in vivo A panel of anthrax toxin neutralizing human monoclonal antibodies was evaluated for neutralization of anthrax lethal toxin in vivo in the Fisher 344 rat bolus toxin challenge model. The following experiment compared five human antibodies that neutralize anthrax lethal toxin in vitro in an in vivo rat toxin challenge model. The most potent inhibitor of the anthrax toxin AVP-21D9 protected rat with as little as about 0.5× antibody to toxin in vivo. This corresponds to about 0.12 mmols/200-250 g rat. According to one embodiment of the invention, AVP-21D9 was shown to be a potent inhibitor of anthrax toxin in vitro with an estimated $IC_{50}$ of 0.2 nM. The potency ranking observed in the in vitro assay was matched in the rat in vivo protection assay. Removing the carbohydrates associated with the constant domains of the IgG did not reduce the potency of the antibody. In some embodiments, the carbohydrates are useful for the retention of Fc mediated effector functions. AVP-22G12 was also potent at inhibiting the toxin in vivo at 1×, but not as potent as AVP-21D9 at the 0.5× dose. Removal of the glycosylation site in AVP-22G12 did impact on its potency suggesting that although the effector functions are not required, in the absence of the carbohydrates the overall structure of the antibody is impacted to reduce its efficacy to 80% survival at the designated 5 hour time point, which dropped to 60% due to an additional death at 12 hours. At the lower dose of AVP-22G12 no protection was observed but the time to death was delayed significantly. AVP-1C6 at 1× was only 80% protective and failed to protect or delay time to death at the lower dose. The in vivo potency trend observed AVP21D9>AVP-22G12>AVP-1C6, is the similar to the potency in vitro and correlates well with affinity of antibody to PA.

Accordingly, vaccination with Anthrax Vaccine Adsorbed can induce the production of a range of protective antibodies. The experiments showed that the human anti-anthrax toxin antibodies according to several embodiments of the invention are potent inhibitors of the lethal toxin in vivo. The three parental antibodies and the two aglycosylated forms described may be therapeutically useful against anthrax infection and in the passive protection of high risk individuals. In particular, the two most potent anthrax toxin-neutralizing antibody (AVP-21D9 and AVP-22G12) were completely effective at a dose corresponding to 0.12 nmols/rat and 0.25 nmols/rat respectively. One of skill in the art will understand the appropriate dosages to prevent or treat anthrax infection in humans and other animals.

Detailed methodology and results are described below.

Methods

The in vivo anthrax toxin neutralization experiments were performed basically as described by Ivins B E, Ristroph J D, Nelson G O: Influence of body weight on response of Fischer 344 rats to anthrax lethal toxin. *Appl Environ Microbiol*, 1989, 55(8):2098, herein incorporated by reference. Male Fisher 344 rats with jugular vein catheters weighing between 200-250 g were purchased from Charles River Laboratories (Wilmington, Mass.). Human anti-anthrax PA IgG monoclonal antibodies AVP-21D9, AVP-22G12, AVP-1C6, AVP-21D9.1 and AVP22G12.1 were produced from recombinant CHO cell lines adapted for growth in serum free media. The human IgG monoclonal antibodies were purified by affinity chromatography on HiTrap Protein A, dialysed against PBS pH7.4 and filter sterilized. Rats were anaesthetized in an Isofluorane (Abbot, Ill.) EZ-anesthesia chamber (Euthanex Corp., PA) following manufactures guidelines. The antibody was administered via the catheter in 0.2 ml PBS/0.1% BSA (pH 7.4) and at either 5 minutes, 17 hour or a week later lethal toxin (PA 20 µg/LF 4 µg in 0.2 ml PBS/0.1% BSA (pH 7.4)) was administered via the same route. Five animals were used in each test group and four animals in each control. Test and control experiments were carried out at the same time using the same batch of reconstituted PA and LF toxins (List Laboratories, CA). Animals were monitored for discomfort and time of death versus survival, as assessed on the basis of cessation of breathing and heartbeat. Rats were maintained under anaesthesia for 5 hr post exposure to lethal toxin or until death to minimize discomfort. Rats that survived were monitored for 24 hours and then euthanized by carbon dioxide asphyxiation.

Results

Figure 11:
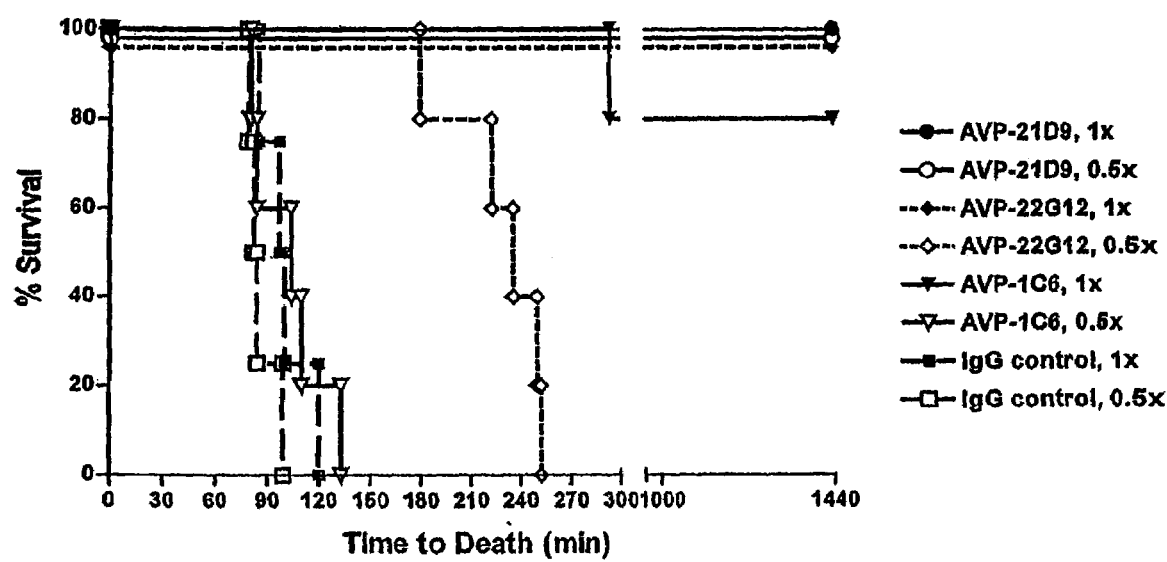
FIG. 11 shows protection of rats from a lethal toxin challenge five minutes after administration of antibody.

Effect of Anti-Anthrax PA Antibodies on Protection of Rats From Lethal Toxin Challenge: FIG. 11 illustrates the protection profile of the three antibodies AVP-21D9, 22G12 and 1C6 in the rat model at two doses 0.5× and 1× molar ratios relative to toxin challenge. AVP-21D9 protected rats at 0.5× and no deaths were observed in the 5 hr following toxin administration, likewise AVP-22G12 at 1× also showed complete protection. However with AVP22G12 at 0.5× the time to death was prolonged to 255 min. The administrations of lethal toxin 5 min after the infusion of 0.5× or 1× control human control IgG resulted in time to death of 85-120 min. AVP-1C6 at 1× conferred 80% protection and at 0.5× was not protective.

Effect of Antibody Glycosylation on Anti-Anthrax PA Antibodies on Protection of Rats from Lethal Toxin Challenge: Aglycosylated antibodies corresponding to AVP-21D9 or AVP-22G12 were generated by mutating a N-glycosylation site (N297Q) in the Fc region. These antibodies are designated as AVP-21D9.1 and AVP-22G12.1, respectively and compared to the glycosylated counterparts in the rat toxin challenge prophylaxis model. As described above, antibody was intravenously administered 5 minutes prior to the lethal toxin (PA/LF) challenge. Both AVP-21D9 and AVP-21D9.1 fully protected rats against anthrax toxin with 0.5× molar excess relative to PA toxin, whilst AVP-22G12.1 was slightly less potent than the parent molecule at 1× as shown in FIG. 12.

Duration of AVP-21D9 Antibody Mediated Protection of Rats from Lethal Toxin Challenge: To investigate the duration of protection afforded by a fully human antibody in Fischer rats AVP-21D9 was intravenously administered 17 hours or 1 week prior to the lethal toxin (PA/LF) challenge. As shown in FIG. 13, a single administration of AVP-21D9 at 1× protected 100% when challenged 17 hrs later. Over the extended period of time administration of AVP-21D9 at 10× dose showed 80% protection. Almost all control animals died within 120 min, one outlier had delayed time of death to 230 min.

Accordingly, the results showed that a single IV dose of AVP-21D9 or AVP-22G12 was found to confer full protection with only 0.5×(AVP-21D9) and 1× (AVP-22G12) molar excess relative to the anthrax toxin in the rat challenge prophylaxis model. AVP-21D9, AVP-22G12 and AVP-1C6 protect rats from anthrax lethal toxin at low dose. Aglycosylated versions of the most potent antibodies are also protective in vivo in the rat model, according to one embodiment. The protective effect of AVP-21D9 persists for at least one week in rats. These potent fully human anti-PA toxin-neutralizing antibodies are attractive candidates for development for in vivo human use as prophylaxis and/or treatment against Anthrax Class A bioterrorism toxins.

EXAMPLE 14

Human Anti-anthrax Protective Antigen Neutralizing Monoclonal Antibodies Derived from Donors Vaccinated with Anthrax Vaccine Adsorbed Potent anthrax toxin neutralizing human monoclonal antibodies were generated from peripheral blood lymphocytes obtained from Anthrax Vaccine Adsorbed (AVA) immune donors. In this particular experiment, donors were recruited that had been actively immunized with the current licensed anthrax vaccine (AVA). Despite vaccination the serum levels of anti-PA83 specific IgG and IgM were relatively low (2-3 µg/ml) in comparison to the anti-tetanus responses in both donors. In this embodiment, a SCID-HuPBL platform was used to demonstrate that the inventors could selectively direct the recall response by immunization of the chimeric animals. Immunization of the chimeric mice with recombinant PA83 resulted in a significant increase in specific IgG in some of the engrafted mice, in one case as high as 2 mg/ml (mouse 4152). In comparing first and second bleeds for both sets of chimeric mice, it is clear that a specific response was selectively enhanced in the animals upon boosting with antigen (see FIG. 2).

Not wishing to be bound by the following theory, it is believed that in mice that responded well to antigen challenge, the inventors recalled the human memory B cell response and recruited specific human helper T-cells. The specific recall leads to proliferation of antigen specific plasma cells.

The antibody producing cells in the chimeric mice were recovered from the spleen and peritoneal washes in sufficient numbers to permit fusion with a standard mouse myeloma P3X63Ag8.653 (Kearney J F, Radbruch A, Liesegang B, Rajewsky K: A new mouse myeloma cell line that has lost immunoglobulin expression but permits the construction of antibody-secreting hybrid cell lines. *J Immunol,* 1979. 123 (4):1548, herein incorporated by reference) to form hybridomas. The formation of mouse/human hybridomas using a murine fusion partner with human derived plasma cells can result in unstable hybrids, which can be challenging to clone, expand and isolate. Accordingly, in one embodiment, the inventors rescued the transcripts encoded by mRNA from a small cluster of cells and generating stable recombinant CHO cell lines and testing these for the activity. Hence the fusion with P3X63Ag8.653 with the human cells results in hybrids of antibody-producing cell, which permits identification of positive wells for specific IgG production and the rescue of immunoglobulin transcripts.

No particular heavy chain family or light chains dominated the human anti-PA response. In all but two cases, the inventors could assign $D_H$ segments usage. The array of $J_H$ and $J_L$ segments observed in the panel suggest that the approach is capturing the diversity present in the natural response to anthrax PA via vaccination with AVA. Another striking feature of the antibodies, according to one embodiment, is the exceptional high affinity for the target antigen and the very slow off-rates. Similar high affinities and slow off rates for anti-tetanus toxoid antibodies derived from engrafted HuPBL-SCID mice boosted with antigen. Thus, this may be a general feature of the protective anti-bacterial toxin response in humans.

Currently in the event of an inadvertent *Bacillus anthracis* spore exposure, two preventative measures can be taken. If the risk can be assessed well in advance, vaccination can be employed. In the event of near term or immediate post exposure antibiotic such as Cipro may be effective. Anthrax Vaccine Adsorbed (AVA) is the only licensed human anthrax vaccine in the United States. The vaccine is known to contain a mixture of cell products including PA, LF and EF, however the exact amounts are unknown (Tumbull P C, Broster M G, Carman J A, Manchee R J, Melling J: Development of antibodies to protective antigen and lethal factor components of anthrax toxin in humans and guinea pigs and their relevance to protective immunity. *Infect Immun,* 1986. 52(2):356, herein incorporated by reference). The immunization schedule consists of three subcutaneous injections at 0, 2 and 4 weeks and booster vaccination at 6, 12 and 18 months and it is suggested that annual boost may be required to maintain immunity. Mass vaccination in the event of anthrax spore release is an unlikely scenario. First, the time taken for effectiveness of such vaccination based on AVA or various rPA molecules in development may be too short, weeks as opposed to minutes. The utilization of antibiotic can inhibit bacterial growth and spread and may prevent some of the symptoms, but the administration needs to be timely and preferably prophylactically, even as such, the toxins released during the early stages of an infection may impair the immune system to cause lasting damage. In some instances, a combination of inhibiting anthrax bacteria and toxins is required early in an infection. High affinity human monoclonal PA neutralizing antibodies may provide immediate neutralization of the anthrax toxins.

In this experiment, the inventors accessed the human IgG response to the PA83 component of AVA and isolated a panel of high affinity potent PA neutralizing monoclonal antibodies. These antibodies were selected on the basis of binding to PA83, the form of the anthrax toxin released by the bacteria prior to cell bound furin processing and lethal toxin inhibition. Some of the embodiments described herein will be particularly useful for the generation of fully human monoclonal antibodies against various infectious disease targets from vaccinated or naturally exposed yet protected individuals.

The specific methodology and results of the experiment are described in detail as follows.

Methods

Selection of Donor: Plasma obtained at the time of blood collection by venipuncture from anthrax-vaccinated donors were pre-screened against a panel of antigens (including components of the anthrax exotoxin PA and LF) in an ELISA for both IgG and IgM. An internal calibrator was incorporated into each assay consisting of a control antiserum containing both IgG and IgM anti-tetanus toxoid. The IgG and IgM titres were compared across assays performed on different days, thereby permitting more robust comparisons of the entire donor panel.

Engraftment of SCID mice with human PBMC from pre-selected AVA immune donors. Peripheral blood mononuclear cells were enriched from whole blood of AVA immune donors by density gradient using Histopaque. SCID/bg 12 week old mice were each engrafted (via i.p. injection) with $2.5 \times 10^7$ human PBMC. They were treated concomitantly i.p. with a volume of conditioned medium which contains 0.2 mg of the anti-CD8 monoclonal antibody. The mice were immediately immunized (i.p.) with the recombinant PA and LF (List Laboratories) 10 µg each adsorbed to Alum (Imject®, Pierce, Rockford, Ill.) and subsequently boosted (ip) 8-28 day later. Mice were inoculated with 0.5 ml of EBV obtained from spent conditioned culture medium day 15 following engraftment. Test bleeds were obtained from the orbital sinus, on days 15 and 30. Two consecutive iv and i.p. boosts with the appropriate toxins were administered (typically, 5 µg each on day 35 and day 36; both in saline) prior to harvesting cells for fusion on day 37, also at which time an additional test bleed sample was obtained. The total IgG and specific PA IgG combined with potency in the RAW 264.7 cell bioassay were determined for the bleeds.

Generation of human hybridomas. Splenocytes, peritoneal washes, as well as lymphoblastoid cell line (LCL) human lymphocyte derived tumors, were harvested on day 37 from those mice showing positive test bleeds in PA ELISA and the appropriate bioassay (described below). Human hybridomas were generated from these in separate fusions using a mouse myeloma cell line P3X/63Ag8.653 (Kearney J F, Radbruch A, Liesegang B, Rajewsky K: A new mouse myeloma cell line that has lost immunoglobulin expression but permits the construction of antibody-secreting hybrid cell lines. *J Immunol*, 1979, 123(4):1548, herein incorporated by reference) with PEG-1500. Double selection to select against the EBV-LCL and the un-fused fusion partner was carried out using a combination of HAT selection and ouabain.

Variable Region IgH and IgL cDNA cloning and expression: Total RNA was prepared from specific ELISA positive hybridomas using RNeasy Mini Kit (Qiagen, Valencia, Calif.). Mixture of VH and VL cDNAs were synthesized and amplified in a same tube using One-Step RT-PCR Kit (Qiagen, Valencia, Calif.). Cycling parameters were 50° C. for 35 min, 95° C. for 15 min, 35 cycles of 94° C. for 30 sec, 52° C. for 20 sec and 72° C. for 1 min 15 sec, and 72° C. for 5 min.

Primers used for RT-PCR were:

```
For VHγ
Forward
a. CVH2
TGCCAGRTCACCTTGARGGAG        (SEQ ID NO: 17)

b. CVH3
TGCSARGTGCAGCTGKTGGAG        (SEQ ID NO: 18)

c. CVH4
TGCCAGSTGCAGCTRCAGSAG        (SEQ ID NO: 19)

d. CVH6
TGCCAGGTACAGCTGCAGCAG        (SEQ ID NO: 20)

e. CVH1257
TGCCAGGTGCAGCTGGTGSARTC      (SEQ ID NO: 21)

Reverse (located at 5' of CH1 region)
a. CγII
GCCAGGGGGAAGACSGATG          (SEQ ID NO: 22)

For VLκ
Forward
a. VK1F
GACATCCRGDTGACCCAGTCTCC      (SEQ ID NO: 23)

b. VK36F
GAAATTGTRWTGACRCAGTCTCC      (SEQ ID NO: 24)

c. VK2346F
GATRTTGTGMTGACBCAGWCTCC      (SEQ ID NO: 25)

d. VK5F
GAAACGACACTCACGCAGTCTC       (SEQ ID NO: 26)

Reverse (located in constant region)
a. Ck543
GTTTCTCGTAGTCTGCTTTGCTCA     (SEQ ID NO: 27)

For VLλ
Forward
a. VL1
CAGTCTGTGYTGACGCAGCCGCC      (SEQ ID NO: 28)

b. VL2
CAGTCTGYYCTGAYTCAGCCT        (SEQ ID NO: 29)

c. VL3
TCCTATGAGCTGAYRCAGCYACC      (SEQ ID NO: 30)

d. VL1459
CAGCCTGTGCTGACTCARYC         (SEQ ID NO: 31)

e. VL78
CAGDCTGTGGTGACYCAGGAGCC      (SEQ ID NO: 32)

f. VL6
AATTTTATGCTGACTCAGCCCC       (SEQ ID NO: 33)

Reverse (located in constant region)
a. CL2
AGCTCCTCAGAGGAGGGYGG         (SEQ ID NO: 34)
```

The RT-PCR was followed by nested PCR with High Fidelity Platinum PCR Mix (Invitrogen, Carlsbad, Calif.). A microliter of RT-PCR products were used for VHγ, VLκ or VLλ specific cDNA amplification in the separate tube. At the same time restriction enzyme sites were introduced at both ends. Cycling parameters were 1 cycle of 94° C. for 2 min, 60° C. for 30 sec and 68° C. for 45 sec, 35 cycles of 94° C. for 40 sec, 54° C. for 25 sec and 68° C. for 45 sec, and 68° C. for 5 min.

The each specific PCR products were separately purified, digested with restriction enzymes, and subcloned into appropriate mammalian full-length Ig expression vectors as described below.

Primers for nested PCR were:

```
For VHγ
Forward (adding BsrGI site at 5' end)
a. BsrGIVHF2
AAAATGTACAGTGCCAGRTCACCTTGARGGAG    (SEQ ID NO: 35)

b. BsrGIVHF3
AAAATGTACAGTGCSARGTGCAGCTGKTGGAG    (SEQ ID NO: 36)

c. BsrGIVHF4
AAAATGTACAGTGCCAGSTGCAGCTRCAGSAG    (SEQ ID NO: 37)

d. BsrGIVHF6
AAAATGTACAGTGCCAGGTACAGCTGCAGCAG    (SEQ ID NO: 38)

e. BsrGIVHF1257
AAAATGTACAGTGCCAGGTGCAGCTGGTGSARTC  (SEQ ID NO: 39)

Reverse (including native ApaI site)
a. CγER
GACSGATGGGCCCTTGGTGGA               (SEQ ID NO: 40)
```

VHγPCR products are digested with BsrG I and Apa I and ligated into pEEG1.1 that is linearized by Spl I and Apa, I double digestion.

```
For VLκ
Forward (adding AgeI site, Cys and Asp at
5' end)
a. AgeIVK1F
                                    (SEQ ID NO: 41)
TTTTACCGGTGTGACATCCRGDTGACCCAGTCTCC b. AgeIVK36F
                                    (SEQ ID NO: 42)
TTTTACCGGTGTGAAATTGTRWTGACRCAGTCTCC c. AgeIVK2346F
                                    (SEQ ID NO: 43)
TTTTACCGGTGTGATRTTGTGMTGACBCAGWCTCC
```

-continued

```
d. AgeIVK5F
                                       (SEQ ID NO: 44)
TTTTACCGGTGTGAAACGACACTCACGCAGTCTC

Reverse (adding SplI site, located between
FR4 and 5' of constant region)
a. SplKFR4R12
                                       (SEQ ID NO: 45)
TTTCGTACGTTTGAYYTCCASCTTGGTCCCYTG b. SplKFR4R3
                                       (SEQ ID NO: 46)
TTTCGTACGTTTSAKATCCACTTTGGTCCCAGG c. SplKFR4R4
                                       (SEQ ID NO: 47)
TTTCGTACGTTTGATCTCCACCTTGGTCCCTCC d. SplKFR4R5
                                       (SEQ ID NO: 48)
TTTCGTACGTTTAATCTCCAGTCGTGTCCCTTG
```

VLκ PCR products were digested with Age I and Spl I and ligated into pEEK1.1 vector linearlized by Xma I and Spl I double digestion.

```
For VLλ
Forward (adding ApaI site at 5' end)
a. ApaIVL1
ATATGGGCCCAGTCTGTGYTGACGCAGCCGCC     (SEQ ID NO: 49)

b. ApaIVL2
ATATGGGCCCAGTCTGYYCTGAYTCAGCCT       (SEQ ID NO: 50)

c. ApaIVL3
ATATGGGCCCAGTATGAGCTGAYRCAGCYACC     (SEQ ID NO: 51)

d. ApaIVL1459
ATATGGGCCCAGCCTGTGCTGACTCARYC        (SEQ ID NO: 52)

e. ApaIVL78
ATATGGGCCCAGDCTGTGGTGACYCAGGAGCC     (SEQ ID NO: 53)

f. ApaIVL6
ATATGGGCCCAGTTTTATGCTGACTCAGCCCC     (SEQ ID NO: 54)

Reverse (adding Avr II site, located between FR4
and 5' of constant region)
a. AvrIIVL1IR
TTTCCTAGGACGGTGACCTTGGTCCCAGT        (SEQ ID NO: 55)

b. AvrIIVL237IR
TTTCCTAGGACGGTCAGCTTGGTSCCTCCKCCG    (SEQ ID NO: 56)

c. AvrIIVL6IR
TTTCCTAGGACGGTCACCTTGGTGCCACT        (SEQ ID NO: 57)

d. AvrIIVLmixIR
TTTCCTAGGACGGTCARCTKGGTBCCTCC        (SEQ ID NO: 58)
```

VLλ PCR products were digested with Apa I and Avr II and ligated into pEELg vector linearlized by Apa I and Avr II double digestion.

The positive clones were identified after transient co-transfection by determining expression in the supernatants by indirect ELISA on PA coated plates. CHO K1 cells were transfected with different combinations of IgG and IgK cDNAs using Lipofectamine-2000 (Invitrogen, Carlsbad, Calif.). The supernatants were harvested 48-72 h after transfection. Multiple positive clones were sequenced with the ABI 3700 automatic sequencer (Applied Biosystems, Foster City, Calif.) and analyzed with Sequencher v4.1.4 software (Gene Codes, Ann Arbor, Mich.).

Stable cell line establishment: Ig heavy chain or light chain expression vector were double digested with Not I and Sal I, and then both fragments were ligated to form a double gene expression vector. CHO-K1 cells in 6 well-plate were transfected with the double gene expression vector using Lipofectamine 2000 (Invitrogen, Carlsbad, Calif.). After 24 hrs transfection cells were transferred to 10 cm dish with selection medium (D.MEM supplemented with 10% dialyzed FBS, 50 µM L-methionine sulphoximine (MSX), penicillin/streptomycin, GS supplement). Two weeks later MSX resistant transfectants were isolated and expanded. High producing clones were selected by measuring the antibody levels in supernatants in a PA specific ELISA assay. MSX concentration was increased from 50 to 100 µM to enhance the antibody productivity.

Antigen Binding ELISA: The presence of antibody to anthrax toxin components in human sera, engrafted SCID mouse sera, supernatants of hybridomas or transiently transfected CHO-K1 cells were determined by ELISA. Briefly flat bottom microtiter plates (Nunc F96 Maxisorp) were coated with the appropriate component of the *Bacillus anthracis* tripartite exotoxin, such as PA or LF, diluted sera was added to the wells for one hour at room temperature. Plates were washed and secondary antibody, goat anti-human IgG:HRP, Fcγ specific, or goat anti-human IgM:HRP, Fcµ specific was added and incubated for one hour at room temperature. After another wash step, a Results General: The range of antibodies generated were diverse with evidence of extensive hyper mutation, and all were of very high affinity for PA83~$1\times10^{-10\text{-}11}$M. Moreover, all were potent inhibitor of anthrax lethal toxin in vitro. Accordingly, in one embodiment, the generation of a panel of potent human monoclonal antibodies derived from anthrax vaccine adsorbed immune donors is provided. Protection against anthrax toxin challenge in an in vitro cell culture assay correlates well with affinity, with the highest affinity antibody AVP-21D9 (Kd=82 pM) exhibiting the most potent toxin inhibition.

Figure 14A:
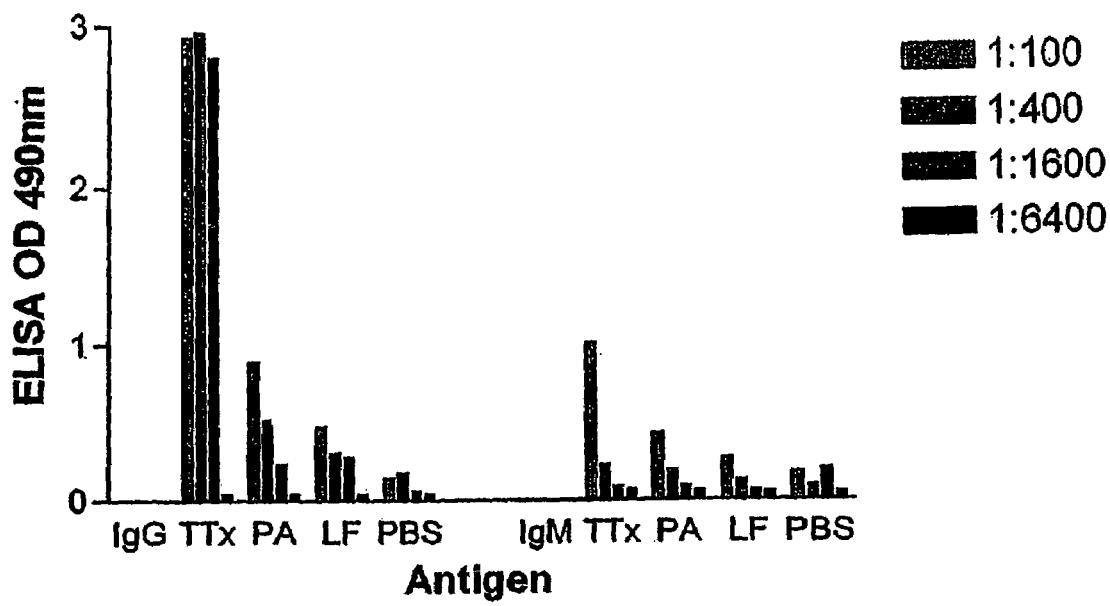
FIGS. 14A-B show ELISA panels of AVA vaccinated donors. Volunteers donors X064-004b and X064-019 plasma obtained at the time of blood collection by venipuncture from anthrax-vaccinated donors were pre-screened against tetanus toxoid, PA 83 or LF in an ELISA for both IgG and IgM.
Figure 14B:
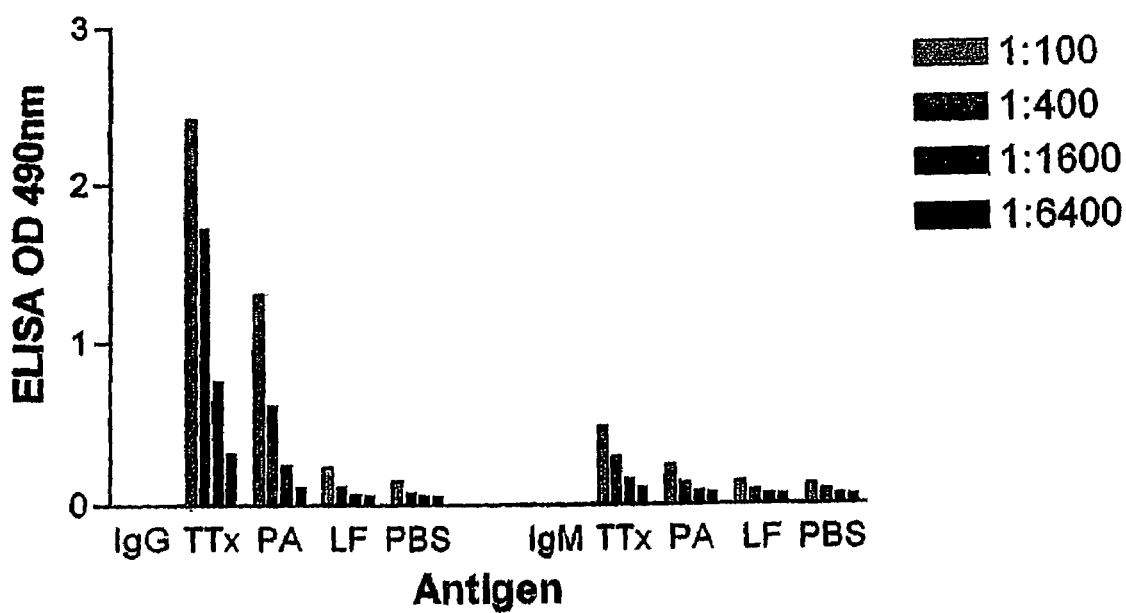

Donor Screening: Donors sera (X064-004b and X064-019) were screened for IgG and IgM against tetanus toxoid, PA and LF by ELISA. FIG. 14 shows that both donors had significant IgG responses to tetanus toxoid and some albeit low levels of specific IgG antibody against PA and LF.

Chimeric Engraft Screening: The PBL's from donor X064-004b and X064-019 were engrafted into mice designated X040-042 and X040-043 respectively. After boosting, sera from engrafted mice were screened for human IgG against PA. As shown in FIG. 2, the initial bleed after the first boost is plotted alongside the X064-004b donor sera. One engraft had an anti-PA IgG level that is 9× higher than the donor sera. Moreover, as shown in FIG. 2, the second bleed from the engrafted mice, a range of 8-30 fold increase in specific anti-PA IgG is observed. This increase in specific IgG over time in the engrafted mice is even more pronounced in the second engraft using cells from donor X064-01. The increase in specific anti-PA IgG in the second bleed is more than 500 fold relative to specific anti-PA in the donor sera.

Immunoglobulin Sequence Analysis: Following fusion, cells producing human anti-anthrax PA IgG were selected and the cDNA encoding the immunoglobulin variable regions were rescued from ELISA positive wells and sequenced. The cDNA templates were used to establish stable CHO K1 cell lines producing antibodies. Four neutralizing anti-PA antibodies were discovered by this approach. The VH families were represented by the VH3, VH1 and VH4. Likewise the VL families were represented by VK I and VL 3. Both VH and VL regions contained evidence of hyper mutation away from the germline. Table 3, below, lists the antibodies isolated by this approach and the D and J regions are assigned where possible using DNAPLOT from Vbase.

Kinetics of Binding: The equilibrium dissociation constant ($K_d$) for recombinant form of the antibodies were determined by BiaCore analyses. The rate constants $k_{on}$ and $k_{off}$ were evaluated directly from the sensogram in the BiaCore analysis and the $K_d$ was deduced. The results are summarized in Table 1, provided above.

In one embodiment, one feature of many of the protective antibodies is the very slow off rate, which contribute to the very high affinities $8.21\times10^{-11}$ M to $7.11\times10^{-10}$ M. The slow off rate may confer significant physiological advantages for toxin neutralization in vivo.

In vitro Lethal Toxin Inhibition: All the antibodies were initially selected based on binding to PA83 and secondly on inhibition of lethal toxin in a Raw 264.7 cell based in vitro assay. Only clones exhibiting toxin neutralization in a qualitative assay were developed further. The Raw 264.7 cell assay was adapted to compare the various antibodies for potency of toxin inhibition. In FIG. 4 a typical antibody dose response curve is reconstructed to provide an estimate of the $IC_{50}$ for AVP-21D9, AVP-1C6 and AVP-22G12. Again, the inhibitory potency ranking of all the selected antibodies were reflecting the same ranking observed for the binding to PA83.

EXAMPLE 15

Synergistic Effects of Anti-anthrax Antibody and Ciprofloxacin

In one embodiment of the invention, passive immunization is provided in conjunction with one or more other therapies, including but not limited to antibiotic therapy. In one embodiment, ciprofloxacin hydrochloride and/or other antibiotics are administered before, after, and/or simultaneously with one or more of the antibodies, or fragments thereof, described herein. In one embodiment, one or more antibiotics and antibodies are administered first, followed by vaccination with AVA and/or rPA, thereby conferring both immediate and long-term protection. In other embodiments, doxycycline can be administered. In other embodiments, ciprofloxacin, doxycycline, and/or penicillin can be administered. One of skill in the art will understand that several antibiotics (including, but not limited to ciprofloxacin, doxycycline, and penicillin) can be combined with one or more anti-anthrax antibodies to exert a preventive and/or therapeutic effect. The specific

TABLE 3

Human Anti-Anthrax PA83 Antibody Classification

| | VH | | | | | VL | | | |
|---|---|---|---|---|---|---|---|---|---|
| Designation | VH Class | VH Locus | # Mutations from germline | DH(RF) | JH | VL Class | VL Locus | # Mutations from Germline | JL |
| AVP-21D9 | VH3 | 3-43 | 26 | 6-19(1) | JH4b | VKI | L12 | 14 | JK1 |
| AVP-1C6 | VH3 | 3-73 | 8 | 6-13(1) | JH3b/a | VKI | L18 | 13 | JK4 |
| AVP-4H7 | VH4 | 4-39 | 29 | unknown | JH6b/a | VL3 | 3h | 22 | JL2/JL3a |
| AVP-22G12 | VH3 | 3-11 | 20 | unknown | JH5b | VL3 | 3r | 9 | JL2/JL3a |

The immunoglobulin sequence derived from the cDNA encoding the variable regions were used to search Vbase and the VH class, VH locus, DH and JH segments were assigned for the VH regions. Likewise VL class, VL locus and JL segments were assigned for the VL regions. Comparing the actual sequences and closest matched V family members the extent of somatic hyper mutation could be ascertained.

methodology and results of an experiment conducted to confirm the combined effects of antibody therapy and an exemplary antibiotic (ciprofloxacin) are described in detail as follows.

Methods: Hartley guinea pigs (250-300 g; n=9/group) and Swiss-Webster mice (25-30 g; n=10/group) were challenged by nasal instillation with 5 $LD_{50}$ Bacillus anthracis spores 24 hours prior to twice daily subcutaneous injections of ciprofloxacin for 6 days and/or a single intraperitoneal injection of anti-PA mAb (AVP-21D9). Animal survival was monitored.

Results: Control animals challenged with anthrax spores died within 7 days. AVP-21D9 provided protection and delayed the mean time of death; however, animals often succumbed to infection over the following weeks. The $ED_{50}$ dose of ciprofloxacin (3 mg/day, 6 days) protected the animals over a 20-day period; drug toxicity was noted with a dose of 5.4 mg/day. When AVP-21D9 (1.5-15 mg) was combined with a low, non-protective dose of ciprofloxacin (1.12 mg/day), we observed synergistic protection of the animals for 30 days; however, higher doses of ciprofloxacin were proportionately less effective. Similarly, Swiss-Webster mice were challenged with 5 $LD_{50}$ Bacillus anthracis Ames. Ciprofloxacin (0.9 mg/day) combined with 500 μg AVP-21D9 protected 100% of the animals for more than 30 days, while ciprofloxacin alone protected 60% and 21D9 alone protected 40%. All survivors were re challenged with $5LD_{50}$ values of Bacillus anthracis Ames spores by nasal instillation.

In view of the above results, it is believed that due to the asynchronous and delayed germination of the inhaled anthrax spores, prophylactic treatment of exposed individuals, in some embodiments, may require prolonged administration of antibiotics. Thus, in some embodiments of the invention, a formulation and method to achieve synergistic protection of guinea pigs and mice against anthrax comprising human mAb to PA and ciprofloxacin is provided. In one embodiment, levels of ciprofloxacin used in combination therapy will be less than that needed if ciprofloxacin was used alone. This antibody/antibiotic combination may be beneficial in the clinical care of patients exposed to Bacillus anthracis spores.

EXAMPLE 16

Mechanism of Action for Anti-anthrax Antibodies

Bacillus anthracis uses two distinct strategies to evade immune surveillance, thus facilitating dissemination throughout the body and a rapid rise in bacteremia. Initially, upon exposure to spores, the capsule composed of poly-D-glutamic acid provides a physical barrier to circumvent phagocytosis. Secondly, via the concerted effect of three proteins, PA, LF, and EF the immune response against the invading bacteria is compromised. PA is a 83 kD protein that binds to tumor endothelial marker-8 (TEM-8) or human capillary morphogenesis protein −2 (CMG-2), collectively called the anthrax toxin receptors (ATRs). The receptors are found on both macrophages and endothelial cells. LF is a protease that inhibits mitogen-activated protein kinase-kinase, which reduces the cytokine production by macrophages and ultimately leads to cell death. EF is an adenylate cyclase that generates cyclic AMP in eukaryotic cells and impairs the ability of neutrophils to engulf bacteria.

Although not wishing to be bound by this theory, it is believed that the toxic effects of anthrax are initiated by PA. It is believed that PA83 initially adheres to the membrane of the host cell, where it is then cleaved by a membrane-bound furin or furin-like protease which cleaves PA83 into two segments, PA63 and PA20. PA63, which is membrane-bound, assembles in groups of seven monomers (sometimes called a heptamer, or more broadly a multimer or oligomer), thereby forming a heptameric channel. The haptamer binds EF and LF, and allows EF and LF to enter the host cell to exert their toxic effects.

Although previous researchers have attempted to prevent the binding of EF and LF to PA63, the inventors believe that this is the first report of a composition and method that prevents anthrax toxicity by preventing the assembly of the PA63 heptamer.

The specific methodology and results of an experiment conducted to evaluate the mechanism of action of anti-anthrax toxins is described below.

Materials and Methods: The binding of the monoclonal antibodies to distinct or overlapping epitopes on PA83 was determined by surface plasmon resonance. Anti-human IgG capture antibody (goat anti-human Fc gamma specific, Jackson ImmunoResearch) was coupled to a CM-5 chip through standard amine chemistry using an immobilization guide provide by the Biacore (Biacore Inc, N.J.), whereby a response unit (RU) value of 10,000 units was approached. The first human monoclonal antibody was applied, followed by pooled human (non-immune) IgG blocking antibody, PA83 (PA83, and LF both purchased from List Biological Labs, CA) followed sequentially with the second and third monoclonal antibodies. The order in which the antibodies were applied was changed in subsequent runs to cover all permutations with a vast excess of human polyclonal IgG blocking between steps. The test reagents (PA, MAbs) were applied at 20 μg/ml in HBS-EP buffer provide by Biacore, the blocking antibody human IgG/K1 (Sigma Co, MO) was used at 40 μg/ml. The resulting binding data is presented in FIG. 15.

Figure 16A:
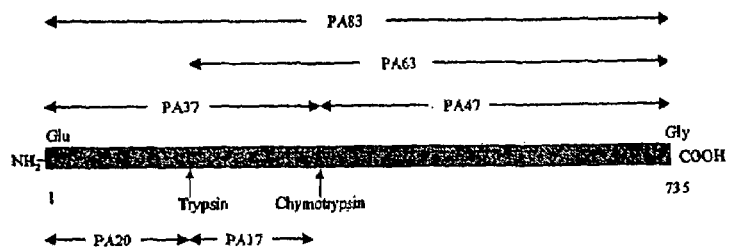
FIGS. 16A-C shows monoclonal antibodies recognizing domains on PA83.
Figure 16B:
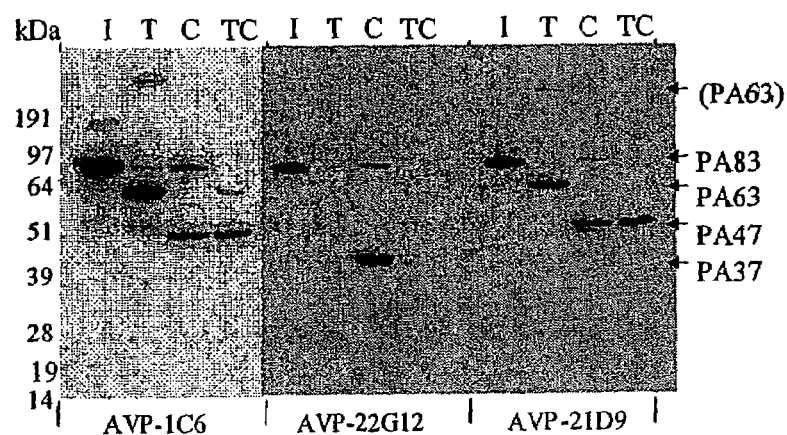

To map the antibody recognition to distinct portion of the PA83, western blot analysis was undertaken. In FIG. 16A, a schematic of fragments of PA83 generated by trypsin and chymotrypsin digests based on the sequences and mapping studies previously described is shown (Welkos S L, Lowe J R, Eden-McCutchan F, Vodkin M, Leppla S H, Schmidt J J, Sequence and analysis of the DNA encoding protective antigen of Bacillus anthracis, Gene 69 (1988), 2:287-300; Novak J M, Stein M P, Little S F, Leppla S H, Friedlander A M, Functional characterization of protease-treated Bacillus anthracis protective antigen, J Biol Chem 267 (1992), 24:17186-93, both herein incorporated by reference). Intact PA83, trypsin, chymotrypsin and a combination of trypsin and chymotrypsin generated PA fragments were probed with human monoclonal antibodies AVP-1C6, AVP-22G12 and AVP-21D9 in a western blot (FIG. 16B).

Figure 16C:
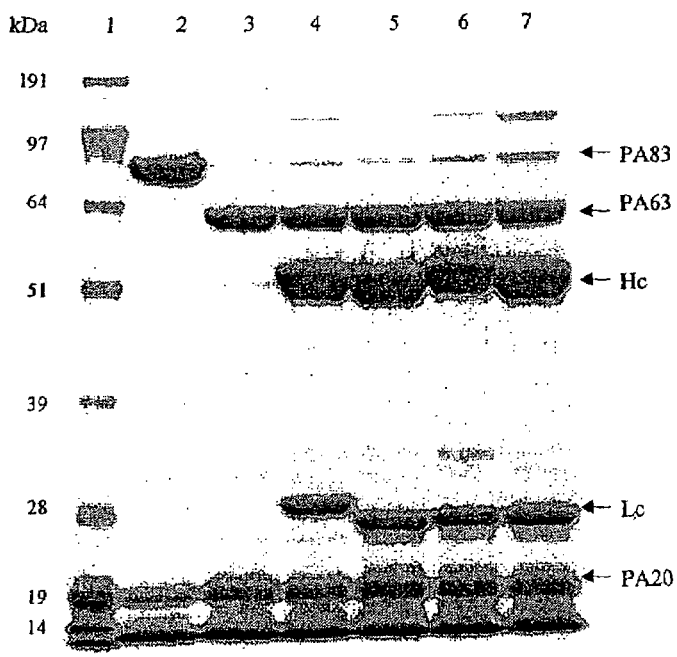

To investigate whether the antibody bound to PA83 blocked subsequent processing, PA83 was pre-incubated with antibodies and treated with trypsin. The resulting mixtures were pulled down with protein A and analysed by SDS-PAGE and Coomassie staining (FIG. 16C).

Figure 17B:
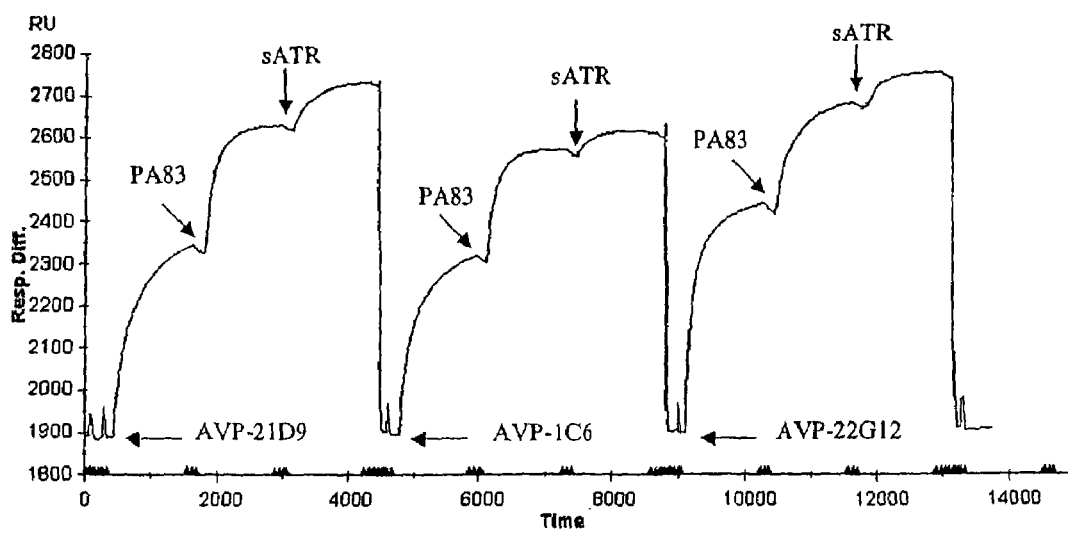

The role of antibodies in inhibiting the binding of lethal factor to PA63 oligomer was again investigated by surface plasmon resonance. PA63 (PA63 oligomer, List Laboratories, CA) was immobilized on a BiaCore CM5 chip, essentially as described above, antibody captured and lethal factor applied. The binding events were monitored and are presented in a sensogram (FIG. 17A). Also, the role of antibodies in blocking binding of the anthrax toxin PA83 to its receptor was investigated in a similar manner. Anti-human Fc gamma was conjugated to the CM5 chip, human monoclonal anti-PA antibody was captured, PA83 was bound and the soluble anthrax toxin receptor was applied (plasmid encoding full-length ATR was kindly provided by Dr. Ken Bradley UCLA). Again each binding event was monitored by surface plasmon resonance (FIG. 17B).

Figure 18:
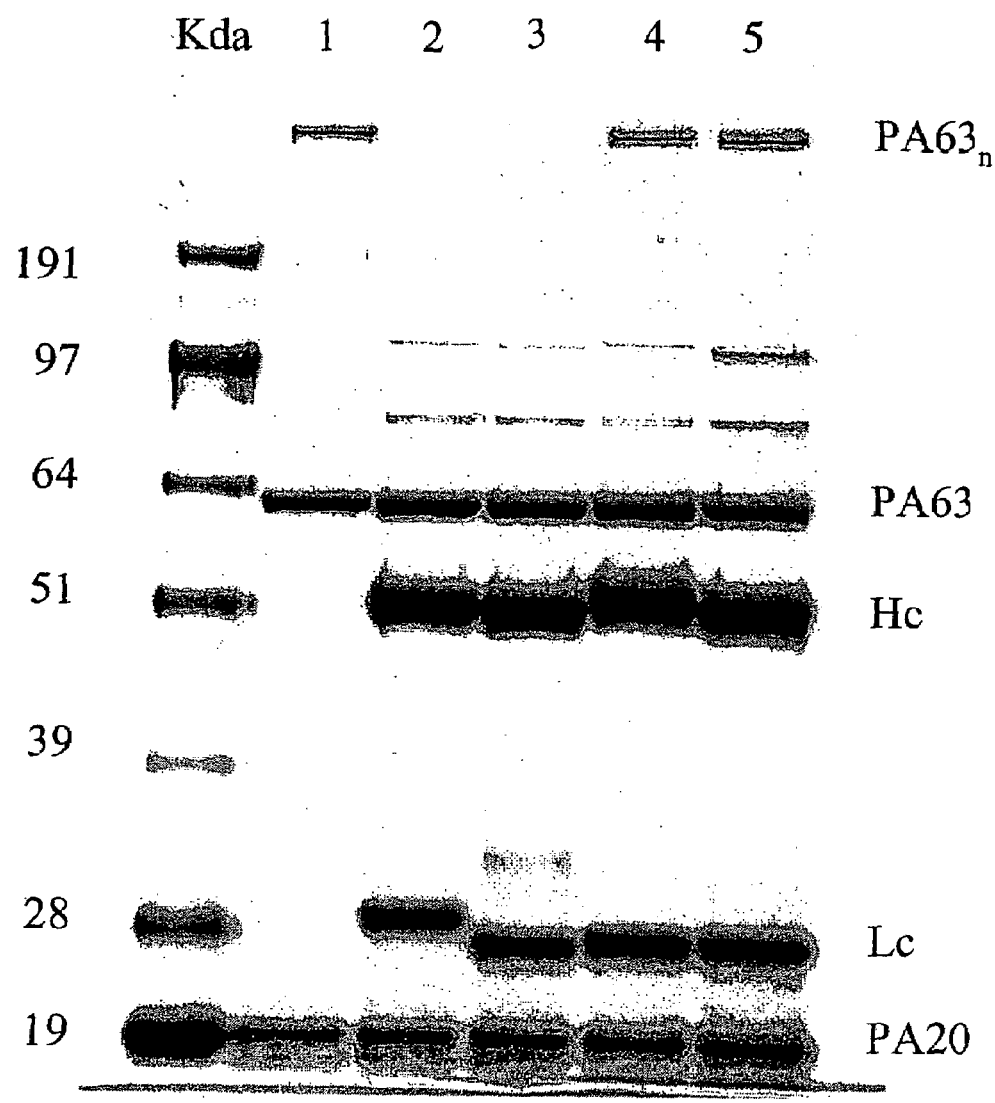
FIG. 18 shows the effects of anti-PA antibodies on PA63 oligomer formation. Coomassie stained SDS-PAGE of antibody bound PA83 treated with trypsin. Lane assignment molecular weight markers: (1) PA83 trypsin treated no antibody; (2) AVP-22G12; (3) AVP-21D9; (4) AVP-1C6; (5) AVP-1451 isotype matched human IgG anti-tetanus control.

Finally, to determine if the antibodies inhibited the formation of PA63 heptamer, equimolar amounts of PA83 (0.25 nmol) and anti-PA antibody (0.25 nmol) were mixed in 70 μl of PBS. After 30 minutes incubation at room temperature, the mixture was transferred to 4° C. and 10 μl of ice-cold trypsin (50 μg/ml) was added for 5 minutes. Trypsin was inactivated by the addition of 5 µl trypsin and chymotrypsin inhibitor (10 mg/ml). Citric phosphate buffer (115 µl of 0.1M, pH 5.0) was then added to bring the pH to 5.0 to facilitate PA63 oligomerization. SDS loading buffer was added and the mixtures placed on boiling water for 10 minutes. Polypeptides were separated in a 10% Bis-Tris gel under reducing condition. Protein bands were visualized by Coomassie blue staining (FIG. 18).

Figure 15:
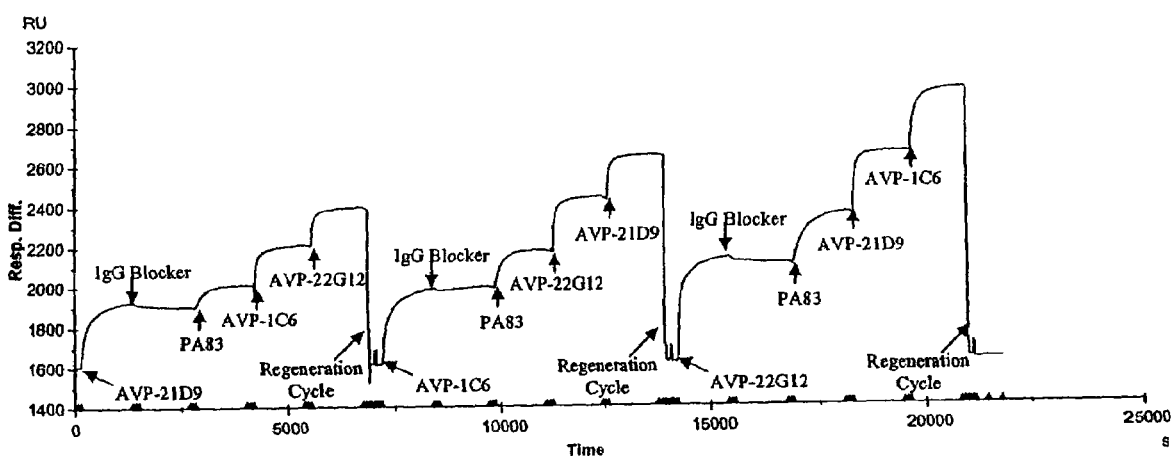
FIG. 15 shows a sensogram of sequentially bound anti-PA antibodies, demonstrating that irrespective of the order of binding all three human monoclonal anti-PA83 antibodies (AVP-21D9, 22G12 and 1C6) can bind to a single PA83 molecule.

Results: Sequential binding of anti-PA antibodies to PA83 indicated that they bound to distinct non-overlapping epitopes (FIG. 15). Western blot analysis of intact PA 83 indicated all three antibodies recognized linear epitopes on PA83 (FIG. 16A and 16B). AVP-21D9 and AVP-1C6 mapped to the carboxyl domain PA47 generated by chymotrypsin digestion. The binding of AVP-22G12 mapped to the chymotrypsin generated fragment PA37 which contains the natural furin cleavage site. Treating PA83 with trypsin abolished AVP-22G12 binding in the western blot. Initially, this suggested that AVP-22G12 itself might act by inhibiting the cleavage of PA83 to PA63. To test this hypothesis, PA83 was pre-incubated with antibody prior to trypsin addition, the resulting mixture was analyzed. Surprisingly, AVP-22G12 bound to PA83 permits cleavage by trypsin, implying that it binds close to (and possibly spans) the accessible cleavage site (FIG. 16C).

To determine whether the antibodies efficacy was in part due to inhibiting LF binding to PA63 oligomer, the interactions between PA63 oligomer, antibody and LF were investigated. AVP-22G12 did not bind to preformed PA63 oligomer, thus by default did not appear to compete for EF/LF binding; though AVP-21D9 had very weak binding (possibly due to the presence of a small amount of PA63 monomer) and AVP-1C6 bound to the PA 63 oligomer, neither inhibited LF binding (FIG. 17A). All the antibodies bound PA83, which subsequently bound soluble ATR (sATR) (FIG. 17B). However partial inhibition of sATR binding was observed on AVP-1C6 captured PA83, hinting at a possible mode of action.

In this particular example, AVP-21D9 and AVP-22G12 did not inhibit PA83 and sATR interaction, nor did they appear to prevent subsequent processing to PA63 or the binding of LF to PA 63 oligomer. Yet, paradoxically they were the two most potent inhibitors of anthrax lethal toxin (PA/LF) in vitro and in vivo in rats. AVP-22G12 bound to native PA83, denatured PA83 and PA37, but not to the preformed heptamer or monomer PA63. Cleavage of PA83 to PA63 and PA20 completely abolished the binding of AVP-22G12. However, if PA83 was bound to the antibody and subsequently cleaved by trypsin, the resulting PA63-PA20 antibody complex remains bound (FIG. 16B and FIG. 16C). These observations implied that at least for AVP-22G12 the step of toxin neutralization probably occurred prior to heptamer assembly. In natural exposure to anthrax, upon cleavage of PA83 to PA63 and the release of PA20, the PA63 spontaneously forms a heptamer.

An oligomer of PA63 can be formed in vitro by treating PA83 with trypsin and adjusting the pH 5.0. Once formed it is stable in the presence of sodium dodecyl sulphate (SDS) as shown in lane 1 of FIG. 18. Antibody bound PA83 was cleaved by trypsin to mimic the natural furin like protease, to generate PA63-PA20 and pH was adjusted to 5.0 to facilitate heptamer assembly. The mixtures were examined by SDS-PAGE. In the absence of anti-PA antibody (Lane 1) or in the presence of an isotype matched control antibody (Lane 5), the PA63 oligomer formed readily. Both AVP-22G12 and AVP-21D9 (Lanes 2 and 3) completely inhibited heptamer formation (FIG. 18). Since western blot analysis had shown that the two antibodies bind to distinct regions of PA83, the antibodies prevented the oligomer formation via distinct mechanisms. It was demonstrated that AVP-22G12 binds to a linear epitope on PA83 that possibly spans PA63 and PA20 cleavage site, but still permits access to protease site and the clipped molecule retains PA20. It is plausible that the retention of PA20 on the antibody-antigen complex may hinder the subsequent heptamer formation. Whereas AVP-21D9 bound to a distal linear epitope within the PA47 polypeptide and prevented PA oligomer formation possibly by masking potential assembly interfaces. It has previously been demonstrated that correct pore assembly is needed to facilitate LF and EF entry into cells, thus blocking this portal molecule effectively protects against the effects of both EF and LF anthrax toxin(s).

Thus, in view of the above results, it is believed that, in some embodiments, fully human antibodies generated in response to AVA vaccination neutralize anthrax exotoxin PA by interfering with and/or preventing PA63 oligomer assembly.

Antibodies to Anthrax Made by Other Methods: In several embodiments of the present invention, a composition and method to treat and/or prevent anthrax that prevents PA63 oligomer assembly is provided. The phrase "prevents PA63 assembly," as used herein, shall be given its ordinary meaning and shall also mean partially, substantially, or fully inhibiting, interfering with, and/or disrupting the assembly of PA63 into an oligomer. In one embodiment, the composition used to prevent PA63 heptamer assembly is a binding agent, such as the anti-anthrax antibodies generated by the methods of the present invention. For example, in one embodiment, the antibody is a fully human monoclonal antibody generated using immuno-compromised mice. In other embodiments, however, antibodies created by the engineering of bacteriophages to display human monoclonal antibodies on their surface are used. In yet other embodiments, the composition comprises a mouse monoclonal antibody. In other embodiments, polyclonal antibodies are used. In yet other embodiments, humanized or chimeric antibodies are used. Methods of making the antibodies described above (e.g., making humanized antibodies, non-human monoclonal antibodies, and polyclonal antibodies) are well-known in the art.

In one embodiment, a composition and method for treating a mammal exposed to anthrax, or passively immunizing a mammal pre-exposure, is provided. In one embodiment, the method comprises administering a binding agent to a mammal, wherein the binding agent prevents the assembly of a PA63 heptamer. By preventing the assembly of the PA63 oligomer, the binding agent, in some embodiments, inhibits transport of EF and/or LF into a mammalian host cell, thereby protecting the mammal from the toxic effects of anthrax. As discussed above, the binding agent can be a monoclonal or polyclonal antibody. The binding agent can be fully human, humanized, or non-human. Thus, any binding agent that prevents, or otherwise interferes with the assembly of a PA63 oligomer can be used according to an embodiment of the current invention. Indeed, the binding agent need not be an antibody. For example, small molecules, such as peptides, that can bind to a site on the PA63 molecule, or otherwise prevent the assembly of the PA63 heptamer, can also be used (Bachhawat-Sikder, K., and Kodadek, T. (2003). Mixed element capture agents (MECAs): A simple strategy for the construction of synthetic, high affinity protein capture ligands. J Amer Chem Soc 125, 13995-14004, herein incorporated by reference).

Figure 20:
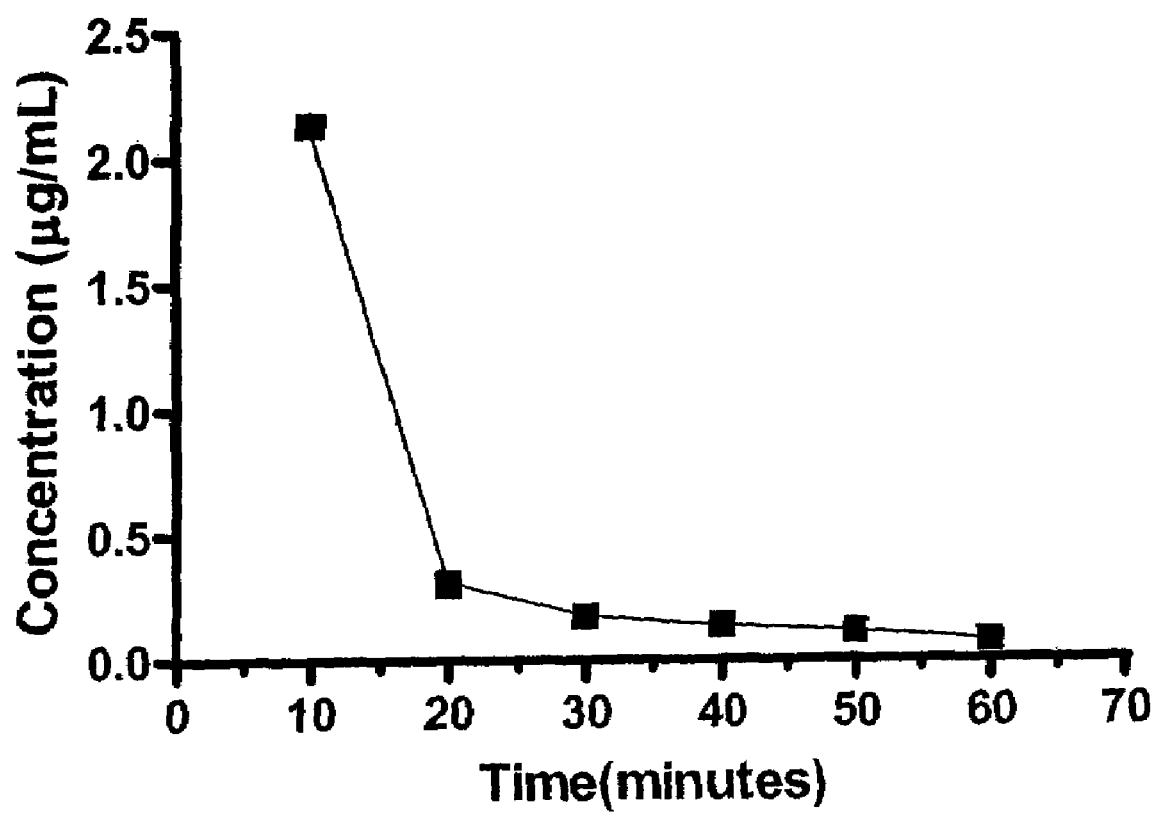
FIG. 20 shows PA83 detection data in rat serum. Such an assay can be used in one or more kits according to several embodiments of the invention.

FIG. 20 shows PA83 detection data in rat serum. In one example, purified PA83 was injected intravenously into rats at time t=0 and blood samples were taken every 10 minutes. Blood was collected in tubes containing heparin and spun immediately to separate the plasma from the cells. The samples were used in an ELISA assay as following. ELISA plates were coated overnight with 5 μg/ml AVP-1C6, which serves as capture antibody. The plates were washed and blocked, and serum samples were added for 30 minutes. The presence of PA83 in the samples was detected using biotinylated-polyclonal goat anti-PA (List Laboratories) and HRP-conjugated Avidin, followed by chromogenic detection. The concentration was calculated from a standard curve using PA83 at defined concentrations. Other monoclonal antibodies described herein could also be used instead of polyclonal serum. The methods and data show an example of an assay that is capable of detecting PA levels in serum. Such an assay can be used in one or more kits according to several embodiments of the invention. Kits, in some embodiments, can be used to determine the severity of anthrax exposure and/or the length of time from anthrax exposure. For example, by determining the levels of anthrax components or metabolites in serum (or other biological samples), a kit may be useful in determining the severity and type of anthrax infection.

In some embodiments, the binding agent prevents assembly of the PA heptamer by binding to a site on the PA63 molecule. In other embodiments, the binding agent prevents assembly of the PA heptamer by binding to a site on the PA20 molecule. In further embodiments, the binding agent prevents assembly of the PA heptamer by binding to a site on the PA83 molecule. In yet other embodiments, the binding agent prevents assembly of the PA heptamer by binding to a non-PA molecule that is needed for PA assembly.

Although several different binding agents can be used in accordance with certain embodiments of the present invention, antibodies (as opposed to non-antibody agents) may be particularly advantageous because antibodies may bind with greater affinity and specificity to the desired epitope, thus preventing the assembly of PA63 more effectively. Further, fully human antibodies are especially advantageous because fully human antibodies may exert fewer side-effects in the body, and are likely to be eliminated less rapidly from the body, thereby reducing the frequency and amount of dosing. Further, fully human antibodies may have higher affinities and specificities.

While a number of preferred embodiments of the invention and variations thereof have been described in detail, other modifications and methods of use will be readily apparent to those of skill in the art. Accordingly, it should be understood that various applications, modifications and substitutions may be made of equivalents without departing from the spirit of the invention or the scope of the claims.

What is claimed is:

1. A method for passively immunizing or treating a mammal against anthrax toxin, comprising:
   administering to said mammal a dose of a fully human monoclonal antibody or fragment thereof that binds to protective antigen (PA), wherein said dose is effective to neutralize said PA toxin activity,
   wherein said antibody or fragment thereof comprises a heavy chain and a light chain,
   wherein said heavy chain comprises the amino acids of SEQ ID 2; and
   wherein said light chain comprises the amino acids of SEQ ID 4.

2. The method of claim 1, wherein said mammal has not been exposed to said anthrax toxin.

3. The method of claim 1, further comprising administering an amount of one or more antibiotics sufficient to inhibit *Bacillus anthracis* growth.

4. The method of claim 1, wherein said fully human monoclonal antibody or fragment thereof binds to at least one of an intact form of the protective antigen, wherein said intact form has a molecular weight of about 83 kilodaltons or a cleaved form of the protective antigen, wherein the cleaved form has a molecular weight of about 63 kilodaltons.

5. The method of claim 1, further comprising administering one or more additional fully human monoclonal antibodies, wherein said one or more additional fully human monoclonal antibodies bind to at least a portion of said anthrax toxin.

6. The method of claim 5, wherein said one or more additional fully human monoclonal antibodies are administered sequentially with the antibody encoded by SEQ ID 2 and SEQ ID 4.

7. The method of claim 1, further comprising administering an additional therapeutic agent.

8. The method of claim 7, wherein said additional therapeutic agent comprises an antibiotic, wherein said antibiotic is selected from the group consisting of one or more of the following: ciprofloxacin, doxycycline, and penicillin.

9. The method of claim 7, wherein said additional therapeutic agent is administered simultaneously with said fully human monoclonal antibody or fragment thereof.

10. The method of claim 7, wherein said additional therapeutic agent is administered before or after said fully human monoclonal antibody or fragment thereof.

11. A method for passively immunizing or treating a mammal, comprising:
    administering to said mammal a dose of a fully human monoclonal antibody or fragment thereof that binds to protective antigen (PA), wherein said dose is effective to neutralize said PA toxin activity,
    wherein said antibody or fragment thereof comprises a heavy chain and a light chain,
    wherein said heavy chain comprises a heavy chain CDR (complementary determining region) 1, heavy chain CDR 2, and heavy chain CDR 3 as set forth in amino acids 31-35 of SEQ ID 2, amino acids 50-66 of SEQ ID 2, and amino acids 99-110 of SEQ ID 2 respectively; and
    wherein said light chain comprises a light chain CDR 1, light chain CDR 2, and light chain CDR 3 as set forth in amino acids 24-34 of SEQ ID 4, amino acids 50-56 of SEQ ID 4, and amino acids 89-96 of SEQ ID 4 respectively.

12. The method of claim 5, wherein the additional fully human monoclonal antibody binds to protective antigen (PA), wherein said additional antibody comprises a heavy chain and a light chain, wherein said heavy chain comprises the amino acids of SEQ ID NO:6; and wherein said light chain comprises the amino acids of SEQ ID NO:8.

13. The method of claim 5, wherein the additional fully human monoclonal antibody binds to protective antigen (PA), wherein said additional antibody comprises a heavy chain and a light chain, wherein said heavy chain comprises the amino acids of SEQ ID NO:10; and wherein said light chain comprises the amino acids of SEQ ID NO:12.

14. The method of claim 5, wherein the additional fully human monoclonal antibody binds to protective antigen (PA), wherein said additional antibody comprises a heavy chain and a light chain, wherein said heavy chain comprises the amino acids of SEQ ID NO:14; and wherein said light chain comprises the amino acids of SEQ ID NO:16.

* * * * *